(12) United States Patent
Seeberger et al.

(10) Patent No.: US 10,688,169 B2
(45) Date of Patent: Jun. 23, 2020

(54) **VACCINES AGAINST CARBAPENEM-RESISTANT *KLEBSIELLA PNEUMONIAE***

(71) Applicant: Max-Planck-Gesellschaft zur Förderung der Wissenschaften e.V., Munich (DE)

(72) Inventors: Peter H. Seeberger, Kleinmachnow (DE); Claney Lebev Pereira, Berlin (DE); Guozhi Xiao, Berlin (DE); Naeem Khan, Berlin (DE); Chakkumkal Anish, The Hague (NL)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 156 days.

(21) Appl. No.: 15/560,719

(22) PCT Filed: Mar. 29, 2016

(86) PCT No.: PCT/EP2016/056832
§ 371 (c)(1),
(2) Date: Sep. 22, 2017

(87) PCT Pub. No.: WO2016/156338
PCT Pub. Date: Oct. 6, 2016

(65) Prior Publication Data
US 2018/0078630 A1 Mar. 22, 2018

(30) Foreign Application Priority Data
Mar. 27, 2015 (EP) ..................... 15161528

(51) Int. Cl.
*C07H 15/04* (2006.01)
*C07H 15/08* (2006.01)
*A61K 31/702* (2006.01)
*A61K 31/7028* (2006.01)
*A61K 39/108* (2006.01)
*A61K 39/00* (2006.01)

(52) U.S. Cl.
CPC ........ *A61K 39/0266* (2013.01); *A61K 31/702* (2013.01); *A61K 31/7028* (2013.01); *C07H 15/04* (2013.01); *C07H 15/08* (2013.01); *A61K 2039/55566* (2013.01); *A61K 2039/6037* (2013.01)

(58) Field of Classification Search
None
See application file for complete search history.

(56) References Cited

U.S. PATENT DOCUMENTS

2014/0193416 A1* 7/2014 Seeberger ............... C07H 3/06
424/137.1

FOREIGN PATENT DOCUMENTS

EP 0735049 A2 10/1996
WO WO 98/30224 7/1998

OTHER PUBLICATIONS

Castelli et al., "2,2-dimethyl-4-(4-methoxy-phenoxy)butanoate and 2,2-dimethyl-4-azido Butanoate: Two New Pivaloate-ester-like Protecting Groups" Organic Letters vol. 15 No. 9 pp. 2270-2273 (Year: 2013).*
Alonsodevelasco et al., "*Streptococcus pneumoniae*: Virulence Factors, Pathogenesis, and Vaccines" Microbiological Reviews (1995) 59(4):591-603.
Beurret et al., "Structural investigation of the capsular polysaccharide from Klebsiella K19 by chemical and N.M.R. analyses" Carbohydr. Res. (1986) 157:13-25.
Boutet et al., "Synthesis of Two Tetra- and Four Pentasaccharide Fragments of *Shigella flexneri* Serotypes 3a and X O-Antigens from a Common Tetrasaccharide Intermediate" Eur. J. Org. Chem. (2008) 2008(33):5526-5542.
Buskas et al., "The Immunogenicity of the Tumor-Associated Antigen Lewisy May Be Suppressed by a Biofunctional Cross-Linker Required for Coupling to a Carrier Protein" Chemistry—A European Journal (2004) 10(14):3517-3524.
Calin et al. "Total synthesis of the *Escherichia coli* O111 O-specific polysaccharide repeating unit" Chem. Eur. J. (2013) 19(12):3995-4002.
Castelli et al., "2,2-Dimethyl-4-(4-methoxy-phenoxy) butanoate and 2,2-Dimethyl-4-azido Butanoate: Two New Pivaloate-ester-like Protecting Groups" Org. Lett. (2013) 15(9):2270-2273.
Cryz et al., "Safety and Immunogenicity of a polyvalent Klebsiella capsular polysaccharide vaccine in humans" Vaccine (1986) 4(1):15-20.
Kawano et al., "Natural killer-like nonspecific tumor cell lysis mediated by specific ligand-activated Valphal 4 NKT cells" Proc. Natl Acad. Sci. USA (1998) 95:5690-5693.
Kubler-Kielb et al., "The capsular polysaccharide and lipopolysaccharide structures of two carbapenem resistant Klebsiella pneumoniae outbreak isolates" Carbohydrate Research (2012) 369:6-9.
Martin et al., "Glycan arrays containing synthetic Clostridium difficile lipoteichoic acid oligomers as tools toward a carbohydrate vaccine" Chem. Comm. (2013) 49(64):7159-7161.
Mo et al., "Endolysins of *Bacillus anthracis* Bacteriophages Recognize Unique Carbohydrate Epitopes of Vegetative Cell Wall Polysaccharides with High Affinity and Selectivity"J. Am. Chem. Soc. (2012) 134(37):15556-15562.

(Continued)

*Primary Examiner* — Eric Olson
(74) *Attorney, Agent, or Firm* — Knobbe Martens Olson & Bear LLP

(57) ABSTRACT

The present invention relates to synthetic saccharides of general formula (I): V*—[U$_{x+2}$—U$_{x+1}$—U$_x$]$_n$—V—O-L-NH$_2$ that are related to carbapenem-resistant *Klebsiella pneumoniae* capsular polysaccharide and conjugates thereof. Said conjugates and pharmaceutical composition containing said conjugates are useful for prevention and/or treatment of diseases associated with carbapenem-resistant *Klebsiella pneumoniae*. Furthermore, the synthetic saccharides of general formula (I): V*—[U$_{x+2}$—U$_{x+1}$—U$_x$]$_n$—V—O-L-NH$_2$ are useful as marker in immunological assays for detection of antibodies against carbapenem-resistant *Klebsiella pneumoniae* bacteria.

11 Claims, 7 Drawing Sheets

(56) References Cited

OTHER PUBLICATIONS

Figure 1:
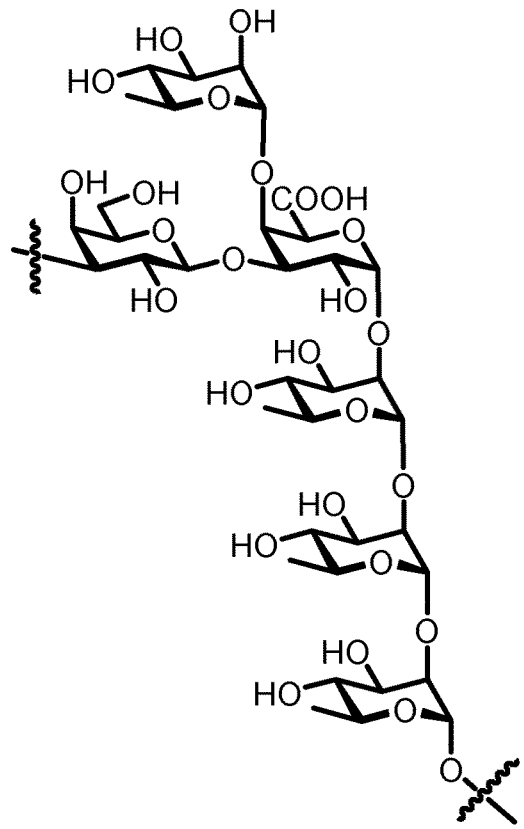

Podschun et al., "*Klebsiella* spp. as Nosocomial Pathogens: Epidemiology, Taxonomy, Typing Methods and Pathogenicity Factors" (Jan. 1, 1998) pp. 589-603.
Vliegenthart et al., "Carbohydrate based vaccines" FEBS Letters (2006) 580(12):2945-2950.
International Search Report and Written Opinion dated Jun. 20, 2016 for PCT Application No. PCT/EP2016/056832, filed Mar. 29, 2016.
International Preliminary Report on Patentability dated Oct. 3, 2017 for PCT Application No. PCT/EP2016/056832, filed Mar. 26, 2016.

* cited by examiner

Figure 2

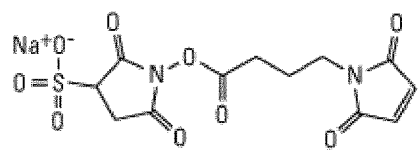

Sulfo-GMBS
N-(γ-Maleimidobutyryloxy) sulfosuccinimide ester
MW 382.28
Spacer Arm 7.3 Å

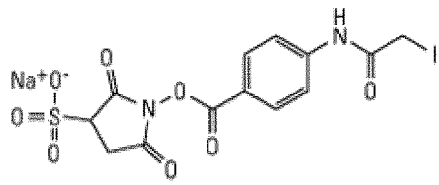

Sulfo-SIAB
Sulfosuccinimidyl (4-iodoacetyl) aminobenzoate
MW 504.19
Spacer Arm 10.6 Å

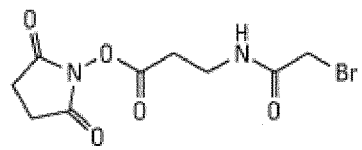

SBAP
Succinimidyl-3-(bromoacetamido)propionate
MW 307.10
Spacer Arm 6.2 Å

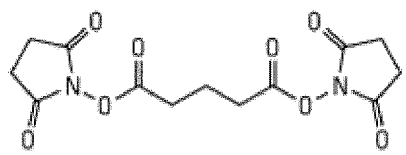

DSG
Disuccinimidyl glutarate
MW 326.26
Spacer Arm 7.7 Å

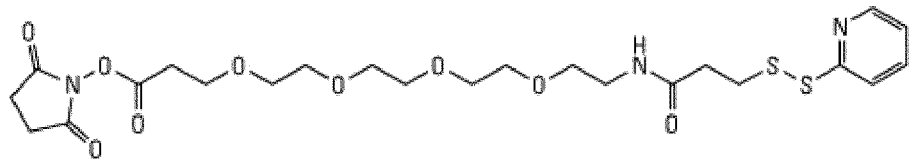

PEG4-SPDP
2-Pyridyldithiol-tetraoxatetradecane-N-hydroxysuccinimide
MW 559.17
Spacer Arm 25.7 Å

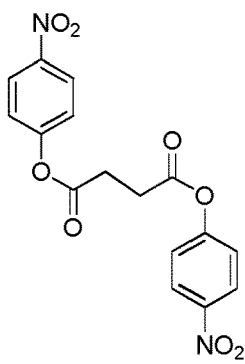

Bis-(4-nitrophenyl)succinate

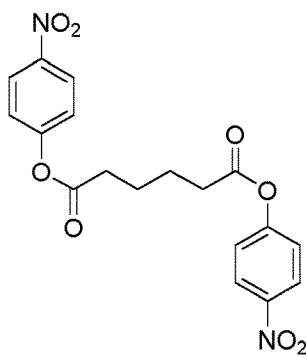

Bis-(4-nitrophenyl) adipate

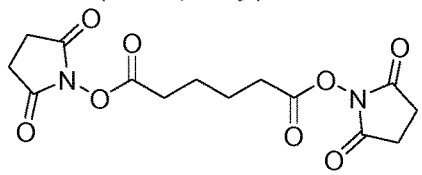

DSA
Disuccinimidyl adipate

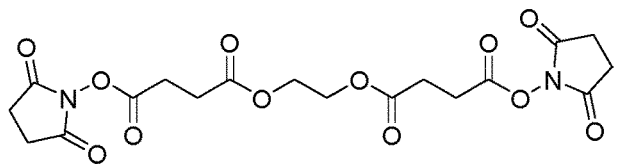

Ethylene glycol-bis(succinic acid N-hydroxysuccinimide ester)

Figure 7

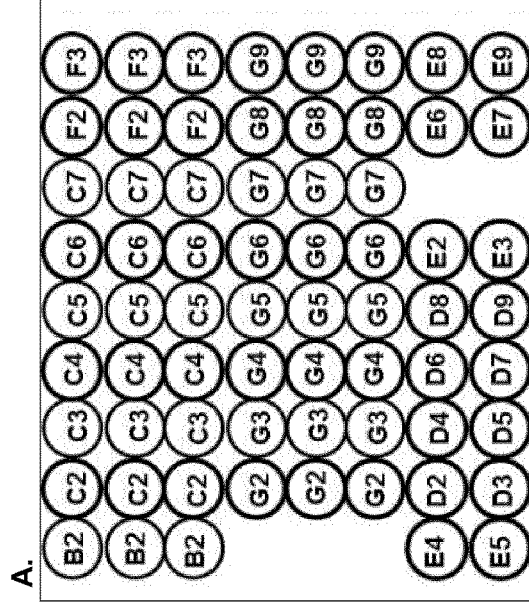

| | |
|---|---|
| C2 + C3: | hexasaccharide 23* Gal(β1-3)[Rha(α1-4)]GalA(α1-2)Rha(α1-2)Rha(α1-2)Rha(α1-1)aminopentanol; |
| C4+C5: | trisaccharide Rha(α1-2)Rha(α1-2)Rha(α1-1)aminopentanol; |
| C6+C7: | trisaccharide Gal(β1-3)[Rha(α1-4)]GalA(α1-2)aminopentanol; |
| D2+D3: | disaccharide Gal(β1-3)GalA(α1-1)aminopentanol; |
| D4+D5: | disaccharide Gal (β1-3)GalA(β1-1)aminopentanol; |
| D6+D7: | disaccharide Rha(α1-3)GalA(β1-1)aminopentanol; |
| D8+D9: | disaccharide Rha(α1-4)GalA(α1-1)aminopentanol; |
| E2+E3: | C. diff PSI pentasaccharide: Rha(α1-3)[Rha(α1-3)Glc(β1-4)]Glc(α1-2)Glc(α)linker; |
| E4+E5: | C. diff PSI disaccharide: Rha(α1-3)Glc(β)linker; |
| E6+E7: | monosaccharide: Rha(α)linker; |
| E8+E9: | S. pneumoniae type 5 pentasaccharide: L-PneNAc(α1-2)GlcA(β1-3)FucNAc(α1-3)D-FucNAc(β)Linker |
| B2: | Printing buffer; |
| F2: | CRM$_{197}$ (1μM); |
| F3: | BSA dimannose conjugate (1μM) |
| G2+G3: | Polysaccharide (C200, clade 1) corresponding to CPS from carbapenem-resistant strain K. pneumoniae strain 34 (CPS-K34) |
| G4+G5: | Polysaccharide (clade 2) corresponding to CPS from K. pneumoniae strain 36 (wzi29-K41) |
| G6+G7: | Polysaccharide (non typable) corresponding to CPS from K. pneumoniae strain 38 (wzi50) |
| G8: | K1 polysaccharide |
| G9: | K2 polysaccharide |

○ 200μM (synthetic glycans) 0.2 mg/mL (polysaccharides)
○ 100μM (synthetic glycans) 0.1 mg/mL (polysaccharides)

Figure 7 - continued
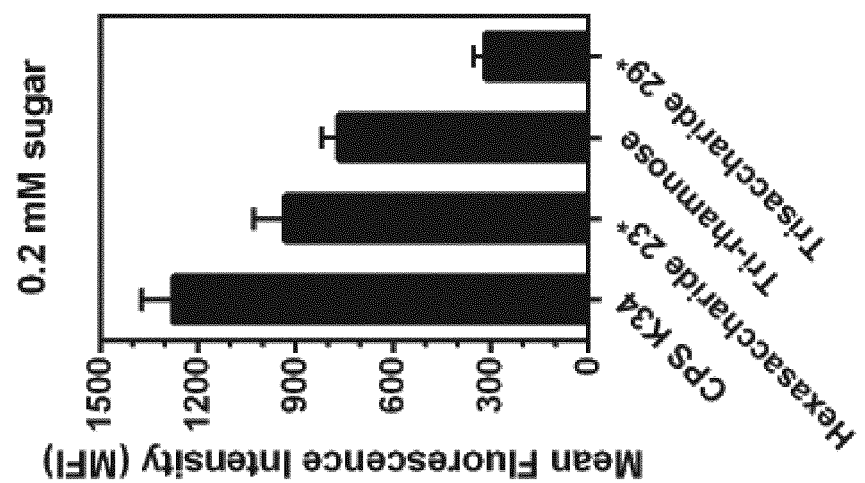
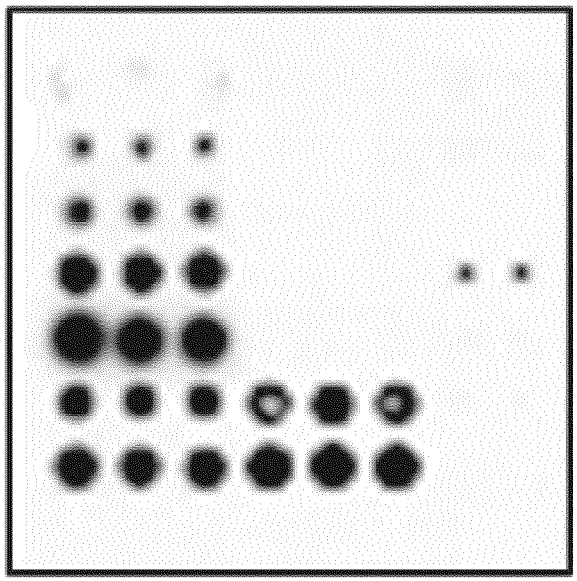

VACCINES AGAINST CARBAPENEM-RESISTANT *KLEBSIELLA PNEUMONIAE*

CROSS REFERENCE TO RELATED APPLICATIONS

This application is a U.S. National Phase Application of PCT International Application No. PCT/EP2016/056832, filed on Mar. 29, 2016, designating the United States of America and published in the English language, which claims priority to EP Application No. 15161528.3, filed Mar. 27, 2015. The disclosures of the above-referenced applications are hereby expressly incorporated by reference in their entireties.

FIELD OF THE INVENTION

The present invention relates to synthetic saccharides of general formula (I) that are related to carbapenem-resistant *Klebsiella pneumoniae* capsular polysaccharide and conjugates thereof. Said conjugates and pharmaceutical compositions containing said conjugates are useful for prevention and/or treatment of diseases associated with carbapenem-resistant *Klebsiella pneumoniae*. Furthermore, the synthetic saccharides of general formula (I) are useful as marker in immunological assays for detection of antibodies against carbapenem-resistant *Klebsiella pneumoniae* bacteria.

BACKGROUND OF THE INVENTION

*Klebsiella pneumoniae* is a gram-negative, facultative anaerobic, rod-shaped bacterium colonizing mostly of the respiratory and urinary tracts and causing *K. pneumoniae* infections (KPIs). KPI is the main cause of nosocomial infections, primarily affecting immunocompromised patients. In the last ten years, infections caused by *K. pneumoniae* are becoming an important challenge in healthcare settings due to the emergence of strains resistant to almost all available antimicrobial agents and their worldwide dissemination. Infections caused by carbapenem-resistant *Klebsiella pneumoniae* (CRKP) are responsible of high rates of morbidity and mortality. Thus, prevention of infections caused by CRKP is highly desirable, and vaccination of risk groups is the most cost-efficient and the most powerful means for avoiding future outbreaks of CRKP. Although, during the last 40 years, many attempts aiming at developing effective vaccines against *K. pneumoniae* were reported, up to present, there is no vaccine available for prophylactic or therapeutic use against carbapenem-resistant *Klebsiella pneumoniae* infections.

Like most bacteria, *K. pneumoniae* usually develop capsules composed of complex polysaccharides on the bacterial surface, which are highly immunogenic and nontoxic. In comparison with proteins, carbohydrates are evolutionarily more stable and have been exploited in a series of commonly employed vaccines. When covalently connected to a carrier protein, oligosaccharide antigens can elicit long lasting, T-cell-dependent protection.

The repeating unit of the capsular polysaccharide of carbapenem-resistant *K. pneumoniae* strains responsible of the outbreaks occurring in 2011 was elucidated (*Carbohydr. Res.* 2013, 369, 6-9) and consists of α-L-Rha-(1→4)-[β-D-Gal-(1→3)]-α-D-GalA-(1→2)-α-L-Rha-(1→2)-α-L-Rha-(1→2)-α-L-Rha (see FIG. 1).

The structure of the capsular repeating of *Klebsiella* K19 was also elucidated (*Carbohydr. Res.* 1986, 157, 13) and consists of a hexasaccharide repeating unit, which structurally differs from the saccharides claimed herein.

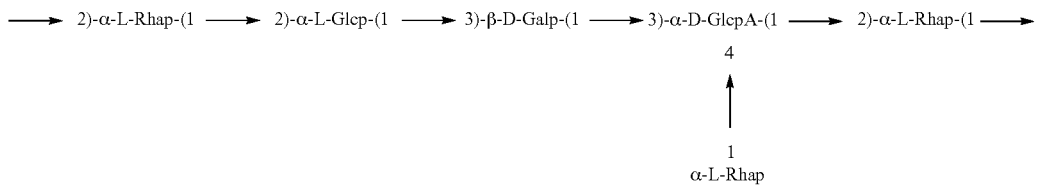

Repeating unit of capsular polysaccharide from *Klebsiella pneumoniae* K19

The capsular polysaccharide from *Klebsiella pneumoniae* K19, the capsular polysaccharide from *Klebsiella pneumoniae* K19 without the branching α-L-Rhap and the disaccharide αGlc1→3Gal-OH obtained via partial hydrolysis of said capsular polysaccharide were isolated. However, the isolated structures differ significantly from the saccharides claimed in the present patent application.

WO 9830224 A1 provides a composition for inhibiting IgE antibody production and response in vivo comprising a capsule component of a *Klebsiella oxytoca* and *Klebsiella pneumoniae*, or a fragment thereof produced by treatment of said capsule with an acid, a base or a reducing agent. Besides the fact that *Klebsiella oxytoca* and *Klebsiella pneumoniae* strain 19 have a capsular polysaccharide repeating unit which structurally differs from the saccharides provided in the present patent application, the isolated polysaccharides of WO 9830224 A1 are in fact mixtures of several polysaccharides having an average molecular weight superior to $1 \times 10^5$ i.e. significantly higher than the saccharides of the present invention.

EP 0735049 A2 provides a process for producing a polysaccharide having the following repeating unit:

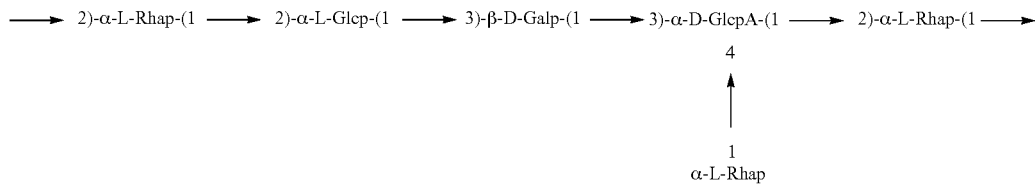

from polysaccharide-productive *Klebsiella oxytoca* TNM-3. The disclosed heteropolysaccharide having a molecular weight of 1000 to 10000000 is used as humectant, antistatic agent, film-forming agent or dispersant. The repeating unit of the polysaccharide disclosed by EP 0735049 A2 differs from the saccharidic structure of the compounds claimed in the present invention by the presence of an α-D-Glc residue instead of an α-L-Rha residue. Additionally, the isolated polysaccharides of EP 0735049 A2 are in fact mixtures of several polysaccharides having an average molecular weight of about $10^6$.

It is the objective of the present invention to provide a well-defined synthetic saccharide of general formula (I) that is related to carbapenem-resistant *Klebsiella pneumoniae* capsular polysaccharide and contains a protective immunogenic glycan epitope i.e. a glycan epitope that elicits antibodies which protect against diseases caused by carbapenem-resistant *Klebsiella pneumoniae*. Said saccharide can be conjugated to an immunogenic carrier to provide a conjugate and pharmaceutical composition thereof that are useful for prevention and/or treatment of diseases associated with carbapenem-resistant *Klebsiella pneumoniae*. Furthermore, the synthetic saccharide of general formula (I) is useful as marker in immunological assays for detection of antibodies against carbapenem-resistant *Klebsiella pneumoniae* bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 2 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminium salts (or mixtures thereof). Calcium salts include calcium phosphate. Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminium hydroxide and aluminium phosphate may be also used. The invention can use any of the "hydroxide" or "phosphate" adjuvants that are in general used as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from *Smilax ornata* (sarsaprilla), *Gypsophilla paniculata* (brides veil), and *Saponaria oficianalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS 7, QS 17, QS 18, QS2 1, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly($\alpha$-hydroxy acid), polyhydroxybutyric acid, polyorthoester, polyanhydride, polycaprolactone;

CD1d ligands, such as an $\alpha$-glycosylceramide, phytosphingosine-containing $\alpha$-glycosylceramides, OCH, KRN7000 [(2S,3S,4R)-1-O-($\alpha$-D-galactopyranosyl)-2-(N-hexacosanoylamino)-1,3,4-octadecanetriol], CRONY-101, 3"-sulfo-galactosyl-ceramide;

immunostimulatory oligonucleotides, such CpG motif containing ones (a dinucleotide sequence containing an unmethylated cytosine residue linked by a phosphate bond to a guanosine residue), or CO motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can:
  direct and optimize immune responses that are appropriate or desirable for the vaccine;
  enable mucosal delivery of vaccines, i.e. administration that results in contact of the vaccine with a mucosal surface such as buccal or gastric or lung epithelium and the associated lymphoid tissue;
  promote cell-mediated immune responses;
  enhance the immunogenicity of weaker immunogens, such as highly purified or recombinant antigens;
  reduce the amount of antigen or the frequency of immunization required to provide protective immunity; and
  improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:
  increasing the biological or immunologic half-life of antigens;
  improving antigen delivery to antigen-presenting cells (APCs), as well as antigen processing and presentation by the APCs e.g., by enabling antigen to cross endosomal membranes into the cytosol after ingestion of antigen-adjuvant complexes by APC;
  mimicking danger inducing signals from stressed or damaged cells, which serve to initiate an immune response;
  inducing the production of immunomodulatory cytokines;
  biasing the immune response towards a specific subset of the immune system; and—blocking the rapid dispersal of the antigen challenge.

Saccharides are known by the person skilled in the art as TI-2 (T cell independent-2) antigens and poor immunogens. Therefore, to produce a saccharide-based vaccine, said saccharides are conjugated to an immunogenic carrier to provide a conjugate, which presents an increased immunogenicity in comparison with the saccharide. In this context the term "immunogenic carrier" is defined as a structure, which is conjugated to the saccharide to form a conjugate that presents an increased immunity in comparison with the saccharide per se. Thus, the conjugation of the saccharides to the immunogenic carrier has as effect the stimulation of the immune response against said saccharide, without inducing an immune response against the said immunogenic carrier.

Hence, the present invention is directed to a synthetic saccharide of general formula (I)

$$V^*—[U_{x+2}—U_{x+1}—U_x]_n—V—O-L-NH_2 \quad (I)$$

wherein
x is an integer selected from 1, 2 and 3;
n is an integer selected from 1, 2 and 3;

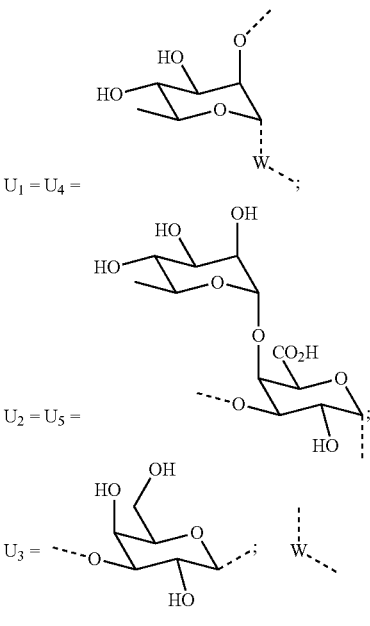

represents a bond,

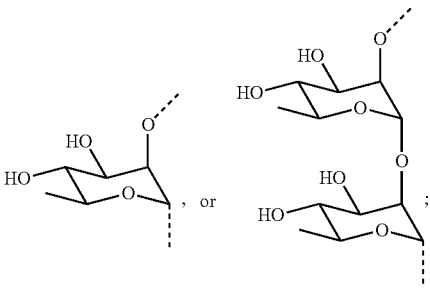

—V— represents a bond, —$U_{x+2}$— or —$U_{x+2}$—$U_{x+1}$—;
V*— represents H—, H—$U_x$—, or H—$U_{x+1}$—$U_x$—;

L represents a linker,
or a diastereoisomer or a pharmaceutically acceptable salt thereof.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-L-NH$_2$) and the NH$_2$-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the NH$_2$-group) consists of 2 to 6 atoms, these are preferably carbon atoms. In case the shortest chain consists of 4 to 8 atoms, the chain may contain 1 or 2 heteroatoms selected from O, N and S. In case the shortest chain consists of 9 to 14 atoms, the chain may contain 1, 2, 3, or 4 heteroatoms selected from O, N and S.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L- may also contain amide (—NH—CO—, —CO—NH—) and/or urea (—NH—CO—NH—) residues and preferably only one amide or urea residue. The linker may also contain substituents and preferably two substituents such as R$^{10}$ and R$^{11}$ or four substituents such as R$^{10}$, R$^{11}$, R$^{15}$ and R$^{14}$, which have the meanings as defined herein and which are preferably selected from: —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$.

In case the linker -L- is fluorinated, more than two substituents —F are preferred.

Preferably the linker -L- is selected from: —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$—O—CH$_2$—, —CH$_2$—O—(CH$_2$)$_2$—, —(CH$_2$)$_2$—O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$-;
wherein
-L$^a$- is selected from: —(CH$_2$)$_o$—, —(CF$_2$)$_o$—, —(CH$_2$—CH$_2$—O)$_o$—C$_2$H$_4$—, —(CH$_2$—CH$_2$—O)$_o$—CH$_2$—, —(CR$^{10}$R$^{11}$)$_o$—,

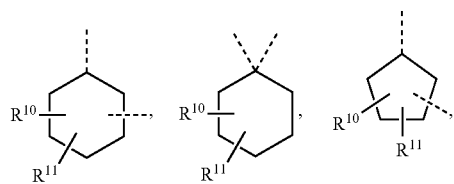

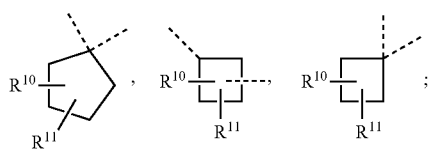

-L$^b$- and -L$^c$- are independently of each other selected from:
—O—, —NH—C(O)—NH—, —NH—C(S)—NH—, —NH—C(O)—, —C(O)—NH—, —NH—C(O)—O—, —NR$^9$—, —NR$^{18}$—, —SO$_2$—,

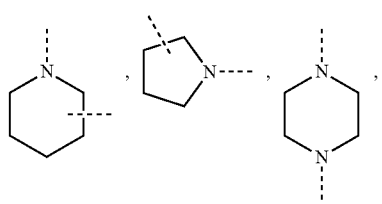

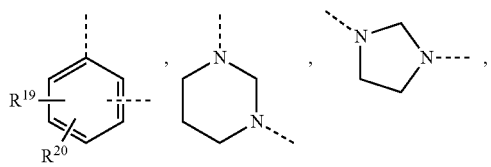

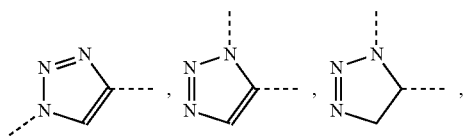

-L$^d$- represents —(CH$_2$)$_q$—, —(CF$_2$)$_q$—, —(CR$^{12}$R$^{13}$)$_q$—, —(CH$_2$—CH$_2$—O)$_q$—C$_2$H$_4$—, —(CH$_2$—CH$_2$—O)$_q$—CH$_2$—,

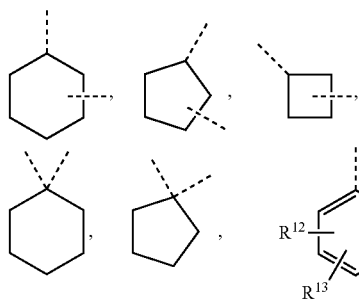

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

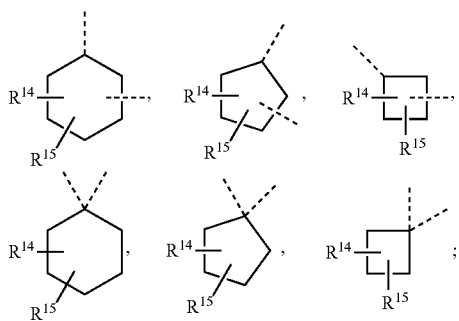

$R^9$ and $R^{18}$ are independently of each other selected from: —$CH_3$, —$C_2H_5$, —$C_3H_7$ and —$C(O)CH_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —$C(O)$—$NH_2$, —$SCH_3$, —$SC_2H_5$, —$NHC(O)CH_3$, —$N(CH_3)_2$ and —$N(C_2H_5)_2$;

o, q, p1 and p2 are independently of each other an integer selected from 1, 2, 3, 4, 5, 6, 7, 8, 9, and 10.

The saccharides of the present invention bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

It is clear for the skilled person in the art of carbohydrate chemistry that the saccharides of general (I) are not containing —O—O— bonds and or sugar fragments ($U_x$, $U_{x+1}$, $U_{x+2}$) connected or bound to each other via their anomeric or C-1 carbons. It is also clear for the person skilled in the art that the stereochemistry of the glycosidic bond is defined by the stereochemistry indicated for the anomeric centre of the sugar fragment $U_x$, $U_{x+1}$ and $U_{x+2}$ in the general formula.

Surprisingly, it was found that a saccharide of general formula (I) contains an immunogenic protective epitope and is able to induce a protective immune response against carbapenem-resistant K. pneumoniae bacteria in a human and/or animal host. The saccharide of general formula (I) elicits antibodies that are cross-reacting with the carbapenem-resistant K. pneumoniae bacteria capsular polysaccharide, recognize specifically carbapenem-resistant K. pneumoniae bacteria and opsonize them for killing by phagocytes.

The saccharides of the present invention overcome all the problems associated with the saccharides produced from bacterial sources and conjugates thereof in terms of purity and easiness of production. It is well known that the isolation and purification of pure saccharides of defined length and structure from capsular polysaccharides of pathogenic bacteria is a tedious and sometimes not feasible process. Firstly, the production of capsular polysaccharides requires optimization of the growth conditions. Secondly, depolymerization conditions under which the structural integrity of the constituting monosaccharides is maintained need to be found. Finally, purification conditions enabling the isolation of the pure saccharide of defined length and structure need to be determined. Besides usual contaminants, such as cellular polysaccharides, nucleic acids and proteins, also the undesired saccharides obtained through the depolymerization process, must be excluded. Thus, the production of pure saccharides of defined structure and length from bacterial sources is a tedious, almost impossible process.

Preferred are synthetic saccharides of general formula (I), wherein

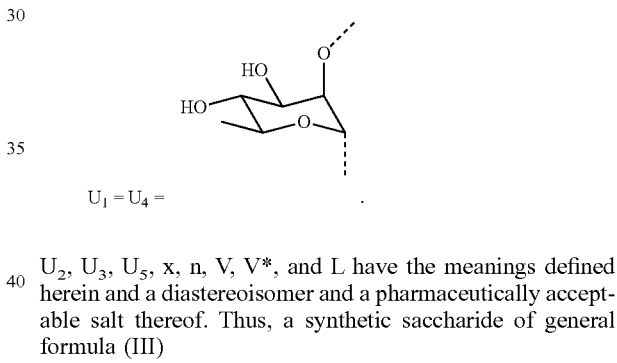

$U_2$, $U_3$, $U_5$, x, n, V, V*, and L have the meanings defined herein and a diastereoisomer and a pharmaceutically acceptable salt thereof. Thus, a synthetic saccharide of general formula (III)

$$V^*—[U_{x+2}—U_{x+1}—U_x]_n—V—O-L-NH_2 \qquad (III)$$

wherein
x is an integer selected from 1, 2 and 3;
n is an integer selected from 1, 2 and 3;

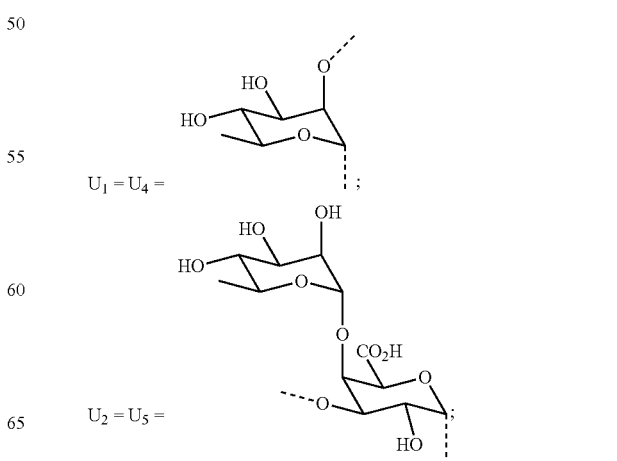

-continued

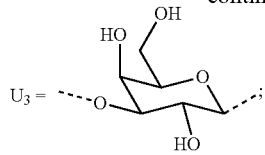

—V— represents a bond, —$U_{x+2}$— or —$U_{x+2}$—$U_{x+1}$—;
V*— represents H—, H—$U_x$—, or H—$U_{x+1}$—$U_x$—;
L represents a linker,
or a diastereoisomer or a pharmaceutically acceptable salt thereof.

Hence, within the scope of the present invention falls also a synthetic saccharide of general formula (III-a)

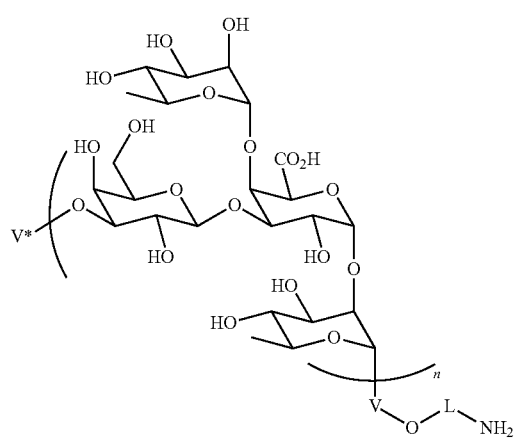

III-a wherein
—V— represents a bond, —$U_3$— or —$U_3$—$U_2$—;
V*— represents H—, H—$U_1$—, or H—$U_2$—$U_1$—;
L represents a linker,
n is an integer selected from 1, 2 and 3;

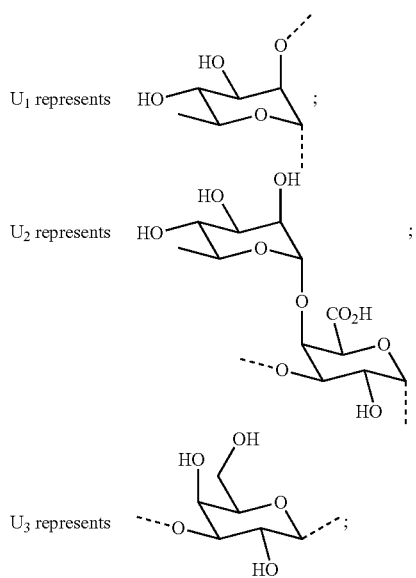

and a synthetic saccharide of general formula (III-b)

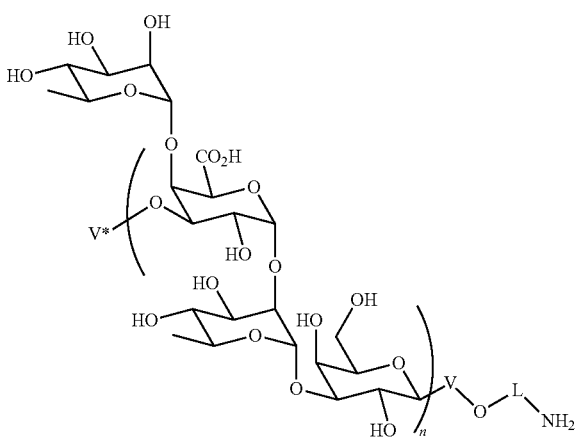

III-b wherein
—V— represents a bond, —$U_5$— or —$U_5$—$U_4$—;
V*— represents H—, H—$U_3$—, or H—$U_4$—$U_3$—;
L represents a linker;
n is an integer selected from 1, 2 and 3;

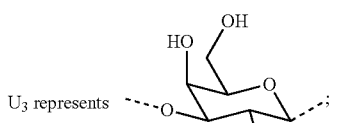

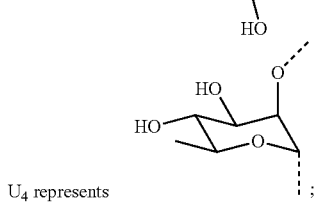

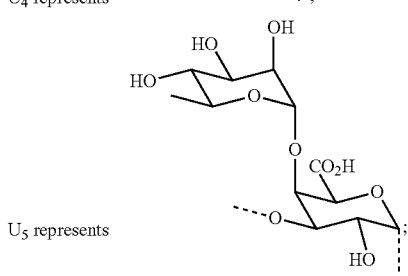

and a synthetic saccharide of general formula (III-c)

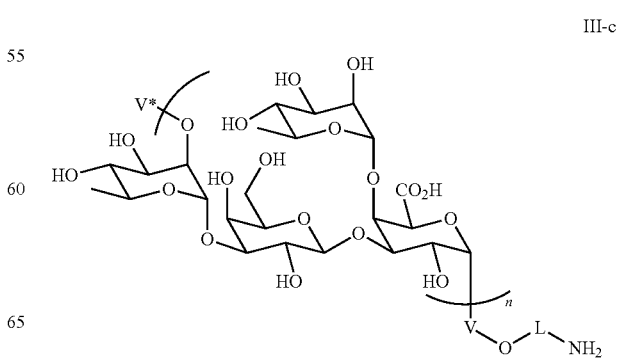

III-c wherein
—V— represents a bond, —$U_4$— or —$U_4$—$U_3$—;
V*— represents H—, H—$U_2$—, or H—$U_3$—$U_2$—;
L represents a linker;
n is an integer selected from 1, 2 and 3;

$U_2$ represents 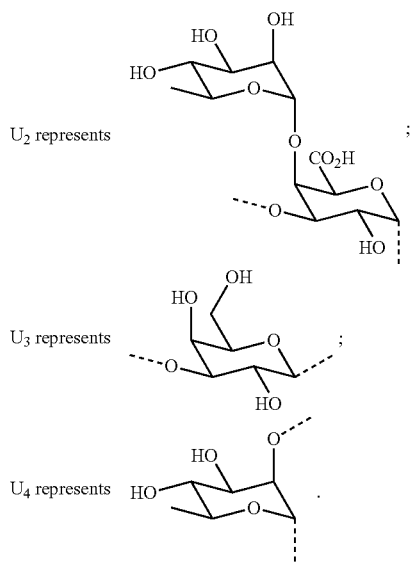

$U_3$ represents $U_4$ represents 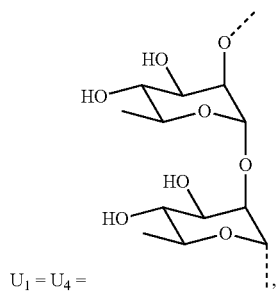

An embodiment of the present invention refers to a saccharide of general formula (I), wherein $U_1 = U_4 =$ 

$U_2$, $U_3$, $U_5$, x, n, V, V*, and L have the meanings defined herein, and a diastereoisomer and a pharmaceutically acceptable salt thereof.

Hence, a synthetic saccharide of general formula (IV)

$$V^*—[U_{x+2}—U_{x+1}—U_x]_n—V—O\text{-}L\text{-}NH_2 \quad (IV)$$

wherein
x is an integer selected from 1, 2 and 3;
n is an integer selected from 1, 2 and 3;

$U_1 = U_4 =$ 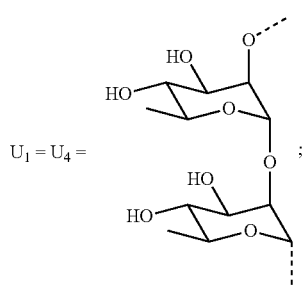

$U_2 = U_5 =$ 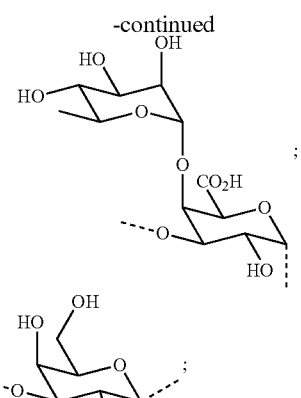

$U_3 =$

—V— represents a bond, —$U_{x+2}$— or —$U_{x+2}$—$U_{x+1}$—;
V*— represents H—, H—$U_x$—, or H—$U_{x+1}$—$U_x$—;
L represents a linker,
or a diastereoisomer or a pharmaceutically acceptable salt thereof is also preferred.

Thus, a synthetic saccharide of general formula (IV-a)

IV-a

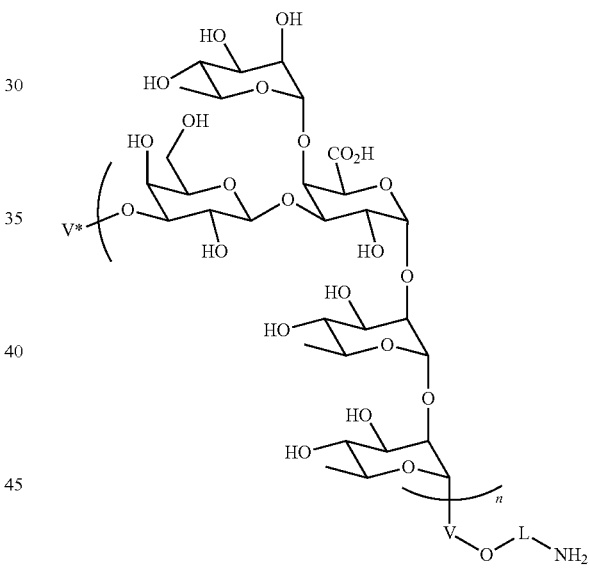

wherein
—V— represents a bond, —$U_3$— or —$U_3$—$U_2$—;
V*— represents H—, H—$U_1$—, or H—$U_2$—$U_1$—;
L represents a linker,
n is an integer selected from 1, 2 and 3;

$U_1$ represents 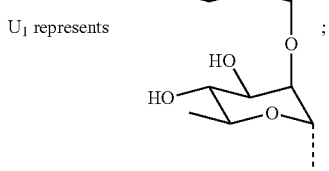

-continued

U₂ represents 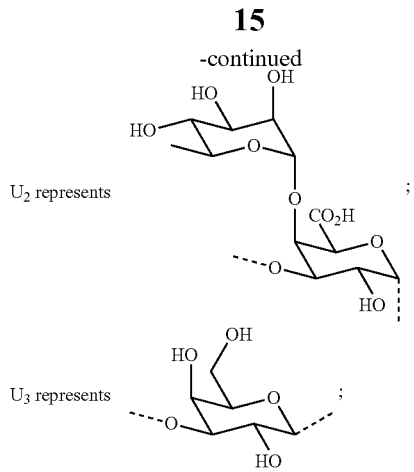;

U₃ represents ;

and a synthetic saccharide of general formula (IV-b)

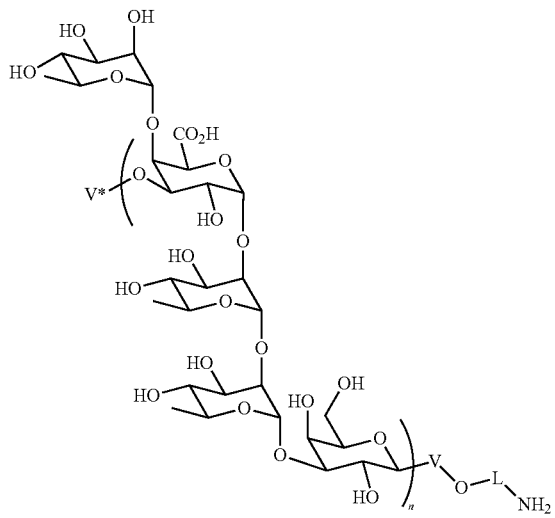

wherein
—V— represents a bond, —U₅— or —U₅—U₄—;
V*— represents H—, H—U₃—, or H—U₄—U₃—;
L represents a linker;
n is an integer selected from 1, 2 and 3;

U₃ represents ;

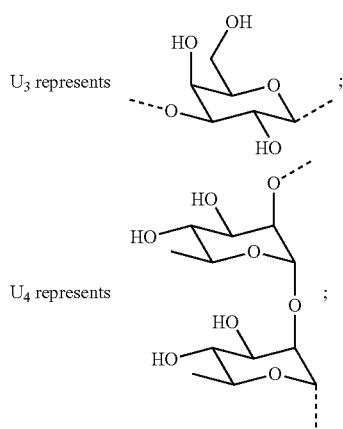

U₄ represents ;

-continued

U₅ represents 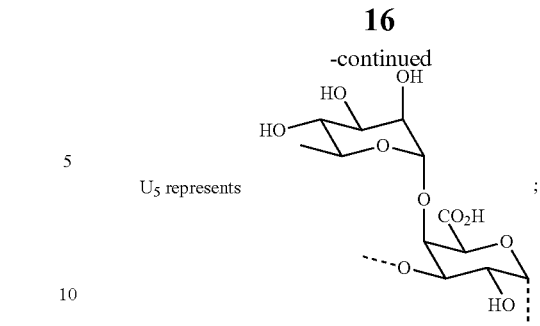;

and a synthetic saccharide of general formula (IV-c)

IV-c

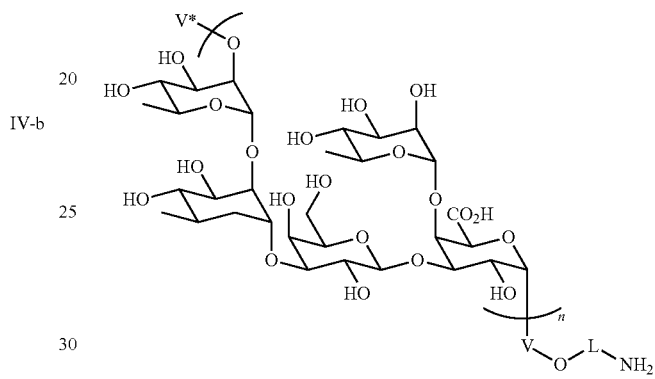

wherein
—V— represents a bond, —U₄— or —U₄—U₃—;
V*— represents H—, H—U₂—, or H—U₃—U₂—;
L represents a linker;
n is an integer selected from 1, 2 and 3;

U₂ represents 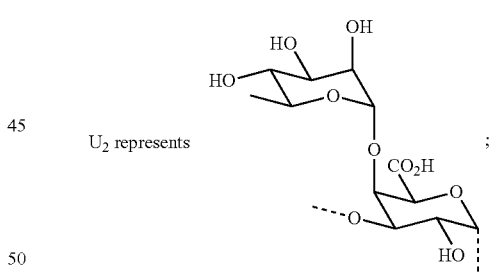;

U₃ represents ;

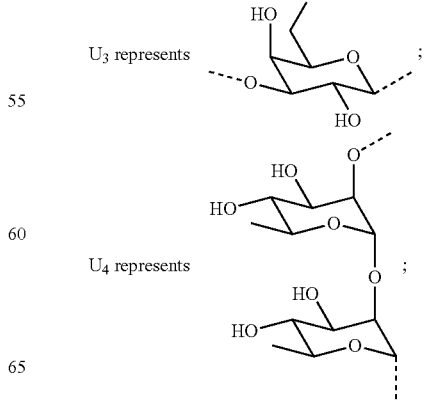

U₄ represents ;

Another embodiment of the present invention is directed to a synthetic saccharide of general formula (I) wherein

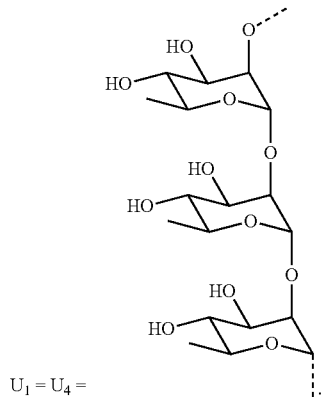

$U_1 = U_4 =$ $U_2$, $U_3$, $U_5$, x, n, V, V*, and L have the meanings defined herein, and a diastereoisomer and a pharmaceutically acceptable salt thereof. Hence, a further preferred synthetic saccharide according to the present invention is a saccharide of general formula (V)

$$V^*—[U_{x+2}—U_{x+1}—U_x]_n—V—O\text{-}L\text{-}NH_2 \qquad (V)$$

wherein
x is an integer selected from 1, 2 and 3;
n is an integer selected from 1, 2 and 3;

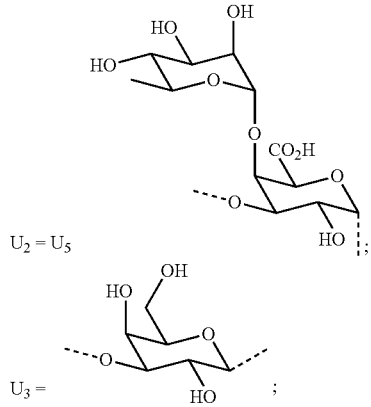

—V— represents a bond, —$U_{x+2}$— or —$U_{x+2}$—$U_{x+1}$—;
V*— represents H—, H—$U_x$—, or H—$U_{x+1}$—$U_x$—;
L represents a linker, or a diastereoisomer or a pharmaceutically acceptable salt thereof.

Therefore, under the scope of the present invention falls also a synthetic saccharide of general formula (V-a)

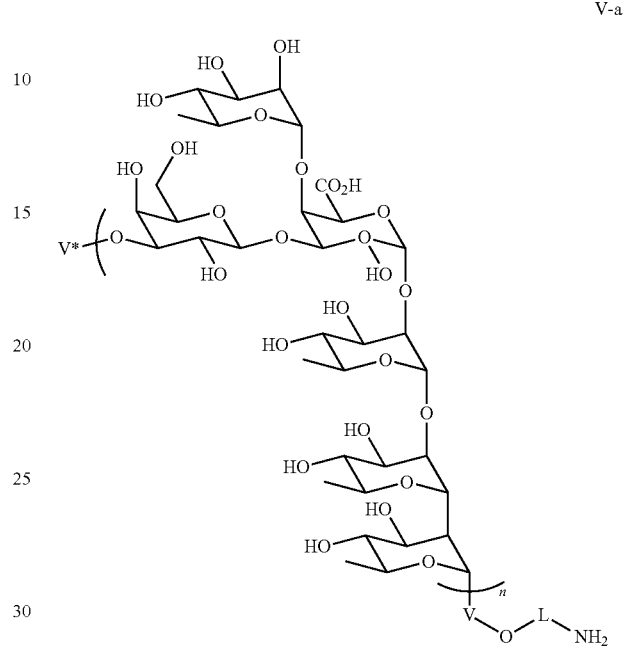

V-a wherein
—V— represents a bond, —$U_3$— or —$U_3$—$U_2$—;
V*— represents H—, H—$U_1$—, or H—$U_2$—$U_1$—;
L represents a linker,
n is an integer selected from 1, 2 and 3;

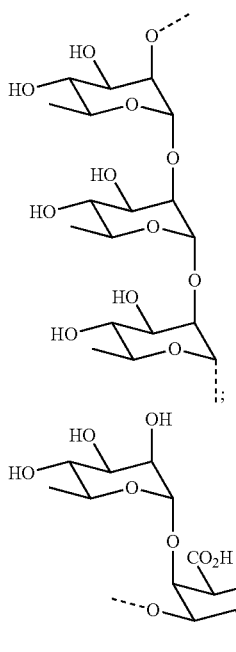

$U_1$ represents $U_2$ represents

19

-continued $U_3$ represents 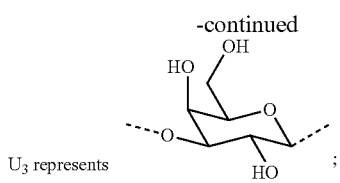 ;

and a synthetic saccharide of general formula (V-b)

V-b

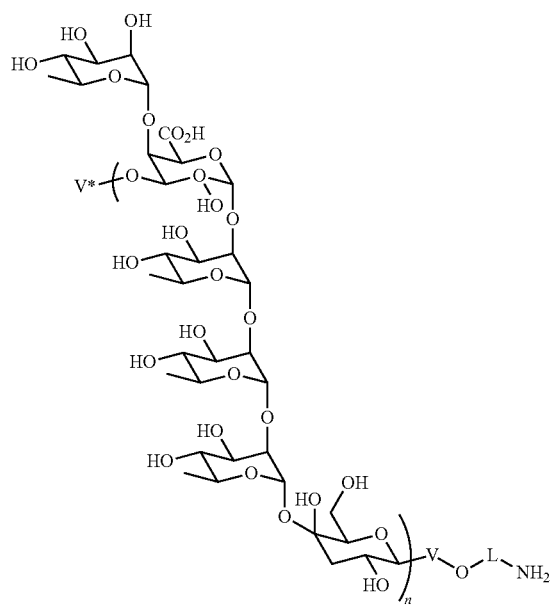

wherein

—V— represents a bond, —$U_5$— or —$U_5$—$U_4$—;
V*— represents H—, H—$U_3$—, or H—$U_4$—$U_3$—;
L represents a linker;
n is an integer selected from 1, 2 and 3;

$U_3$ represents $U_4$ represents 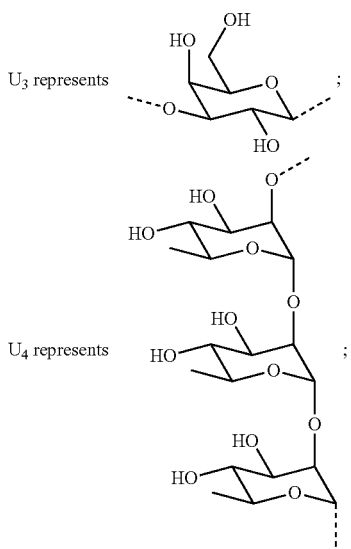 ;

20

-continued $U_5$ represents 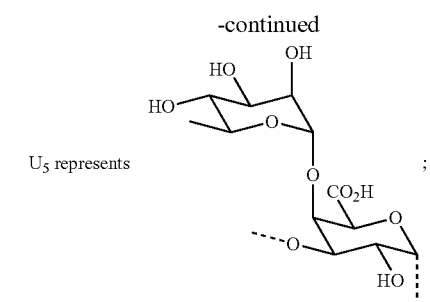 ;

and a synthetic saccharide of general formula (V-c)

V-c

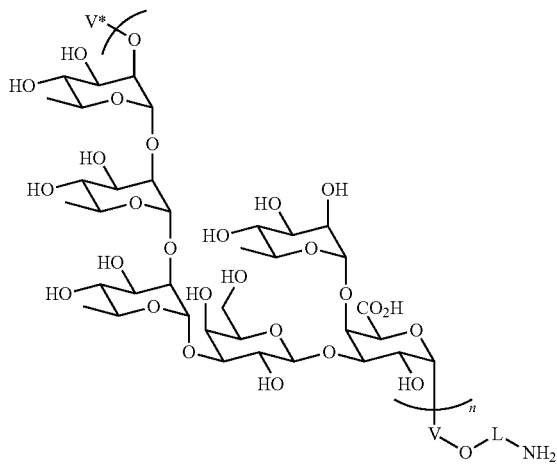

wherein

—V— represents a bond, —$U_4$— or —$U_4$—$U_3$—;
V*— represents H—, H—$U_2$—, or H—$U_3$—$U_2$—;
L represents a linker;
n is an integer selected from 1, 2 and 3;

$U_2$ represents 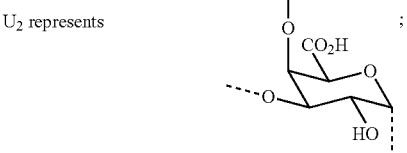 ;

$U_3$ represents 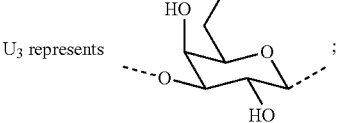 ;

$U_4$ represents 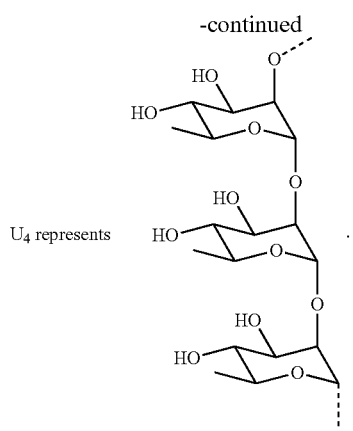

Also preferred is a synthetic saccharide of general formula (II)

(II)
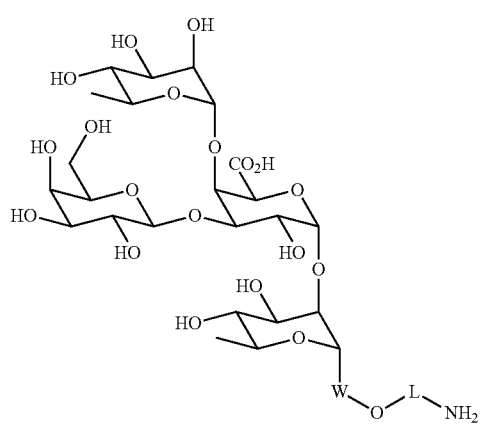

wherein

and L have the meanings defined herein, and a diastereoisomer and a pharmaceutically acceptable salt thereof.

Hence, synthetic saccharides of general formula (II-a), (II-b) or (II-c), wherein L has the meaning defined herein are also preferred.

II-a
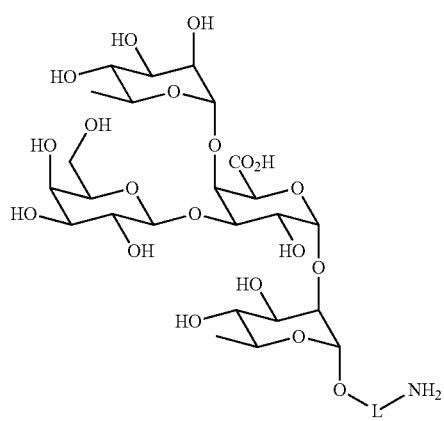

II-b
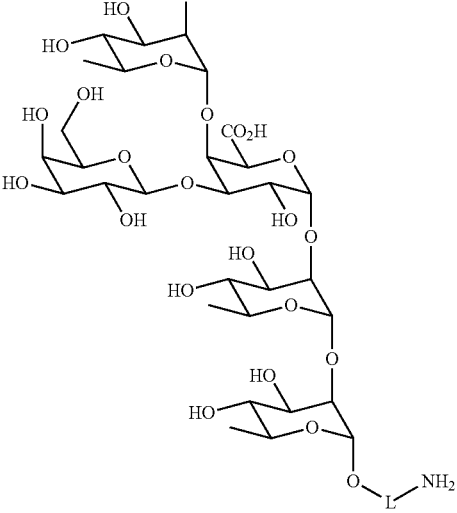

II-c
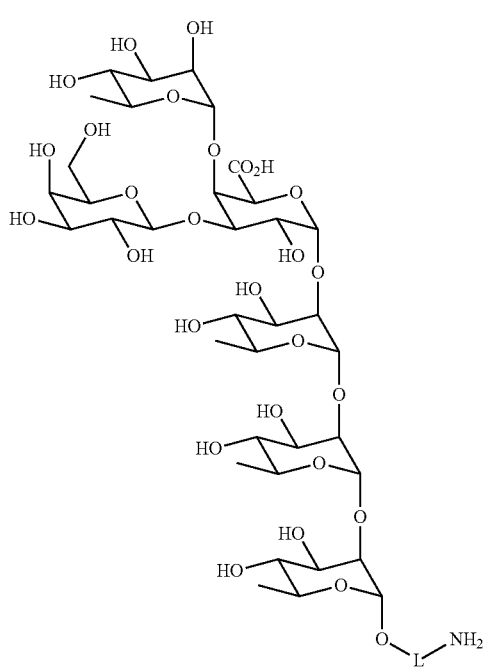

Preferably the linker -L- is selected from: -$L^a$-, -$L^a$-$L^e$-, -$L^a$-$L^b$-$L^e$-, -$L^a$-$L^d$-$L^e$-;
wherein
-$L^a$- is selected from: —$(CH_2)_o$—, —$(CH_2-CH_2-O)_o$—$C_2H_4$—, —$(CH_2-CH_2-O)_o$—$CH_2$;
-$L^b$- represents —O—;
-$L^d$- is selected from: —$(CH_2)_q$—, —$(CF_2)_q$—, —$(CH_2-CH_2-O)_q$—$C_2H_4$—, and —$(CH_2-CH_2-O)_q$—$CH_2$—;
-$L^e$- is selected from: —$(CH_2)_{p1}$—, —$(CF_2)_{p1}$—, —$C_2H_4-(O-CH_2-CH_2)_{p1}$—, —$CH_2-(O-CH_2-CH_2)_{p1}$— and —$(CH_2)_{p1}$—O—$(CH_2)_{p2}$—;
and o, q, p1 and p2 are independently of each other an integer selected from 1, 2, 3, 4, 5, and 6.

Therefore, a saccharide of general formula (I), (II), (II-a), (II-b), (II-c), (III), (III-a), (III-b), (III-c), (IV), (IV-a), (IV-b), (IV-c), (V), (V-a), (V-b) or (V-c) wherein -L- is selected from: -$L^a$-, -$L^a$-$L^e$-, -$L^a$-$L^b$-$L^e$-, and -$L^a$-$L^d$-$L^e$-;

-$L^a$- is selected from: —$(CH_2)_o$—, —$(CH_2$—$CH_2$—$O)_o$—$C_2H_4$—, —$(CH_2$—$CH_2$—$O)_o$—$CH_2$;

-$L^b$- represents —O—;

-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;

and o, q, p1 and p2 are independently of each other an integer selected from 1, 2, 3, 4, 5, and 6 is especially preferred.

In the most preferred embodiment, -L- represents —$(CH_2)_o$— and o is an integer selected from 2, 3, 4, 5 and 6. Hence, an especially preferred synthetic saccharide is a saccharide of general formula (I), (II), (II-a), (II-b), (II-c), (III), (III-a), (III-b), (III-c), (IV), (IV-a), (IV-b), (IV-c), (V), (V-a), (V-b) or (V-c), wherein -L- represents —$(CH_2)_o$— and o is an integer selected from 2, 3, 4, 5 and 6.

Especially preferred is a saccharide of general formula (I), (III), (III-a), (III-b), (III-c), (IV), (IV-a), (IV-b), (IV-c), (V), (V-a), (V-b) or (V-c), wherein n represents 1. Thus, an especially preferred saccharide is a saccharide of general formula (I), (III), (III-a), (III-b), (III-c), (IV), (IV-a), (IV-b), (IV-c), (V), (V-a), (V-b) or (V-c), wherein n represents 1 and -L- represents —$(CH_2)_o$— with o being an integer selected from 2, 3, 4, 5 and 6.

In yet another preferred embodiment, the saccharide according to the present invention is selected from the group consisting of:

5-amino-pentanyl α-L-rhamnopyranosyl-(1→4)-[β-D-galactosyl-(1→3)]-α-D-galactopyranosyluronic acid-(1→2)-α-L-rhamnopyranoside;

2-(2-aminoethoxy)ethoxyl α-L-rhamnopyranosyl-(1→4)-[β-D-galactosyl-(1→3)]-α-D-galactopyranosyluronic acid-(1→2)-α-L-rhamnopyranoside;

2-amino pentanyl α-L-rhamnopyranosyl-(1→4)-[β-D-galactosyl-(1→3)]-α-D-galactopyranosyluronic acid-(1→2)-α-L-rhamnopyranosyl-(1→2)-α-L-rhamnopyranosyl-(1→2)-α-L-rhamnopyranoside;

4-amino pentanyl α-L-rhamnopyranosyl-(1→4)-[β-D-galactopyranosyl-(1→3)]-α-D-galactopyranosyluronic acid-(1→2)-α-L-rhamnopyranosyl-(1→2)-α-L-rhamnopyranosyl-(1→2)-α-L-rhamnopyranoside;

2-amino pentanyl α-L-rhamnopyranosyl-(1→4)-[β-D-galactopyranosyl-(1→3)]-α-D-galactopyranosyluronic acid-(1→2)-α-L-rhamnopyranosyl-(1→2)-α-L-rhamnopyranoside; and 3-amino-2,2-difluoropropoxyl α-L-rhamnopyranosyl-(1→4)-[β-D-galactopyranosyl-(1→3)]-α-D-galactopyranosyluronic acid-(1→2)-α-L-rhamnopyranosyl-(1→2)-α-L-rhamnopyranoside.

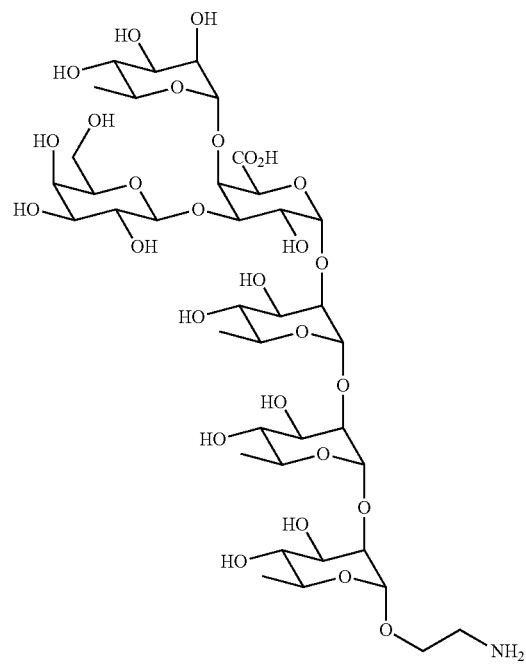

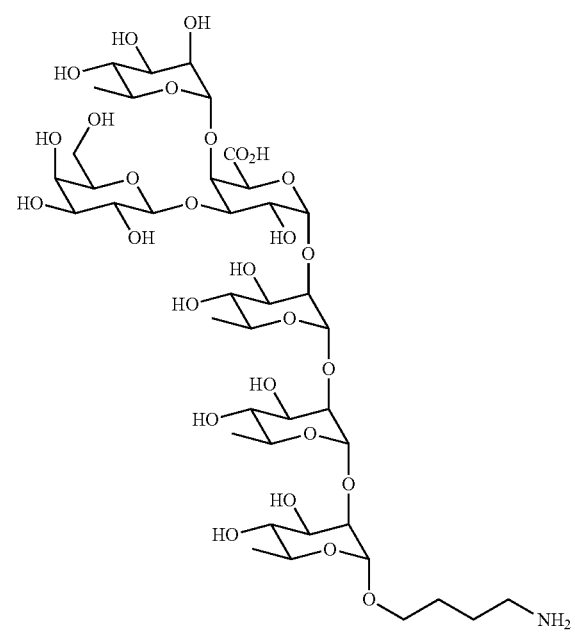

2-amino ethanyl α-L-Rha-(1→4)-[β-D- Gal-(1→3)]-α-D-GalA(1→2)-α-L- Rha(1→2)-α-L-Rha(1→2)-α-L- Rhamnopyranoside;

4-amino pentanyl α-L-Rha-(1→4)-[β-D-Gal-(1→3)]-α-D-GalA(1→2)-α-L-Rha(1→2)-α-L-Rha(1→2)-α-L-Rhamnopyranoside;

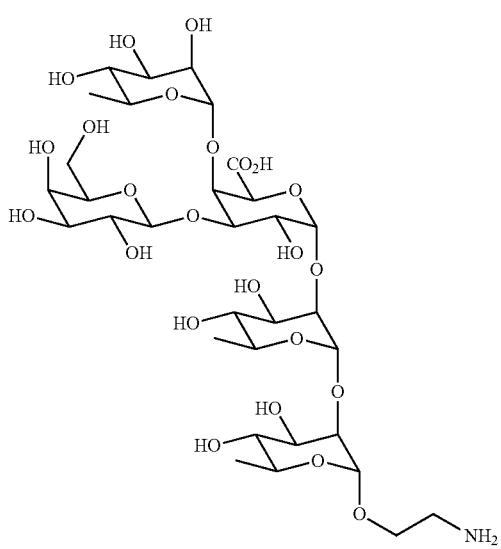

2-amino ethanyl α-L-Rha-(1→4)-[β-D- Gal-(1→3)]-α-D-GalA(1→2)-α-L- Rha(1→2)-α-L-Rhamnopyranoside;

3-amino-2,2-difluoropropoxyl α-L-Rha-(1→4)-[β-D-Gal-(1→3)]-α-D-GalA(1→2)-α-L-Rha(1→2)-α-L-Rhamnopyranoside,

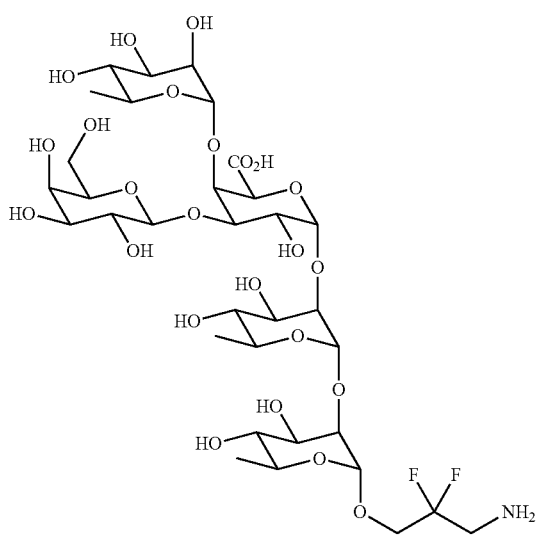

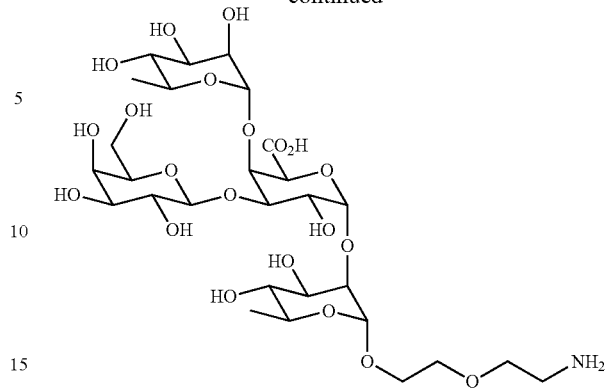

5-amino-pentanyl α-L-Rha-(1→4)-[β-D- Gal-(1→3)]-α-D-GalA(1→2)-α-L- Rhamnopyranoside; 2-(2-aminoethoxy) ethoxyl α-L-Rha-(1→4)-[β-D-Gal-(1→3)]-α-D-GalA(1→2)-α-L-Rhamnopyranoside;

Chemical Synthesis

Another aspect of the present invention is directed to a synthetic method comprising the steps:
reacting compound 7 of formula:

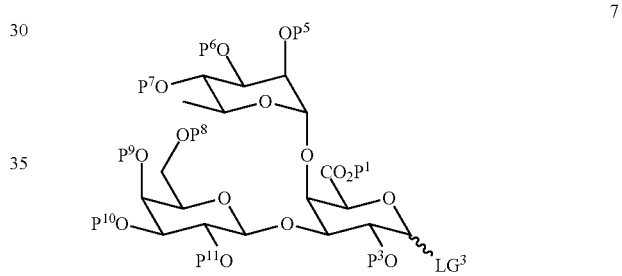

wherein $P^1$, $P^3$, $P^5$-$P^{11}$ represent protecting groups and $LG^3$ represents a leaving group selected from:

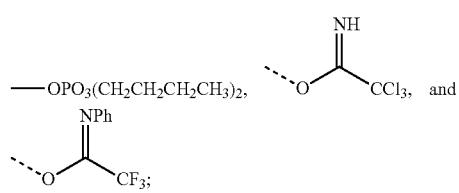

with compound 10 of formula:

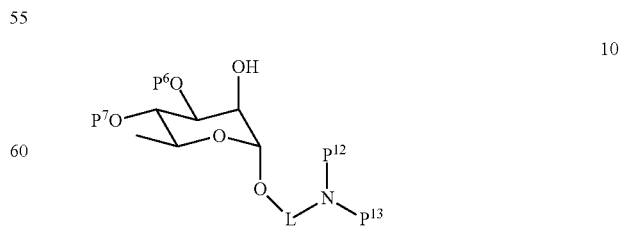

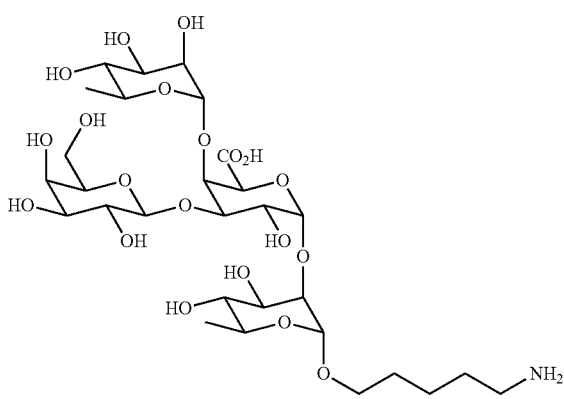

wherein $P^6$, $P^7$, $P^{12}$ and $P^{13}$ represent protecting groups and L has the meaning defined herein to provide compound 15 of formula:

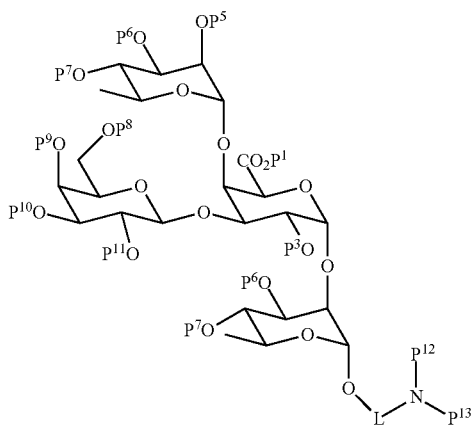

15 wherein $P^1$, $P^3$, $P^5$-$P^{13}$ represent protecting groups and L has the meaning defined herein;
or
with compound 12 of formula:

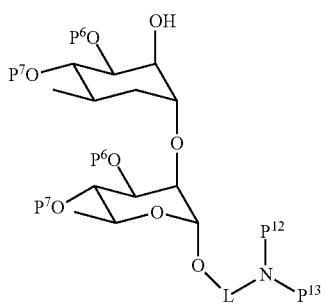

12 wherein $P^6$, $P^7$, $P^{12}$ and $P^{13}$ represent protecting groups and L has the meaning defined herein to provide compound 16 of formula:

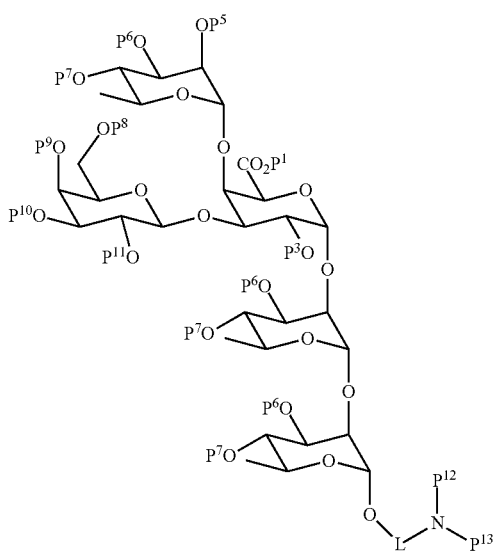

16 wherein $P^1$, $P^3$, $P^5$-$P^{13}$ represent protecting groups and L has the meaning defined herein;
or
with compound 14 of formula:

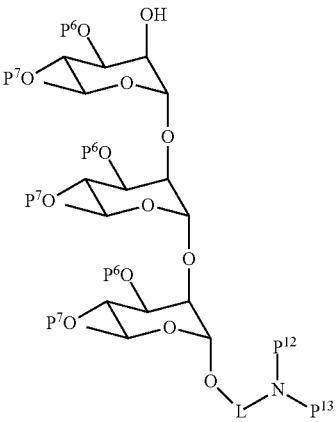

14 wherein $P^6$, $P^7$, $P^{12}$ and $P^{13}$ represent protecting groups and L has the meaning defined herein to provide compound 17 of formula:

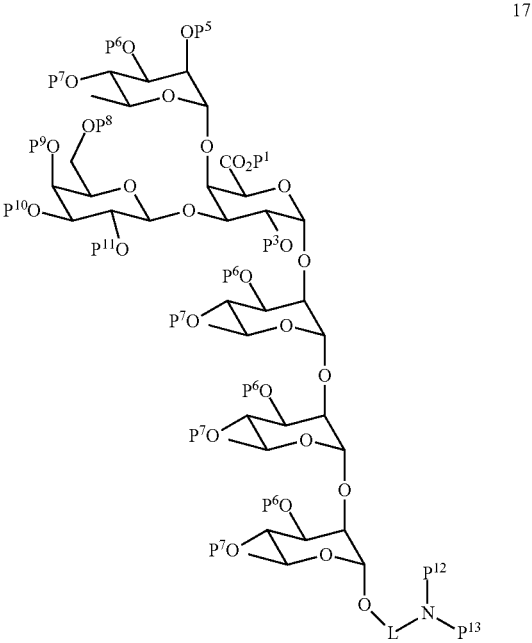

17 wherein $P^1$, $P^3$, $P^5$-$P^{13}$ represent protecting groups and L has the meaning defined herein.

The synthetic method described herein provides the key intermediates 15, 16 and 17 presenting the α-stereochemistry at the new formed stereocenter in at least 80% yield, preferably 85% yield, and even more preferably 90% yield.

Another embodiment of the present invention is directed to a method of synthesis of a saccharide of general formula (II)

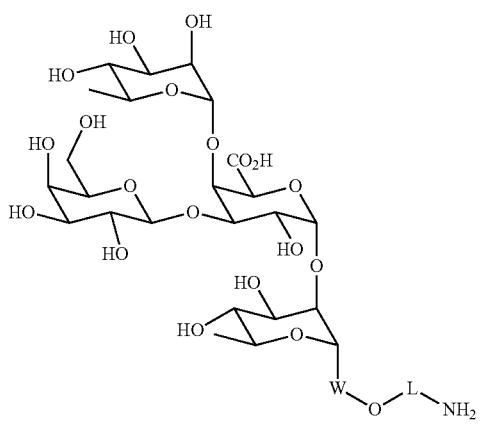

(II)

wherein

and L have the meanings as defined herein,
comprising the following steps:
A) reacting a compound 1 of the formula:

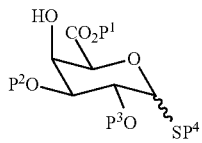

1 wherein P¹-P³ represent protecting groups and P⁴ is selected from: —CH₃,

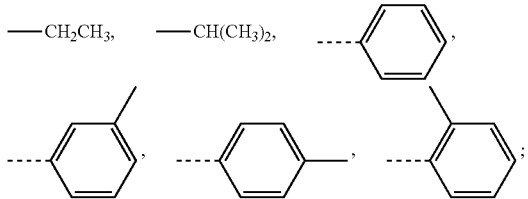

with a compound 2 of the formula:

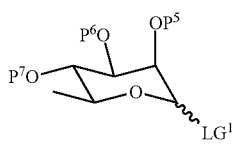

2 wherein P⁵-P⁷ represent protecting groups and LG¹ represents a leaving group selected from:

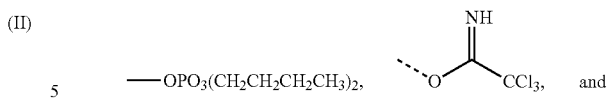

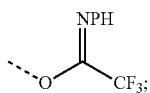

to provide a compound 3 of formula:

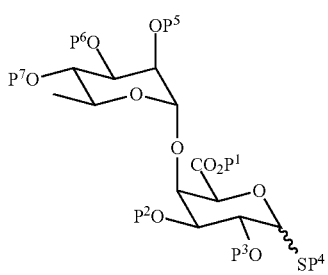

3 wherein P¹-P³, P⁴-P⁷ represent protecting groups and P⁴ is selected from:

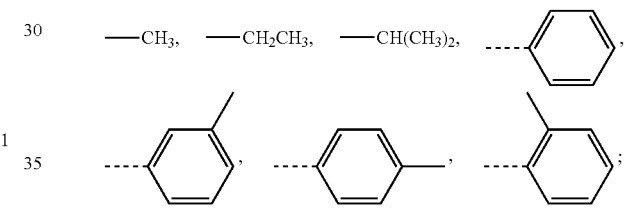

and
performing selective removal of protective group P² on compound 3 to obtain compound 4 of formula:

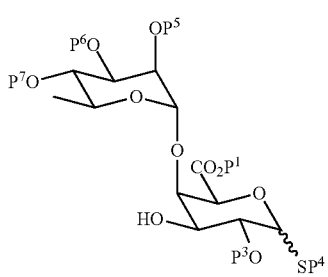

4 wherein P¹, P³, P⁴-P⁷ represent protecting groups and P⁴ is selected from:

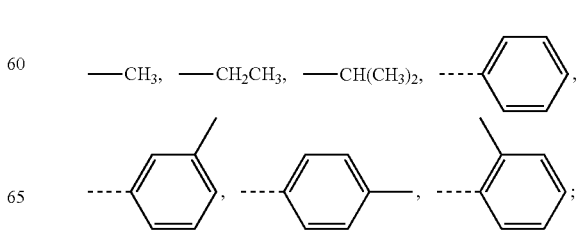

and
reacting compound 4 with compound 5 of formula:

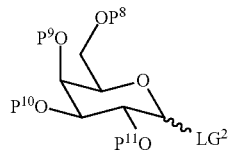

5 wherein $P^8$-$P^{11}$ represent protecting groups and $LG^2$ represents a leaving group selected from:

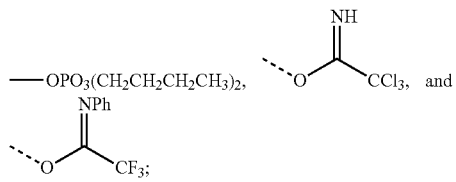

to obtain compound 6 of formula:

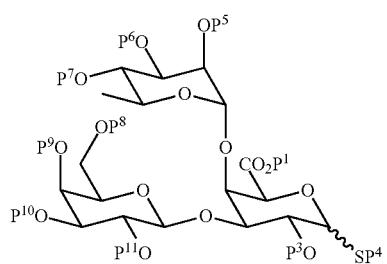

6 wherein $P^1$, $P^3$, $P^5$-$P^{11}$ represent protecting groups and $P^4$ is selected from:

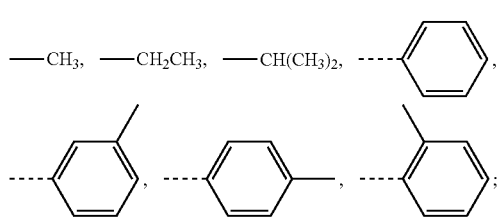

and
converting compound 6 to compound 7 of formula:

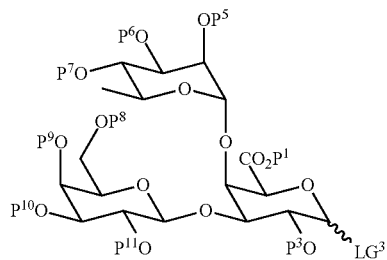

7 wherein $P^1$, $P^3$, $P^5$-$P^{11}$ represent protecting groups and $LG^3$ represents a leaving group selected from:

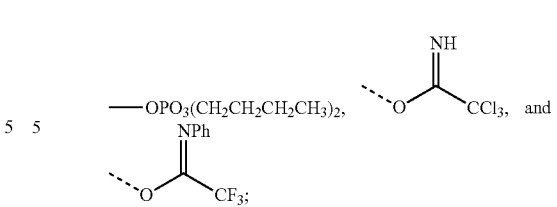

and
B1) Reacting compound 2 with compound 8 of formula:

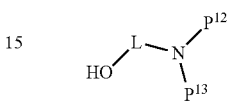

8 wherein $P^{12}$ and $P^{13}$ represent protecting groups to provide compound 9 of formula:

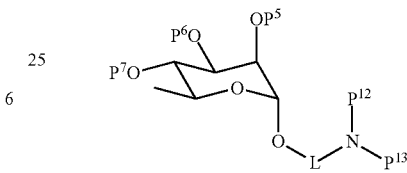

9 wherein $P^5$-$P^7$, $P^{12}$ and $P^{13}$ represent protecting groups; and performing selective removal of protective group $P^5$ on compound 9 to provide compound 10 of formula:

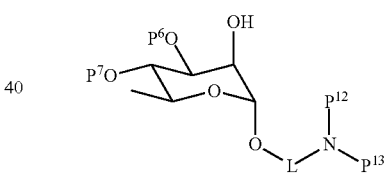

10 wherein $P^6$, $P^7$, $P^{12}$ and $P^{13}$ represent protecting groups; and

B2) reacting compound 2 with compound 10 to obtain compound 11 of formula:

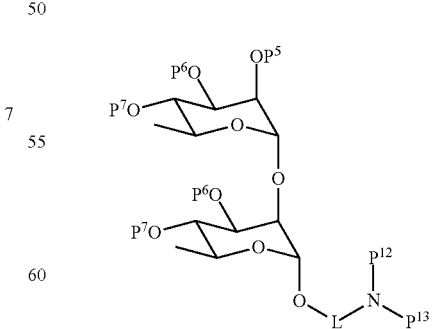

11 wherein $P^5$-$P^7$, $P^{12}$ and $P^{13}$ represent protecting groups; and performing selective removal of protective group $P^5$ on compound 11 to provide compound 12 of formula:

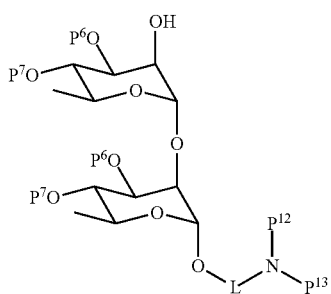

12 wherein $P^6$, $P^7$, $P^{12}$ and $P^{13}$ represent protecting groups;

and

B3) reacting compound 2 with compound 12 to obtain compound 13 of formula:

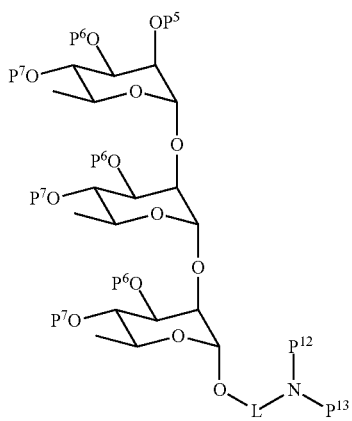

13 wherein $P^5$-$P^7$, $P^{12}$ and $P^{13}$ represent protecting groups;

and performing selective removal of protective group $P^5$ on compound 13 to provide compound 14 of formula:

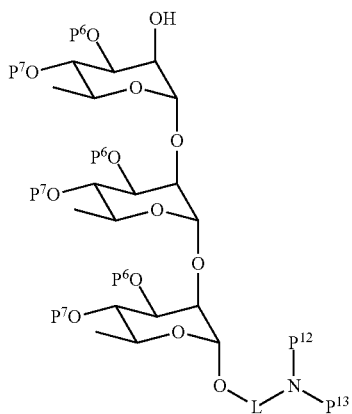

14 wherein $P^6$, $P^7$, $P^{12}$ and $P^{13}$ represent protecting groups;

and

C1) reacting compound 7 obtained at step A with compound 10 obtained at step B1 to provide compound 15 of formula:

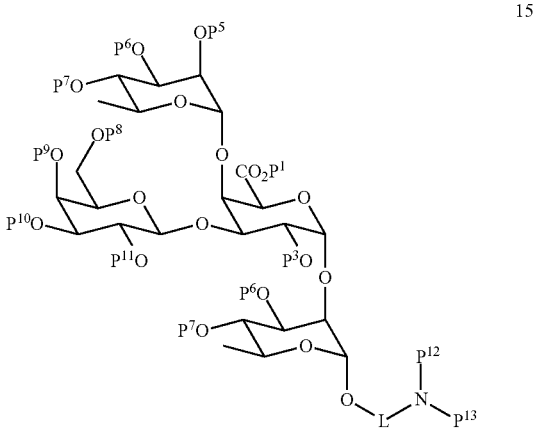

15 wherein $P^1$, $P^3$, $P^5$-$P^{13}$ represent protecting groups;

or

C2) reacting compound 7 obtained at step A with compound 12 obtained at step B2 to provide compound 16 of formula:

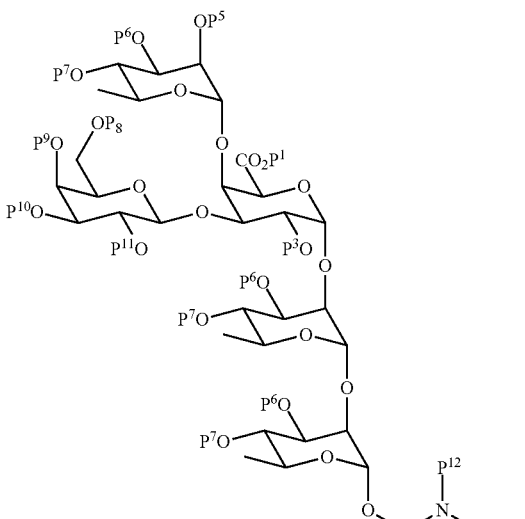

16 wherein $P^1$, $P^3$, $P^5$-$P^{13}$ represent protecting groups;

or

C3) reacting compound 7 obtained at step A with compound 14 obtained at step B3 to provide compound 17 of formula:

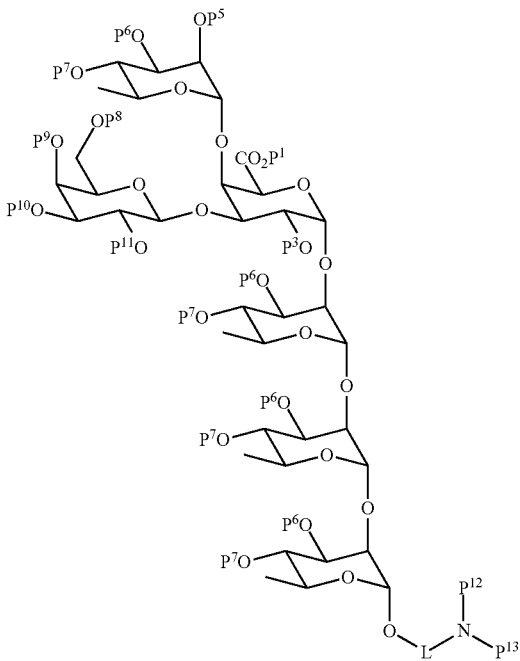

17 wherein $P^1$, $P^3$, $P^5$-$P^{13}$ represent protecting groups; and

D) performing removal of protecting groups $P^1$, $P^3$, $P^5$-$P^{13}$ on compounds 15, 16 and 17 to provide the saccharides of general formula (II).

$P^1$, $P^2$, $P^3$, $P^5$, $P^6$, $P^7$, $P^8$, $P^9$, $P^{10}$, $P^{11}$, $P^{12}$ and $P^{13}$ represent protecting groups. The term "protecting group" as used herein refers to commonly used groups in organic synthesis, preferably used for protection of amines, hydroxyl groups, thiols, imines, carbonyls, carboxyls or other common functional groups, and particularly preferred for amines and hydroxyl groups.

More preferably, $P^2$, $P^3$, $P^5$, $P^6$, $P^7$, $P^8$, $P^9$, $P^{10}$ and $P^{11}$ are suitable protecting groups for hydroxyl groups, more preferably different suitable protecting groups for hydroxyl groups capable of being removed subsequently one after another by a suitable sequence of deprotection reactions. Preferred protecting groups for hydroxyl groups are acetyl, benzyl, isopropylidene, benzylidene, benzoyl, p-methoxybenzyl, p-methoxybenzylidene, p-methoxyphenyl, p-bromobenzyledene, p-nitrophenyl, allyl, acetyl, isopropyl, p-bromobenzyl, dimethoxytrityl, trityl, 2-naphthylmethyl, pivaloyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl, levulinoyl. Specifically, protecting group $P^2$ is selected from allyl, p-methoxybenzyl, 2-naphthylmethyl, triisopropylsilyl, and tert-butyldimethylsilyl, protecting groups $P^3$, $P^6$, $P^7$, $P^8$, $P^9$ and $P^{10}$ represent benzyl and protecting groups $P^5$ and $P^{11}$ are selected from acetyl, benzoyl and levulinoyl. More specifically, protecting group $P^2$ represents allyl, protecting groups $P^3$, $P^6$, $P^7$, $P^8$, $P^9$ and $P^{10}$ represent benzyl and protecting groups $P^5$ and $P^{11}$ represent acetyl.

$P^{12}$ and $P^{13}$ are protecting groups suitable for amino groups. Preferred protecting groups for amines form together with the amine to be protected carbamates or amides. Examples of protecting groups forming carbamates include tert-butyloxy carbonyl, 9-fluorenylmethyl carbonyl, allyl carbonyl, trichloroethyl carbonyl and benzyloxy carbonyl. Examples of protecting groups forming amides include acetyl or trichloro acetyl. Preferably, protecting group $P^{12}$ represents benzyl and protecting group $P^{13}$ represents benzyloxy carbonyl.

Carboxylic acids are generally protected as esters. Therefore, protecting groups $P^1$ may be selected from the group consisting of or comprising methyl, ethyl, allyl, isopropyl, tert-butyl, phenyl, benzyl, p-methoxybenzyl. Preferably, $P^1$ represents methyl.

It is preferred that the reaction between trisaccharide 7 and monosaccharide 10, trisaccharide 7 and disaccharide 12, trisaccharide 7 and trisaccharide 14 is performed by activation with TBSOTf, in a mixture of apolar solvent and polar aprotic solvent at a temperature of between −80° C. and −60° C. Even more preferred is that the reaction between trisaccharide 7 and monosaccharide 10, trisaccharide 7 and disaccharide 12, trisaccharide 7 and trisaccharide 14 is performed by activation with TBSOTf, in a mixture of toluene and diethyl ether at −70° C.

It is also preferred that the reaction between disaccharide 4 and monosaccharide 5 is performed by activation with TBSOTf in an apolar solvent at a temperature of −50° C. and −10° C. and more preferably of −40° C. to −20° C. It is especially preferred that the reaction between disaccharide 4 and monosaccharide 5 is performed by activation with TBSOTf in dichloromethane at −30° C.

Preferably, the coupling between monosaccharide 1 and monosaccharide 2, monosaccharide 2 and compound 8, monosaccharide 2 and monosaccharide 10, and monosaccharide 2 and disaccharide 12 is performed by activation with TBSOTf in an apolar solvent at a temperature of between −10° C. to +10° C. Even more preferred is that the coupling between monosaccharide 1 and monosaccharide 2, monosaccharide 2 and compound 8, monosaccharide 2 and monosaccharide 10, and monosaccharide 2 and disaccharide 12 is performed by activation with TBSOTf in dichloromethane at 0° C.

The removal of protecting groups $P^1$, $P^3$, $P^5$-$P^{13}$ performed at step D involves:
first cleavage of the protecting groups sensitive to hydrogenation by subjecting the compound to hydrogen in presence of a palladium catalyst in a mixture of solvents, and
second cleavage of the base-labile protecting groups by treatment with a base in presence of hydrogen peroxide in a mixture of solvents. Preferably, the base is LiOH.

A further aspect according to the present invention refers to intermediates of general formula (7), (10), (15), (12), (16), (14) and (17):

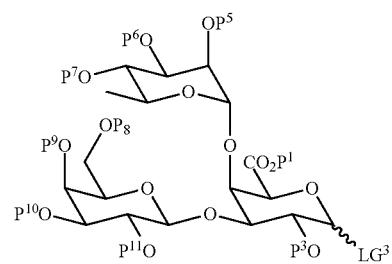

7 wherein $P^1$, $P^3$, $P^5$-$P^{11}$ represent protecting groups and $LG^3$ represents a leaving group selected from:

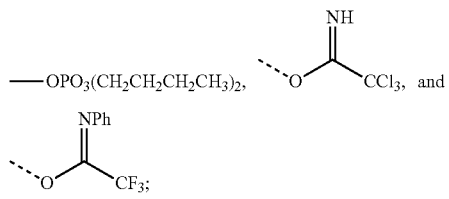

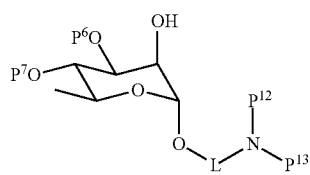

wherein $P^6$, $P^7$, $P^{12}$ and $P^{13}$ represent protecting groups and L has the meaning defined herein;

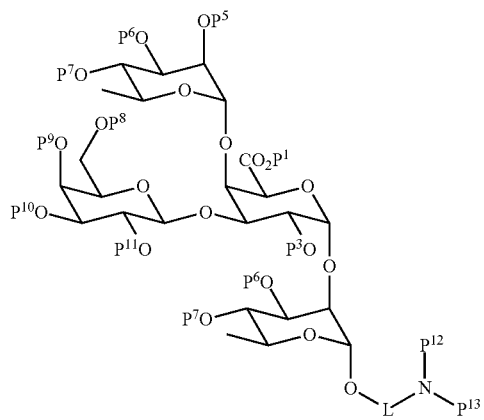

wherein $P^1$, $P^3$, $P^5$-$P^{13}$ represent protecting groups and L has the meaning defined herein;

12

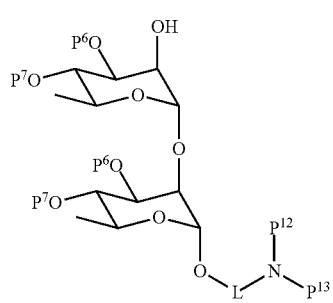

wherein $P^6$, $P^7$, $P^{12}$ and $P^{13}$ represent protecting groups and L has the meaning defined herein;

16

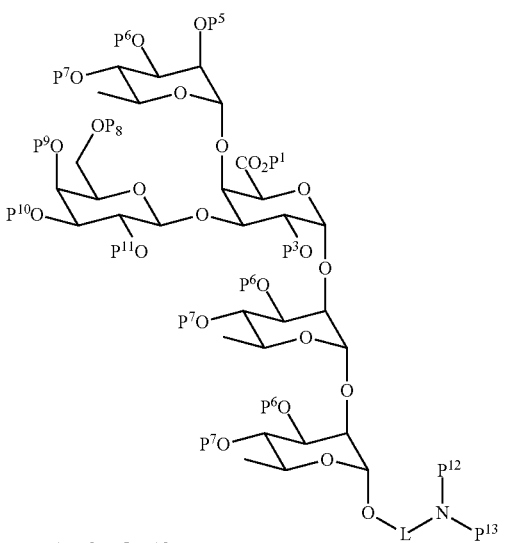

wherein $P^1$, $P^3$, $P^5$-$P^{13}$ represent protecting groups and L has the meaning defined herein;

14

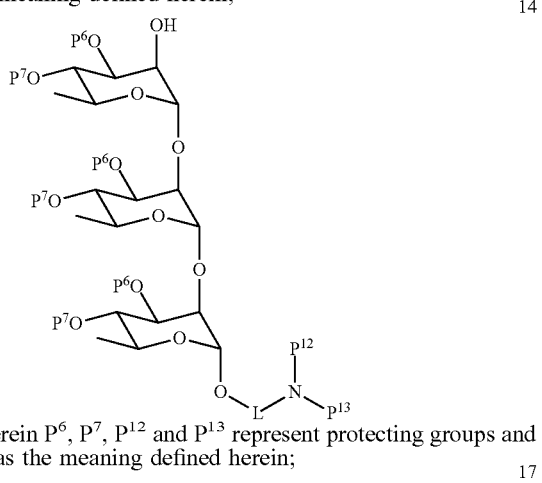

wherein $P^6$, $P^7$, $P^{12}$ and $P^{13}$ represent protecting groups and L has the meaning defined herein;

17

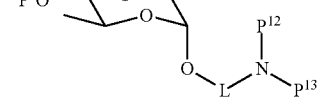

wherein $P^1$, $P^3$, $P^5$-$P^{13}$ represent protecting groups and L has the meaning defined herein.

In formulae (10), (15), (12), (16), (14) and (17), the linker -L- is preferably selected from: -$L^a$-, -$L^a$-$L^e$-, -$L^a$-$L^b$-$L^e$-, -$L^a$-$L^d$-$L^e$-;
wherein
-$L^a$- is selected from: —$(CH_2)_o$—, —$(CH_2$—$CH_2$—O$)_o$—$C_2H_4$—, —$(CH_2$—$CH_2$—O$)_o$—$CH_2$;
-$L^b$- represents —O—;
-$L^d$- is selected from: —$(CH_2)_q$—, —$(CF_2)_q$—, —$(CH_2$—$CH_2$—O$)_q$—$C_2H_4$—, and —$(CH_2$—$CH_2$—O$)_q$—$CH_2$—;
-$L^e$- is selected from: —$(CH_2)_{p1}$—, —$(CF_2)_{p1}$—, —$C_2H_4$—(O—$CH_2$—$CH_2)_{p1}$—, —$CH_2$—(O—$CH_2$—$CH_2)_{p1}$— and —$(CH_2)_{p1}$—O—$(CH_2)_{p2}$—;
and o, q, p1 and p2 are independently of each other an integer selected from 1, 2, 3, 4, 5, and 6.

An especially preferred intermediate is an intermediate of formula (10), (15), (12), (16), (14) or (17), wherein -L- represents —$(CH_2)_o$— and o is an integer selected from 2, 3, 4, 5 and 6.

$P^1$, $P^3$, $P^5$, $P^6$, $P^7$, $P^8$, $P^9$, $P^{10}$, $P^{11}$, $P^{12}$ and $P^{13}$ represent protecting groups. Preferably, protecting groups $P^3$, $P^5$, $P^6$, $P^7$, $P^8$, $P^9$, $P^{10}$, $P^{11}$ are selected from acetyl, benzyl, isopropylidene, benzylidene, benzoyl, p-methoxybenzyl, p-methoxybenzylidene, p-methoxyphenyl, p-bromobenzyl, p-bromobenzyledene, p-nitrophenyl, allyl, acetyl, isopropyl, p-bromobenzyl, dimethoxytrityl, trityl, 2-naphthylmethyl, pivaloyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl and levulinoyl.

It is further preferred that protecting groups $P^{12}$ and $P^{13}$ are selected from benzyl, tert-butyloxy carbonyl, 9-fluorenylmethyl carbonyl, allyl carbonyl, trichloroethyl carbonyl and benzyloxy carbonyl, acetyl and trichloro acetyl.

It is also preferred that protecting group $P^1$ is selected from methyl, ethyl, allyl, isopropyl, tert-butyl, phenyl, benzyl and p-methoxybenzyl.

In a more preferred embodiment, protecting groups $P^3$, $P^6$, $P^7$, $P^8$, $P^9$ and $P^{10}$ represent benzyl, protecting groups $P^5$ and $P^{11}$ are selected from acetyl, benzoyl and levulinoyl, protecting groups $P^{12}$ and $P^{13}$ are independently of each other selected from benzyl and benzyloxycarbonyl and $P^1$ represents methyl.

Thus, intermediates (7a), (10a), (15a). (12a), (16a), (14a) and (17a) are especially preferred:

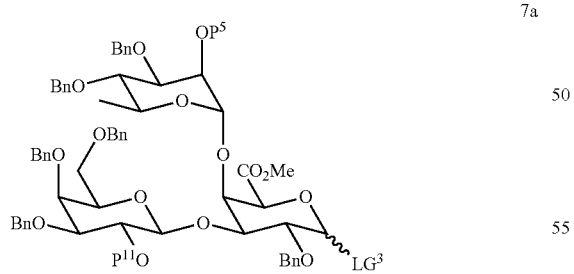

7a wherein $P^5$ and $P^{11}$ are independently from each other selected from acetyl (Ac), benzoyl (Bz) and levulinoyl (Lev), and $LG^3$ represents a leaving group selected from:

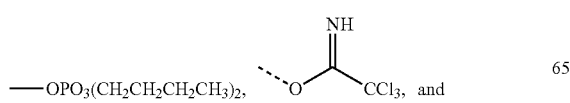

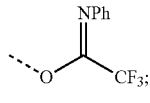

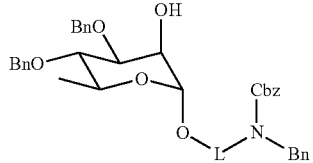

10a wherein L has the meaning defined herein;

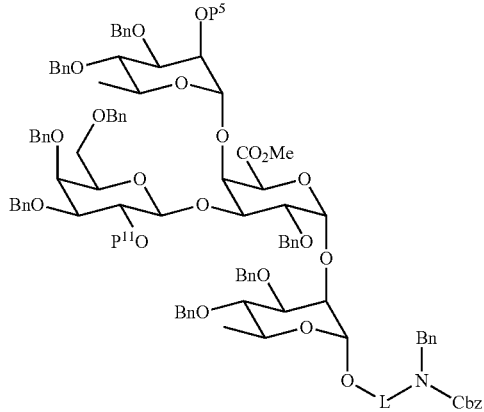

15a wherein $P^5$ and $P^{11}$ are independently from each other selected from acetyl (Ac), benzoyl (Bz) and levulinoyl (Lev) and L has the meaning defined herein;

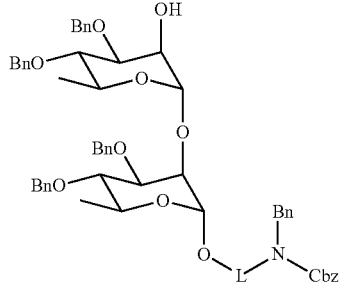

12a

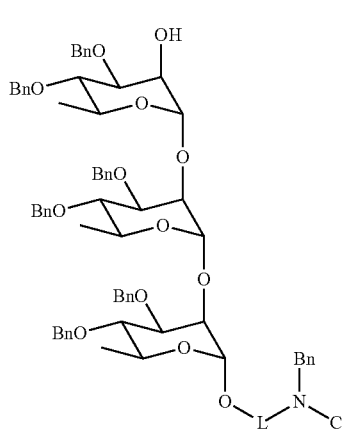

14a wherein L has the meaning defined herein;

16a

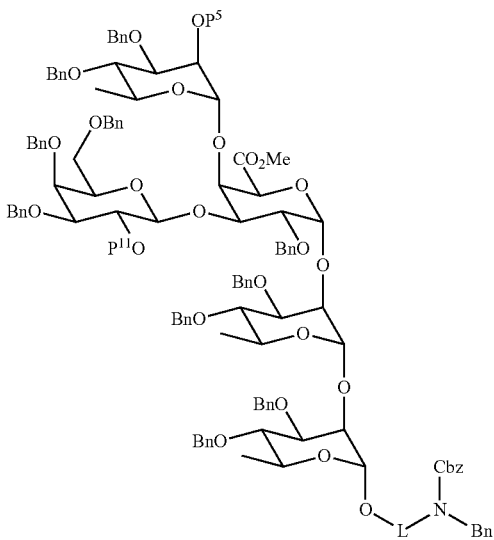

wherein $P^5$ and $P^{11}$ are independently from each other selected from acetyl (Ac), benzoyl (Bz) and levulinoyl (Lev) and L has the meaning defined herein;

17a

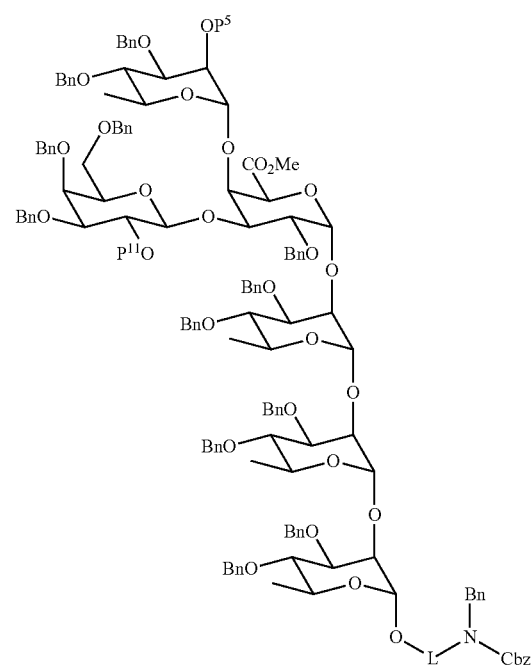

wherein $P^5$ and $P^{11}$ are independently from each other selected from acetyl (Ac), benzoyl (Bz) and levulinoyl (Lev) and L has the meaning defined herein.

In formulae (10a), (15a), (12a), (16a), (14a) and (17a), the linker -L- is preferably selected from: -$L^a$-, -$L^a$-$L^e$-, -$L^a$-$L^b$-$L^e$-, -$L^a$-$L^d$-$L^e$-;
wherein
-$L^a$- is selected from: —(CH$_2$)$_o$—, —(CH$_2$—CH$_2$—O)$_o$—C$_2$H$_4$—, —(CH$_2$—CH$_2$—O)$_o$—CH$_2$;
-$L^b$- represents —O—;
-$L^d$- is selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;
-$L^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
and o, q, p1 and p2 are independently of each other an integer selected from 1, 2, 3, 4, 5, and 6.

An especially preferred intermediate is an intermediate of formula (10a), (15a), (12a), (16a), (14a) or (17a), wherein -L- represents —(CH$_2$)$_o$— and o is an integer selected from 2, 3, 4, 5 and 6.

Glycoconjugates

Another aspect of the present invention refers to a conjugate comprising a saccharide according to the present invention. Surprisingly, said conjugate proved to be efficient as a vaccine for immunization against diseases associated with carbapenem-resistant *Klebsiella pneumoniae* bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, the saccharides of general formulae (I), (II), (II-a)-(II-c), (III), (III-a)-(III-c), (IV), (IV-a)-(IV-c), (V) and (V-a)-(V-c) are conjugated to an immunogenic carrier to provide conjugates, which present increased immunogenicity in comparison with the saccharide. Hence, under the scope of the present application is covered also a conjugate consisting of a saccharide fragment V*—[U$_{x+2}$—U$_{x+1}$—U$_x$]$_n$—V—O— wherein V*, U$_{x+2}$, U$_{x+1}$, U$_x$, V, x and n have the meanings defined herein, covalently linked through the O atom to an immunogenic carrier.

Said conjugate consists of at least one synthetic saccharide of the general formula (I) and an immunogenic carrier to which the at least one saccharide (I) is covalently bound.

Figure 4:
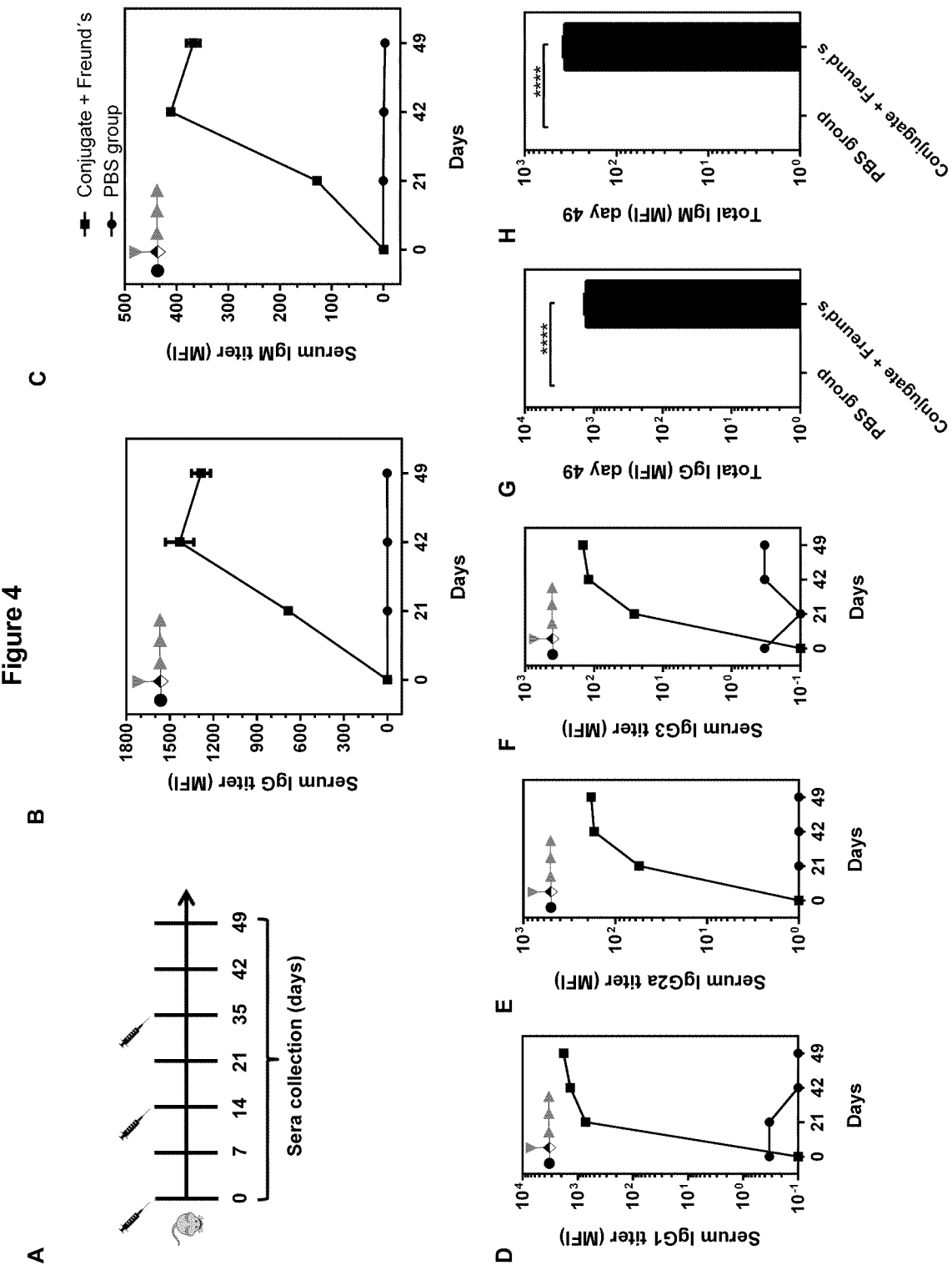

Surprisingly, it was found that immunization with a conjugate comprising a saccharide of general formula (I) covalently linked to an immunogenic carrier results in the production of high titers of antibodies specific to the carbohydrate part of the saccharide of general formula (I) (see for e.g. FIG. 4). Said antibodies are cross-reacting with the natural carbapenem-resistant *Klebsiella pneumoniae* capsular polysaccharide (see for e.g. FIG. 5, FIG. 7) and present opsonophagocytosis and bactericidal activity, thus conferring protection against carbapenem-resistant *Klebsiella pneumoniae*.

Vaccines containing the conjugate of the present invention cause fewer side effects and/or non-protective immune responses in comparison to vaccines containing isolated (and not synthesized) mixtures of saccharides obtained by non-selective cleavage of the capsular polysaccharide of *Klebsiella pneumoniae* or conjugates thereof. Moreover the inventive vaccines can be easier manufactured in accordance with the GMP regulations then the vaccines containing isolated mixtures of non-selectively cleaved capsular polysaccharides and are easier characterized, which makes stability and purity control easier as well as detection of kind and amount of impurities.

In this context the term "immunogenic carrier" is defined as a structure, which is conjugated to the saccharide to form a conjugate that presents an increased immunity in comparison with the saccharide per se. Thus, the conjugation of the saccharides of the general formulae (I), (II), (II-a)-(II-c), (III), (III-a)-(III-c), (IV), (IV-a)-(IV-c), (V) and (V-a)-(V-c) to the immunogenic carrier has as effect the stimulation of the immune response against the saccharide of general formula (I) without inducing an immune response against said immunogenic carrier.

Preferred immunogenic carriers are carrier proteins or glycosphingolipids with immunomodulatory properties. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Activated esters include N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarate (DSG), disuccinimidyl adipate (DSA), 2-pyridyldithiol-tetraoxatetradecane-N-hydroxysuccinimide (PEG-4-SPDP), bis-(4-nitrophenyl) adipate and bis-(4-nitrophenyl) succinate (see FIG. 2). Preferred activated esters are disuccinimidyl adipate (DSA), disuccinimidyl glutarate (DSG), bis-(4-nitrophenyl) adipate and bis-(4-nitrophenyl) succinate.

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the saccharides of general formula (I) are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is used as a carrier protein in a number of approved conjugate vaccines for diseases, such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker of the compounds of general formula (I).

Figure 3:
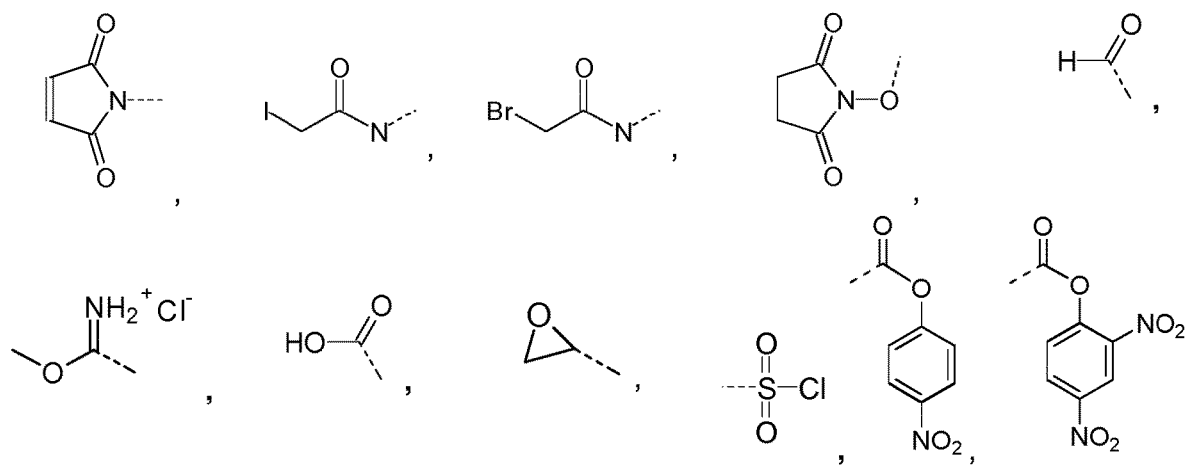

Said functional group X of the interconnecting molecules is selected of the group comprising or consisting of maleimide, α-iodoacetyl, α-bromoacetyl, N-hydroxysuccinimide ester (NHS), aldehyde, imidoester, carboxylic acid, alkyl sulfonate, sulfonyl chloride, epoxide, anhydride, carbonate (see FIG. 3).

Preferred is a conjugate of general formula (VI)

$$[V^*—[U_{x+2}—U_{x+1}—U_x]_n—V—O-L-NH-T]_m\text{-}CRM_{197} \quad (VI)$$

wherein m is comprised between 2 and 18;
-T- is selected from:

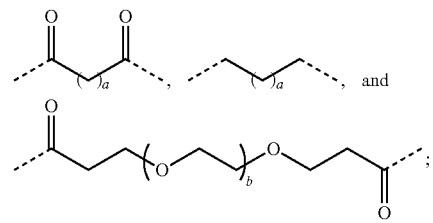

a represents an integer from 1 to 10;
b represents an integer from 1 to 4; and
$V^*$—, $U_{x+2}$, $U_{x+1}$, $U_x$, x, —V—, n and L have the meanings defined herein.

Even more preferred is a conjugate of general formula (VII)

$$[V^*—[U_{x+2}—U_{x+1}—U_x]_n—V—O-L-NH-T]_m\text{-}CRM_{197} \quad (VII)$$

wherein
x is an integer selected from 1, 2 and 3;
n is an integer selected from 1, 2 and 3;

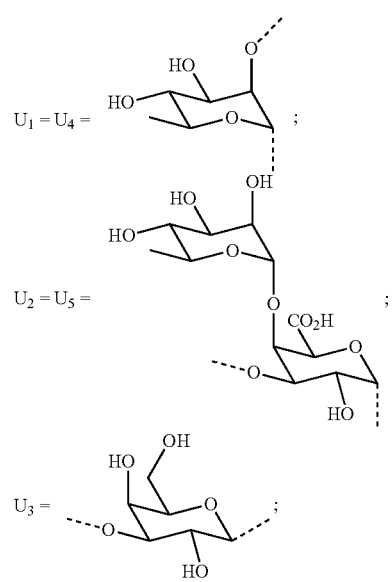

—V— represents a bond, —$U_{x+2}$— or —$U_{x+2}$—$U_{x+1}$—;
V*— represents H—, H—$U_x$—, or H—$U_{x+1}$—$U_x$—;
L represents a linker,
m is comprised between 2 and 18;
-T- is selected from:

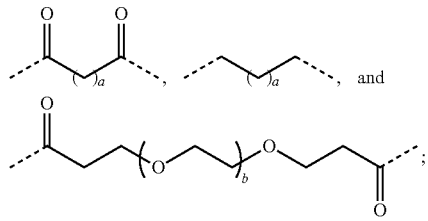

a represents an integer from 1 to 10; and
b represents an integer from 1 to 4.

Also preferred is a conjugate of general formula (VIII)

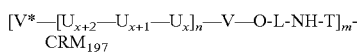

(VIII)

wherein
x is an integer selected from 1, 2 and 3;
n is an integer selected from 1, 2 and 3;

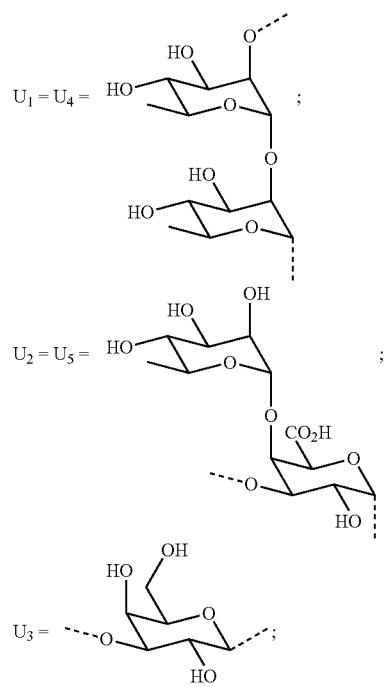

—V— represents a bond, —$U_{x+2}$— or —$U_{x+2}$—$U_{x+1}$—;
V*— represents H—, H—$U_x$—, or H—$U_{x+1}$—$U_x$—;
L represents a linker;
m is comprised between 2 and 18;
-T- is selected from:

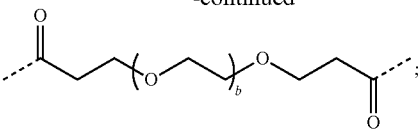

a represents an integer from 1 to 10; and
b represents an integer from 1 to 4.

Especially preferred is a conjugate of general formula (IX)

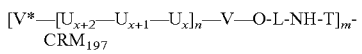

(IX)

wherein
x is an integer selected from 1, 2 and 3;
n is an integer selected from 1, 2 and 3;

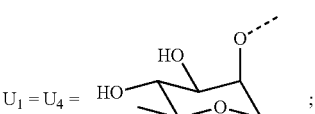

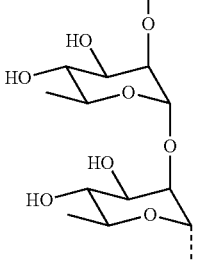

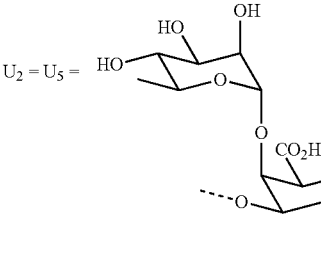

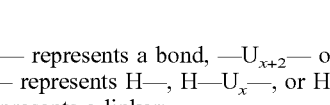

—V— represents a bond, —$U_{x+2}$— or —$U_{x+2}$—$U_{x+1}$—;
V*— represents H—, H—$U_x$—, or H—$U_{x+1}$—$U_x$—;
L represents a linker;
m is comprised between 2 and 18;
-T- is selected from:

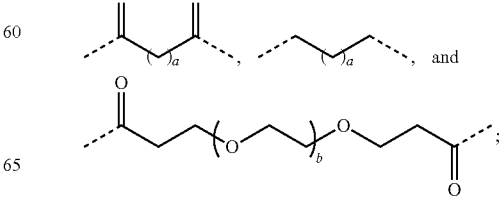

a represents an integer from 1 to 10; and
b represents an integer from 1 to 4.

Even more preferred is a conjugate of general formula (X)

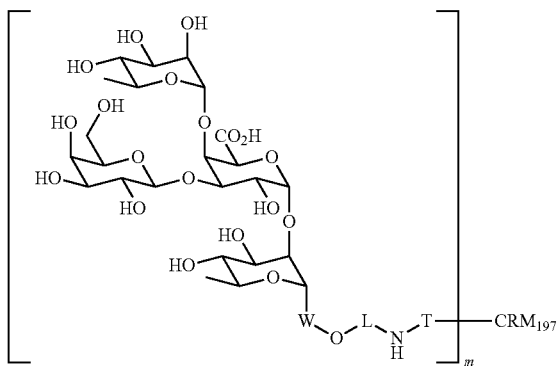
(X)

wherein

and L have the meanings defined herein,
m is comprised between 2 and 18;
-T- is selected from:

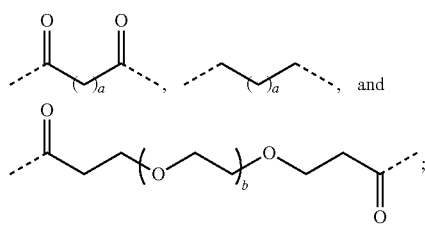

a represents an integer from 1 to 10; and
b represents an integer from 1 to 4.

Preferably -T- represents

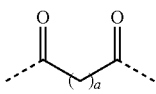

and a is an integer selected from 2, 3, 4, 5 and 6.

Thus, a conjugate of general formula (VI), (VII), (VIII), (IX) or (X), wherein -T-represents

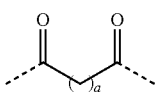

and a is an integer selected from 2, 3, 4, 5 and 6 is especially preferred.

Preferably, the linker -L- is selected from: -$L^a$-, -$L^a$-$L^e$-, -$L^a$-$L^b$-$L^e$-, and -$L^a$-$L^d$-$L^e$-;

-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^b$- represents —O—;
-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;
-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;
and o, q, p1 and p2 are independently of each other an integer selected from 1, 2, 3, 4, 5, and 6.

Thus, a conjugate of general formula (VI), (VII), (VIII), (IX) or (X), wherein -T-represents

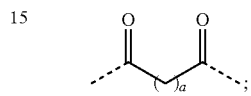

a is an integer selected from 2, 3, 4, 5 and 6;
-L- is selected from: -$L^a$-, -$L^a$-$L^e$-, -$L^a$-$L^b$-$L^e$-, and -$L^a$-$L^d$-$L^e$-;
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^b$- represents —O—;
-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;
-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;
and o, q, p1 and p2 are independently of each other an integer selected from 1, 2, 3, 4, 5, and 6; is especially preferred.

Still more preferred is a conjugate of general formula (VI), (VII), (VIII), (IX) or (X), wherein the linker -L- represents —$(CH_2)_o$—,
o is an integer selected from 2, 3, 4, 5 and 6;
-T- represents

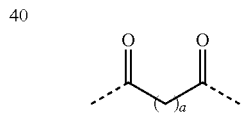

and a is an integer selected from 2, 3, 4, 5 and 6.

Preferably m is comprised between 2 and 18, more preferably between 5 and 15, even more preferably between 8 and 12.

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci. USA*, 1998, 95, 5690).

The conjugates of the saccharides of general formula I with a glycosphingolipid with immunomodulatory properties have the advantage of being heat stable. Additionally, they are able to produce in mice high titers of IgG1, IgG2a and IgG3 antibodies against the saccharide of general formula (I) and the capsular polysaccharide of CRKP. To be suitable for conjugation, a functionality is introduced on the glycosphingolipid with immuno-modulatory properties. Said functionality is prone to react directly with the terminal amino group of the linker of the saccharides of general formula I to provide conjugates of the saccharides of general formula I, or with the functional group Y of the interconnecting molecule to provide the modified glycosphingolipid with immunomodulatory properties.

Preferably, said functionality is introduced at the carbon 6 of the galactose moiety of the glycosphingolipid with immunomodulatory properties. Thus, the glycosphingolipid with immunomodulatory properties is functionalized with a functionality, which is prone of reacting with the terminal amino group of the saccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride. A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the C6 of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS) and 2-pyridyldithiols.

Said functional group X of the interconnecting molecules is selected of the group comprising or consisting of: maleimide, α-iodoacetyl, α-bromoacetyl, N-hydroxysuccinimide ester (NHS), aldehyde, carboxylic acid, epoxyde, alkyl sulfonate, sulfonyl chloride, anhydride and carbonate.

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

It was found that a conjugate comprising a saccharide of general formula (I), (II), (II-a), (II-b), (II-c), (III), (III-a), (III-b), (III-c), (IV), (IV-a), (IV-b), (IV-c), (V), (V-a), (V-b) or (V-c), and particularly a conjugate of general formula (VI), (VII), (VII), (IX) and (X), elicits a protective immune response in a human and/or animal host, and therefore is useful for prevention and/or treatment of diseases associated with carbapenem-resistant *Klebsiella pneumoniae* bacteria. Thus, the conjugates comprising the saccharides of general formula I conjugated to an immunogenic carrier are useful for prevention and/or treatment of diseases associated with carbapenem-resistant *Klebsiella pneumoniae* bacteria.

Pharmaceutical Compositions

Another aspect of the present invention is directed to a pharmaceutical composition or a vaccine comprising a conjugate that comprises a saccharide of general formula (I) conjugated to an immunogenic carrier and/or one saccharide of general formula (I) together with at least one pharmaceutically acceptable adjuvant and/or excipient. Said pharmaceutical composition can be used for raising a protective immune response in a human and/or animal host. Ideally, the pharmaceutical composition is suitable for use in humans.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to oil emulsions (e.g. Freund's adjuvant), saponins, aluminium or calcium salts (e.g. alum), non-ionic block polymer surfactants, and many others.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions may include a physiological salt, such as a sodium salt e.g. to control tonicity. Sodium chloride (NaCl) is typical and may be present at between 1 and 20 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg.

Pharmaceutical compositions may include compounds (with or without an insoluble metal salt) in plain water (e.g. w.f.i.), but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range.

Pharmaceutical compositions typically have a pH between 5.0 and 9.5 e.g. between 6.0 and 8.0.

Pharmaceutical compositions are preferably sterile and gluten free.

Pharmaceutical compositions are suitable for administration to animal (and, in particular, human) patients, and thus include both human and veterinary uses. They may be used in a method of raising an immune response in a patient, comprising the step of administering the composition to the patient.

The pharmaceutical compositions of the present invention may be administered before a subject is exposed to a carbapenem-resistant *Klebsiella pneumoniae* and/or after a subject is exposed to a carbapenem-resistant *Klebsiella pneumoniae*.

Pharmaceutical compositions may be prepared in unit dose form. In some embodiments a unit dose may have a volume of between 0.1-1.0 mL e.g. about 0.5 mL.

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. by an inhaler, using a fine powder or a spray. The composition may be prepared as a suppository. The composition may be prepared for nasal, aural or ocular administration e.g. as a spray or drops. Injectables for intramuscular administration are typical.

The pharmaceutical compositions may comprise an effective amount of an adjuvant i.e. an amount which, when administered to an individual, either in a single dose or as part of a series, is effective for enhancing the immune response to a co-administered carbapenem-resistant *Klebsiella penumoniae* antigen. This amount can vary depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range that can be determined through routine trials.

Techniques for the formulation and administration of the vaccine of the present invention may be found in "Remington's Pharmaceutical Sciences" Mack Publishing Co., Easton Pa.

A therapeutically effective dosage of one conjugate according to the present invention or of one saccharide of general formula (I) refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgement of the prescribing physician.

Another aspect of the present invention is directed to a method of inducing immune response against carbapenem-resistant *Klebsiella pneumoniae* in a human and/or animal host, said method comprising administering of the saccharide of general formula (I) and/or salt thereof and/or a conjugate thereof or pharmaceutical composition thereof to said human and/or animal host. A method of treating or preventing diseases caused by carbapenem-resistant *Klebsiella pneumoniae* in a human and/or animal host according to the present invention comprises administering of at least one saccharide of general formula (I) and/or salt thereof and/or a conjugate thereof or pharmaceutical composition thereof to said human and/or animal host.

Immunological Assays

Yet another aspect of the present invention refers to saccharide of general formula (I) for use as marker in immunological assays for detection of antibodies against carbapenem-resistant *Klebsiella pneumoniae.*

Such assays comprise, for instance, microarray and ELISA useful for detection of antibodies against carbapenem-resistant *Klebsiella pneumoniae.*

The saccharides of the present invention can be easily conjugated to solid supports for providing immunological assays useful for detection of antibodies against carbapenem-resistant *Klebsiella pneumoniae*. Said solid supports present on their surface a functionality that is prone to react with the amino group of saccharides of general formula (I) or with the functional group Y of the interconnecting molecule to provide modified solid supports, presenting on their surface the functional group X of the interconnecting molecule that can further react with the amino group of saccharides of general formula (I). In an embodiment according to the present invention the solid supports are microarray slides, which present on their surface a functionality that is prone to react with the functional group Y of the interconnecting molecule to provide modified microarray slides, presenting of their surface the functional group X of the interconnecting molecule. Examples of such microarray slides include, but are not restricted to Corning® epoxide coated slides or Corning® GAPS™ II coated slides.

In a preferred embodiment the solid supports are microarray slides presenting on their surface a functionality that is prone to react with the amino group of saccharides of general formula (I), and more preferably an N-hydroxysuccinimide (NHS) activated ester. Such microarray slides are for example CodeLink® NHS slides.

DESCRIPTION OF THE FIGURES

FIG. 1 shows the chemical structure of the repeating unit of carbapenem-resistant *Klebsiella pneumoniae* capsular polysaccharide.

FIG. 2 provides examples of commercially available interconnecting molecules according to the present invention.

FIG. 3 provides examples of functional group X of the interconnecting molecule according to the present invention.

FIG. 4: Evaluation of the immunogenicity of hexasaccharide 23* in mice by microarray. Immunization with the conjugate $CRM_{197}$-23* induces high antibody titers in mice.

(A) C57BL/6 mice (n=3) were immunized subcutaneously with 3 doses, each containing 3 μg of hexasaccharide 23* in Freund's adjuvant. Hyperimmune sera were pooled and the total IgG, IgM and IgG isotypes (IgG1, IgG2a and IgG3) endpoint titer was determined by glycan microarray (B-F); respectively. Total serum IgG and IgM titer at day 49 are shown in (G and H), respectively. Antibody titers were plotted as MFI values of n=3±SEM. Bars represent mean values+SEM *P≤0.1, P≤0.05, *P≤0.01 and ****P≤0.001.

Figure 5:
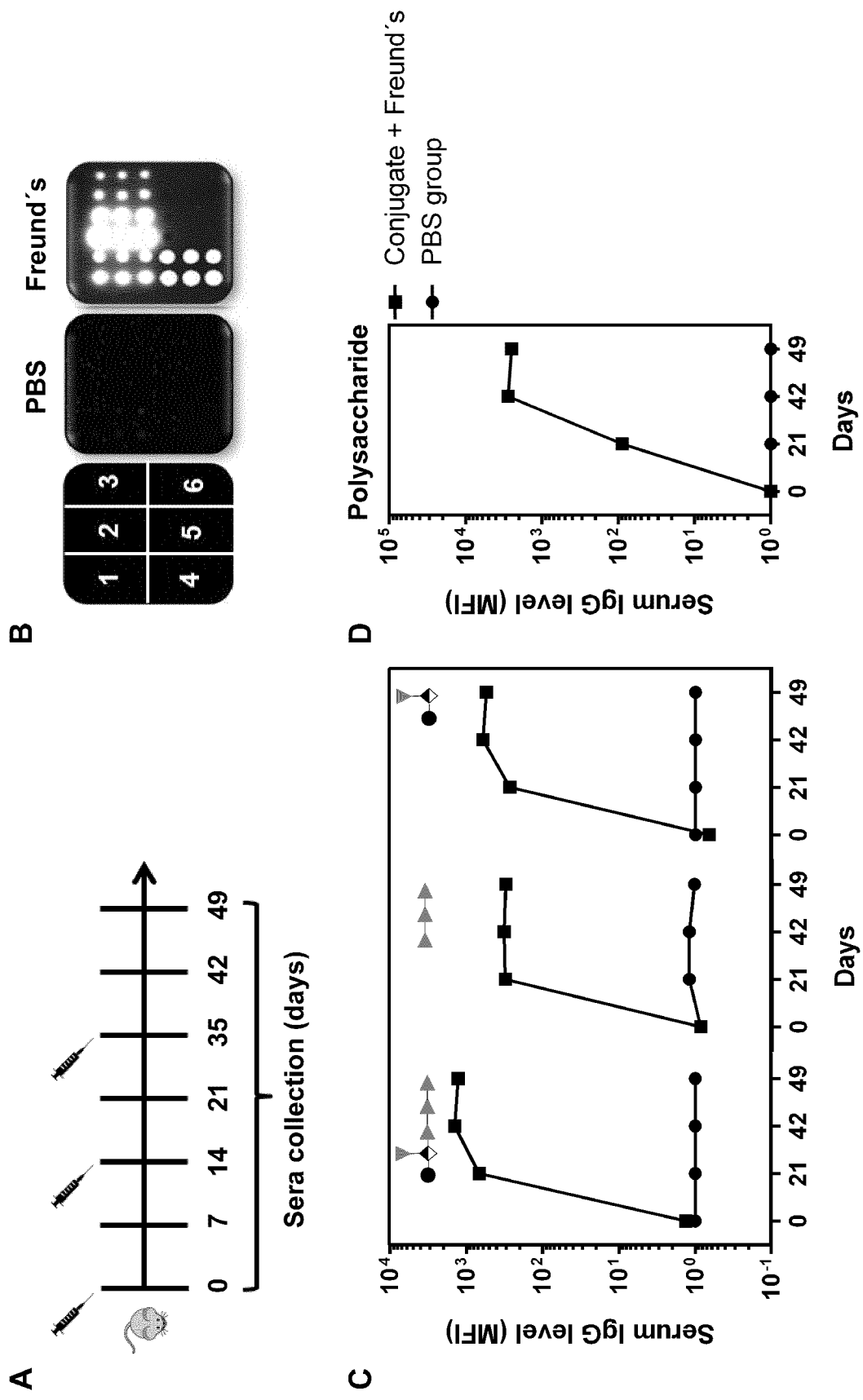

FIG. 5: Microarray analysis of the polyclonal sera raised in mice by the conjugate CRM$_{197}$-23*. The hyperimmune sera raised in mice immunized with conjugate CRM$_{197}$-23* formulated with Freund's adjuvant were subjected to microarray analysis.

(A) Immunization pattern.

(B) Left panel showing printing pattern of microarray slides
- position 1: hexasaccharide 23* Gal(β1-3)[Rha(α1-4)]GalA(α1-2)Rha(α1-2)Rha(α1-2)Rha(α1-1)aminopentanol),
- position 2: trisaccharide Rha(α1-2)Rha(α1-2)Rha(α1-1) aminopentanol,
- position 3: trisaccharide Gal(β1-3)[Rha(α1-4)]GalA(α1-2)aminopentanol),
- position 4: Polysaccharide (C200, clade 1) corresponding to CPS from carbapenem-resistant strain *K. pneumoniae* strain 34 (CPS-K34),
- position 5: Polysaccharide (clade 2) corresponding to CPS from *K. pneumoniae*, and
- position 6: Polysaccharide (non typable) corresponding to CPS from *K. pneumoniae*.

Right panel is the representative microarray scanning with pooled sera from mice (n=3) immunized with the conjugate CRM$_{197}$-23* with two booster immunization.

(C) The serum cross-reactivity with oligosaccharides expressed as MFI values of n=3±SEM.

(D) The serum cross-reactivity with capsular polysaccharide from carbapenem-resistant strain *K. pneumoniae* strain 34 (CPS-K34) expressed as MFI values of n=3±SEM.

Figure 6:
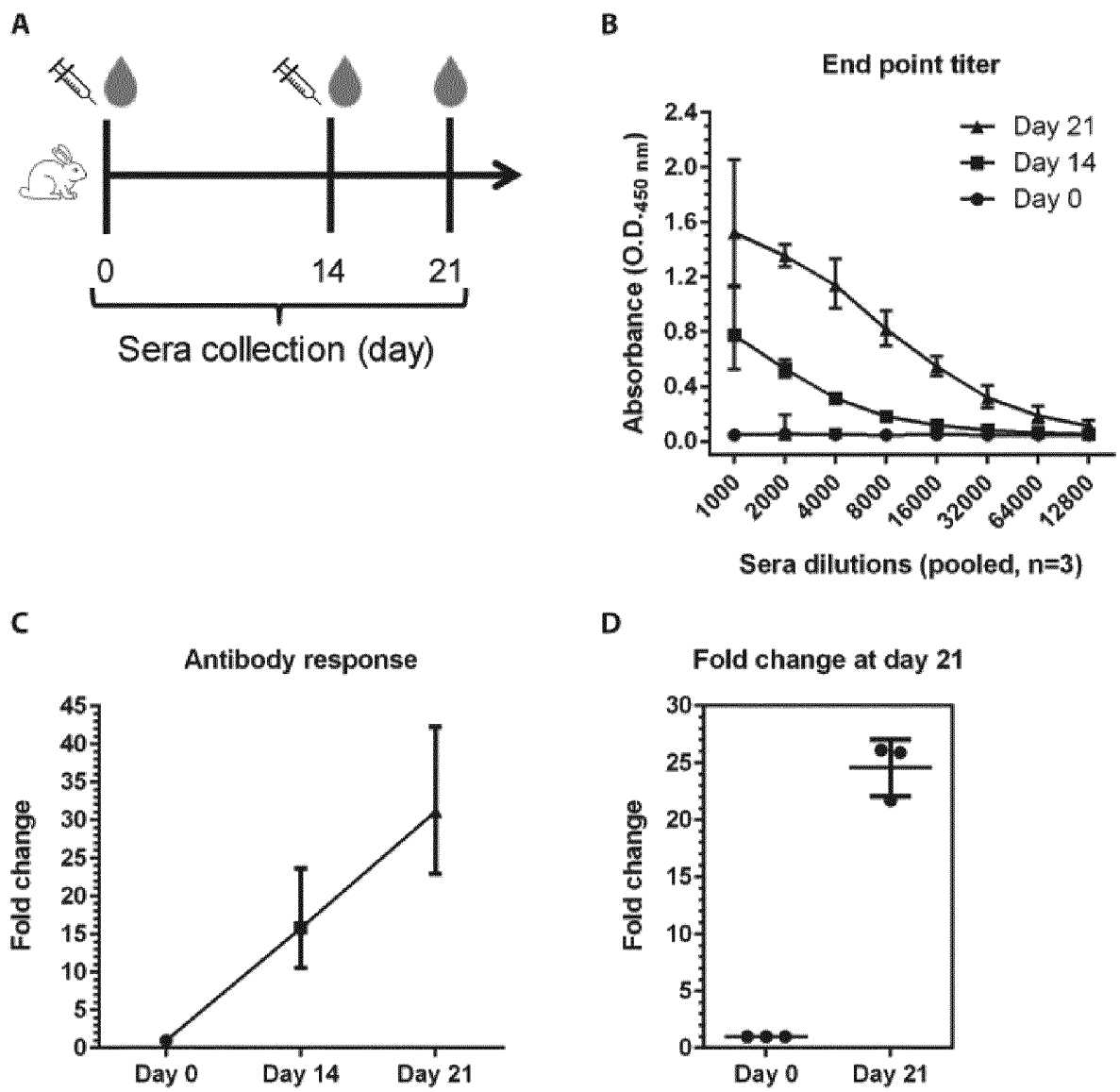

FIG. 6: End point titer analysis. Immunization with CRM$_{197}$-23* conjugate induces high antibody titers in rabbits. Three rabbits (female ZIKA rabbits, 10-12 weeks, 2.5-3 kg) were immunized subcutaneously with 10 μg sugar equivalent CRM$_{197}$-23* conjugate in alum formulation at day 0 and 14. The sera were collected before and after immunization and antibody response was analyzed by ELISA.

(A) Schematic representation of immunization and sera collection.

(B) The endpoint titer (total IgG) was determined in day 0, 14 and 21 pooled sera (n=3).

(C) The antibody response were analyzed at each time point and plotted as fold chance.

(D) The individual rabbit antibody titer at day 0 and 21. Each dot represents the individual animal. The data were plotted as geometric mean with 95% Cl.

FIG. 7: Microarray analysis of the sera raised in rabbits by the conjugate CRM$_{197}$-23*.

(A) Printing pattern of microarray slides.

(B) Glycan microarray analysis after the incubation of slide(s) with pooled (n=3) anti-CRM$_{197}$-23* conjugate sera (day 21).

(C) The mean fluorescence intensity (MFI) of each spot of 0.2 mM concentration.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

A. Chemical Synthesis

General Information:

Commercial grade solvents were used unless stated otherwise. Dry solvents were obtained from a Waters Dry Solvent System. Solvents for chromatography were distilled prior to use. Sensitive reactions were carried out in heat-dried glassware and under an argon atmosphere. Analytical thin layer chromatography (TLC) was performed on Kieselgel 60 F254 glass plates precoated with a 0.25 mm thickness of silica gel. Spots were visualized by staining with vanillin solution (6% (w/v) vanillin and 10% (v/v) sulfuric acid in 95% EtOH) or Hanessian's stain (5% (w/v) ammonium molybdate, 1% (w/v) cerium(II) sulfate and 10% (v/v) sulfuric acid in water). Silica column chromatography was performed on Fluka Kieselgel 60 (230-400 mesh). $^1$H, $^{13}$C and two-dimensional NMR spectra were measured with a Varian 400-MR spectrometer at 296 K. Chemical shifts (d) are reported in parts per million (ppm) relative to the respective residual solvent peaks (CDCl$_3$: d 7.27 in $^1$H and 77.23 in $^{13}$C NMR; CD$_3$OD: d 3.31 in $^1$H and 49.15 in $^{13}$C NMR). The following abbreviations are used to indicate peak multiplicities: s singlet; d doublet; dd doublet of doublets; t triplet; dt doublet of triplets; q quartet; m multiplet. Coupling constants (J) are reported in Hertz (Hz). Optical rotation (OR) measurements were carried out with a Schmidt & Haensch UniPol L1000 polarimeter at A=589 nm and a concentration (c) expressed in g/100 mL in the solvent noted in parentheses. High resolution mass spectrometry (HRMS) was performed at the Free University Berlin, Mass. Spectrometry Core Facility, with an Agilent 6210 ESI-TOF mass spectrometer. Infrared (IR) spectra were measured with a Perkin Elmer 100 FTIR spectrometer.

Abbreviations

All: allyl;

TBAI: tetrabutylammonium iodide;

Bn: benzyl;

Cbz: benzyloxycarbonyl;

EtOAc: ethyl acetate;

Lev: levulinoyl;

PMB: 4-methoxybenzyloxyl;

Tr: triphenylmethyl.

Example A-1: Synthesis of 1,2-O-Isopropylidene-3-O-allyl-5-O-triphenylmethyl-α-D-xylofuranoside (2*)

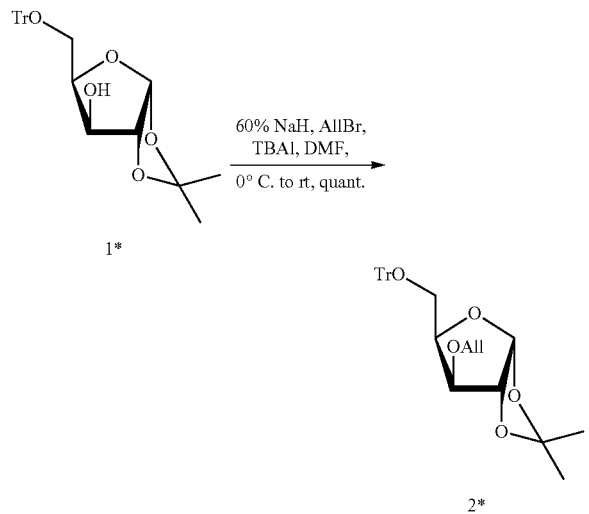

The alcohol 1* (*Chem. Eur. J.* 2013, 19, 3995-4002) (21 g, 48.6 mmol) was dissolved in dry DMF (140 mL) and cooled to 0° C. 60% NaH (3.88 g, 97 mmol) was slowly added. After 5 min, AllBr (8.4 mL, 97 mmol) and TBAI (1.79 g, 4.86 mmol) were added. The mixture was allowed to stir overnight at room temperature. The mixture was quenched with sat. NH$_4$Cl and then poured into ice water. The mixture was extracted with CH$_2$Cl$_2$. The combined organic layer was washed with sat. NH$_4$Cl and water, dried and concentrated in vacuo. The residue was purified by column chromatography on silica gel (Hexanes/EtOAc=20/1 to 10/1 to 1/1) to give target compound 2* (22.9 g, quant.). $[α]_D^{25}$=−2.85 (c=1.07, CHCl$_3$); $^1$H NMR (400 MHz, CDCl$_3$) δ 7.46-7.21 (m, 15H), 5.88 (d, J=4.0 Hz, 1H), 5.71 (m, 1H), 5.13 (m, 2H), 4.54 (d, J=4.0 Hz, 1H), 4.38 (m, 1H), 4.04 (dd, J=5.6, 12.8 Hz, 1H), 3.98 (d, J=2.8 Hz, 1H), 3.93 (dd, J=5.6, 12.8 Hz, 1H), 3.50 (dd, J=5.2, 8.8 Hz, 1H), 3.31 (dd, J=7.6, 8.8 Hz, 1H), 1.54 (s, 3H), 1.33 (s, 3H); $^{13}$C NMR (101 MHz, CDCl$_3$) δ 143.9, 134.2, 128.8, 127.9, 127.1, 117.6, 111.7, 105.0, 86.9, 82.6, 81.5, 79.4, 71.3, 60.7, 26.9, 26.3; HRMS (ESI): calcd for C$_{30}$H$_{32}$O$_5$Na [M+Na]$^+$: 495.2147; found: 495.2167.

Example A-2: Synthesis of 3-O-Allyl-4,5-O-isopropylidene-D-xylose di(ethylthio)acetal (3*)

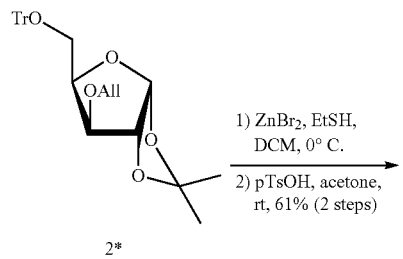

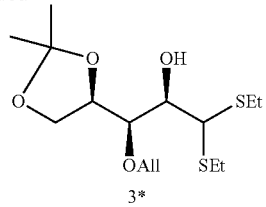

Acetonide 2* (9.5 g, 20.1 mmol) was dissolved in CH$_2$Cl$_2$ (80.4 mL) and cooled to 0° C. EtSH (29.7 mL, 402 mmol) and ZnBr$_2$ (22.64 g, 101 mmol) were added and the mixture was stirred at 0° C. for 75 min. The reaction was quenched by adding 5% aq. ammonium hydroxide and the resulting slurry was diluted with CH$_2$Cl$_2$ and 1 M aq. HCl. The phases were separated and the aqueous layer was extracted with CH$_2$Cl$_2$. The combined organic layers were dried over Na$_2$SO$_4$ and concentrated in vacuo. The residue was purified by column chromatography on silica gel (Hexanes/EtOAc=1/3 to EtOAc) to give the alcohol (5.44 g, 18.36 mmol). pTsOH (524 mg, 2.75 mmol) was added to a solution of the above triol (5.44 g, 18.36 mmol) in acetone (124 mL). The mixture was stirred at room temperature for 12 h and the reaction was quenched with sat aq. NaHCO$_3$. The suspension was filtered and the solvent was removed under reduced pressure. The residue was purified by column chromatography on silica gel (Hexane/EtOAc=4.5/1) to give alcohol 3* (4.13 g, 61% for two steps). $[α]_D^{25}$=−43.76 (c=0.98, CHCl$_3$); $^1$H NMR (400 MHz, CDCl$_3$) δ 5.92 (m, 1H), 5.22 (d, J=18.8 Hz, 1H), 5.11 (d, J=10.4 Hz, 1H), 4.38 (m, 2H), 4.14 (dd, J=6.8, 12.4 Hz, 1H), 4.02 (m, 2H), 3.79 (dd, J=1.6, 6.8 Hz, 1H), 3.69 (t, J=8.0 Hz, 1H), 3.43 (dd, J=1.2, 8.4 Hz, 1H), 3.10 (br, 1H), 2.56-2.75 (m, 4H), 1.40 (s, 3H), 1.34 (s, 3H), 1.25 (t, J=7.2 Hz, 3H), 1.24 (t, J=7.6 Hz, 3H); $^{13}$C NMR (101 MHz, cdcl$_3$) δ 135.0, 117.0, 109.3, 78.7, 77.7, 73.4, 72.2, 65.9, 55.3, 26.7, 25.5, 25.2, 24.1, 14.6, 14.5; HRMS (ESI): calcd for C$_{15}$H$_{28}$O$_4$S$_2$Na [M+Na]$^+$: 359.1327, found: 359.1331.

Example A-3: Synthesis of 2-O-Benzyl-3-O-allyl-4,5-O-isopropylidene-D-xylose di(ethylthio)acetal (4*)

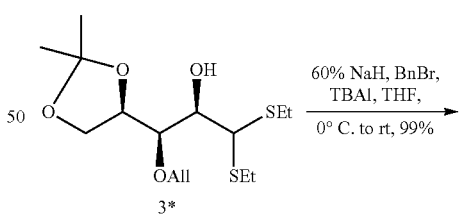

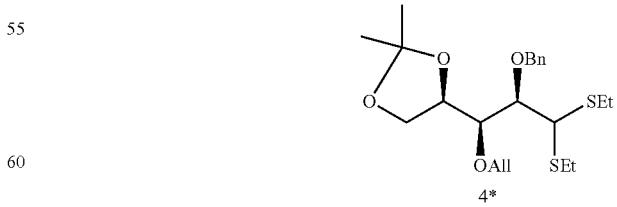

The alcohol 3* (4.12 g, 12.27 mmol) was dissolved in dry THF (40 mL) and cooled to 0° C. 60% NaH (0.98 g, 24.54 mmol) was slowly added. After 5 min, BnBr (2.2 mL, 18.41 mmol) and TBAI (0.29 g, 1.23 mmol) were added. The mixture was allowed to stir overnight at room temperature. The mixture was quenched with MeOH and concentrated in vacuo. The residue was diluted with EtOAc. The mixture was washed with water, dried and concentrated in vacuo. The residue was purified by column chromatography on silica gel (Hexanes/EtOAc=12/1) to give target compound 4* (5.2 g, 99%). [α]$_D^{25}$=11.80 (c=0.98, CHCl$_3$); $^1$H NMR (400 MHz, CDCl$_3$) δ 7.32-7.17 (m, 5H), 5.81 (m, 1H), 5.14 (d, J=17.2 Hz, 1H), 5.04 (d, J=10.4 Hz, 1H), 4.82 (d, J=11.2 Hz, 1H), 4.65 (d, J=11.2 Hz, 1H), 4.23 (m, 1H), 4.12 (m, 1H), 4.08 (d, J=4.0 Hz, 1H), 3.86 (t, J=6.4 Hz, 1H), 3.81 (t, J=4.0 Hz, 1H), 3.71 (t, J=8.0 Hz, 1H), 3.63 (t, J=5.6 Hz, 1H), 2.52-2.75 (m, 4H), 1.35 (s, 3H), 1.26 (s, 3H), 1.20 (t, J=7.2 Hz, 3H), 1.17 (t, J=7.2 Hz, 3H); $^{13}$C NMR (101 MHz, CDCl$_3$) δ 138.3, 134.9, 128.2, 127.9, 127.6, 116.8, 108.8, 82.7, 79.9, 76.4, 74.7, 73.8, 65.8, 52.4, 26.5, 25.7, 25.6, 25.2, 14.5, 14.4; HRMS (ESI): calcd for C$_{22}$H$_{34}$O$_4$S$_2$Na [M+Na]$^+$: 449.1796, found: 449.1802.

Example A-4: Synthesis of 2-O-Benzyl-3-O-allyl-D-xylose di(ethylthio)acetal (5*)

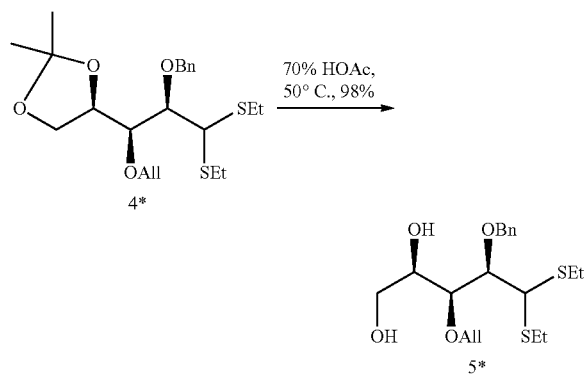

Acetonide 4* (5.2 g, 12.19 mmol) was dissolved in 70% aq. HOAc (121 mL). The mixture was allowed to stir at 50° C. for 3 h. The mixture was concentrated in vacuo. The residue was co-evaporated twice with toluene and then purified by column chromatography on silica gel (Hexanes/EtOAc=1/1.4) to give compound 5* (4.59 g, 98%). [α]$_D^{25}$=1.60 (c=0.78, CHCl$_3$); $^1$H NMR (400 MHz, CDCl$_3$) δ 7.33-7.20 (m, 5H), 5.80 (m, 1H), 5.13 (d, J=16.0 Hz, 1H), 5.07 (d, J=10.4 Hz, 1H), 4.81 (d, J=10.8 Hz, 1H), 4.67 (d, J=11.2 Hz, 1H), 4.21 (dd, J=5.6, 12.4 Hz, 1H), 3.97-4.03 (m, 3H), 3.76 (br, 1H), 3.58-3.69 (m, 3H), 2.54-2.75 (m, 6H), 1.19 (t, J=8.4 Hz, 3H), 1.15 (t, J=7.2 Hz, 3H); $^{13}$C NMR (101 MHz, CDCl$_3$) δ 138.3, 134.5, 128.3, 127.9, 127.6, 117.7, 83.1, 80.9, 75.3, 74.1, 71.1, 64.4, 53.1, 26.0, 25.2, 14.5, 14.5; HRMS (ESI): calcd for C$_{19}$H$_{30}$O$_4$S$_2$Na [M+Na]$^+$: 409.1483, found: 409.1488.

Example A-5: Synthesis of 2-O-Allyl-3-O-benzyl-L-threo-dialdose di(ethylthio)acetal (6*)

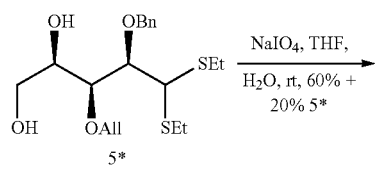

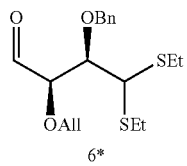

NaIO$_4$ (1.508 g, 7.05 mmol) in H$_2$O (20 mL) was added to a solution of diol 5* (2.42 g, 6.27 mmol) in THF (79 mL) at room temperature. After stirring for 2 h, the mixture was diluted with CH$_2$Cl$_2$ and washed with sat aq. NaHCO$_3$ and brine, dried over Na$_2$SO$_4$, concentrated in vacuo. The residue was purified by column chromatography on silica gel (Hexanes/EtOAc=7/1) to give aldehyde 6* (1.34 g, 60%) and the starting diol 5* (474 mg, 20%). [α]$_D^{25}$=1.27 (c=34.61, CHCl$_3$); $^1$H NMR (400 MHz, CDCl$_3$) δ 9.79 (s, 1H), 7.28-7.20 (m, 5H), 5.81 (m, 1H), 5.16 (d, J=17.2 Hz, 1H), 5.12 (d, J=10.4 Hz, 1H), 4.76 (d, J=11.2 Hz, 1H), 4.57 (d, J=11.2 Hz, 1H), 4.13 (dd, J=6.0, 12.8 Hz, 1H), 3.98-4.07 (m, 3H), 2.51-2.70 (m, 4H), 1.20 (t, J=7.2 Hz, 3H), 1.14 (t, J=7.2 Hz, 3H); $^{13}$C NMR (101 MHz, CDCl$_3$) δ 201.8, 137.5, 133.9, 128.5, 128.3, 128.0, 118.6, 83.1, 83.0, 74.8, 72.9, 52.3, 26.1, 25.5, 14.5, 14.3; HRMS (ESI): calcd for C$_{18}$H$_{26}$O$_3$S$_2$Na [M+Na]$^+$: 377.1221, found: 377.1220.

Example A-6: Synthesis of (R)-4-Benzyl-3-((2S,3R,4S,5R)-4-allyloxy-5-benzyloxy-6,6-bis(ethylthio)-3-hydroxy-2-(4-methoxybenzyloxy)hexanoyl)oxazolidin-2-one (8*)

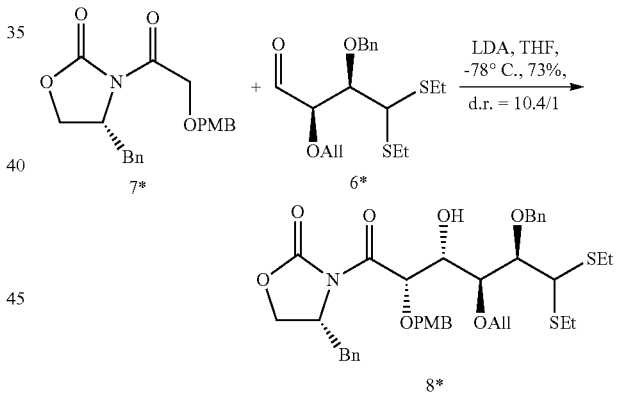

A stirred solution of di-isopropylamine (0.978 mL, 6.86 mmol) in THF (11 mL) was cooled to −20° C. and n-BuLi (2.74 mL, 2.5 M in hexane, 6.86 mmol) was added dropwise and stirred for 30 min, then re-cooled to −78° C. and auxiliary 7* (2.44 g, 6.86 mmol) as a solution in 5.5 mL THF was added to the mixture over a period of 20 min. After 1.5 h, aldehyde 6* (1.2 g, 3.43 mmol) was dissolved in 9.8 mL THF and added to the mixture over a period of 30 min. The reaction was quenched after 2 h by the addition of 33 mL sat. aq. NH$_4$Cl-solution and then warmed to r.t., where the mixture was stirred for another 30 min. The mixture was extracted with CH$_2$Cl$_2$ (3×150 mL) and dried over MgSO$_4$. The solvent was removed in vacuo and the crude product was purified by flash column chromatography on silica gel (gradient Hexanes/EtOAc=8:1-3:1) to afford 8* (1.78 g, d.r.=10.4/1, 73%). [α]$_D^{25}$=−30.3 (c=1.09, CHCl$_3$); $^1$H NMR (400 MHz, CDCl$_3$) δ 7.31-7.10 (m, 12H), 6.79 (d, J=8.4 Hz, 2H), 5.79 (m, 1H), 5.42 (br s, 1H), 5.18 (d, J=17.2 Hz, 1H), 5.01 (d, J=10.8 Hz, 1H), 4.81 (d, J=11.2 Hz, 1H), 4.67 (d, J=11.2 Hz, 1H), 4.62 (m, 1H), 4.55 (d, J=10.4 Hz, 1H), 4.31 (d, J=10.8 Hz, 1H), 4.28 (m, 1H), 4.17-3.91 (m, 7H), 3.70 (s, 3H), 3.11 (dd, J=2.8, 13.2 Hz, 1H), 2.81 (d, J=7.6 Hz, 1H), 2.71-2.49 (m, 5H), 1.17 (t, J=7.6 Hz, 3H), 1.14 (t, J=7.6 Hz, 3H); $^{13}$C NMR (101 MHz, CDCl$_3$) δ 171.4, 159.6, 153.1, 138.4, 135.0, 134.9, 130.2, 129.5, 129.4, 129.0, 128.3, 128.2, 128.1, 127.9, 127.4, 127.3, 116.2, 113.9, 113.8, 83.0, 78.5, 77.5, 74.7, 72.9, 72.4, 71.9, 66.9, 55.3, 54.9, 52.8, 37.8, 25.8, 25.3, 14.5, 14.5; HRMS (ESI): calcd for C$_{38}$H$_{47}$NO$_8$S$_2$Na [M+Na]$^+$: 732.2641, found: 732.2650.

Example A-7: Synthesis of (R)-4-Benzyl-3-((2S,3R,4S,5R)-4-allyloxy-5-benzyloxy-6,6-bis(ethylthio)-3-levulynoxy-2-(4-methoxybenzyloxy)hexanoyl)oxazolidin-2-one (9*)

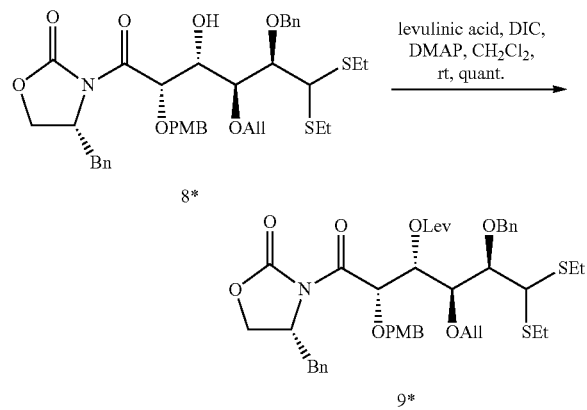

Alcohol 8* (1.65 g, 2.32 mmol) was dissolved in CH$_2$Cl$_2$ (43 mL). To the stirred solution at r.t., levulinic acid (0.35 mL, 3.49 mmol), 4-dimethylaminopyridine (455 mg, 3.72 mmol) and di-isopropylcarbodiimide (0.55 mL, 3.49 mmol) were added. After 12 h, the same amount of levulinic acid, 4-dimethylaminopyridine and di-isopropylcarbodiimide were added and the mixture was stirred for additional 6 h. After filtration over celite, the solvent was removed in vacuo. The crude product was purified by column chromatography on silica gel (Hexanes/EtOAc=2:1) to afford ester 9* (1.88 g, quant.) as the pale yellow oil. [α]$_D^{25}$=3.72 (c=0.96, CHCl$_3$); $^1$H NMR (400 MHz, CDCl$_3$) δ 7.32-7.15 (m, 12H), 6.77 (d, J=8.8 Hz, 2H), 5.83 (m, 1H), 5.68 (dd, J=2.0, 8.0 Hz, 1H), 5.45 (d, J=2.0 Hz, 1H), 5.25 (d, J=17.2 Hz, 1H), 5.04 (d, J=10.4 Hz, 1H), 4.70 (d, J=10.8 Hz, 1H), 4.53 (d, J=10.8 Hz, 1H), 4.45 (s, 2H), 4.36-4.26 (m, 3H), 4.11-4.00 (m, 3H), 3.94 (m, 1H), 3.74-3.64 (m, 1H), 3.69 (s, 3H), 3.16 (dd, J=2.8, 13.6 Hz, 1H), 2.68-2.44 (m, 9H), 1.96 (s, 3H), 1.18 (t, J=7.6 Hz, 3H), 1.14 (t, J=7.6 Hz, 3H); $^{13}$C NMR (101 MHz, CHCl$_3$) δ 206.1, 172.0, 170.1, 159.5, 153.0, 138.6, 135.9, 135.0, 130.6, 130.0, 129.4, 129.1, 128.9, 128.0, 128.0, 127.2, 127.1, 116.1, 113.9, 113.6, 81.9, 75.3, 74.5, 72.8, 72.6, 71.9, 66.8, 66.3, 55.4, 55.3, 53.4, 37.8, 37.1, 29.8, 28.1, 25.6, 24.7, 14.4, 14.4; HRMS (ESI): calcd for C$_{43}$H$_{53}$NO$_{10}$S$_2$Na [M+Na]$^+$: 830.3009, found: 830.2964.

Example A-8: Synthesis of (R)-4-Benzyl-3-((ethyl 3-O-allyl-2-O-benzyl-4-O-levulinoyl-1-thio-α-D-galactopyranosid)oxazolidin-2-one)uronate (10*)

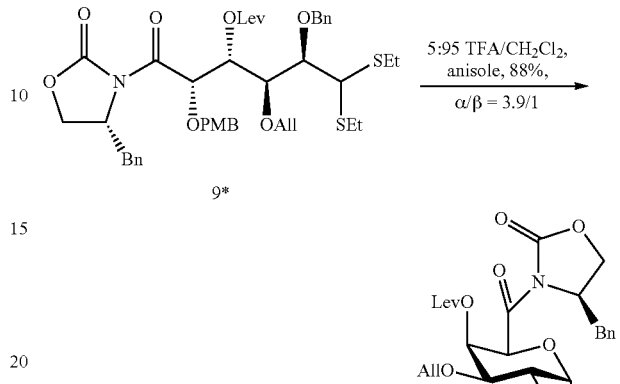

Paramethoxybenzyl ether 9* (1.85 g, 2.29 mmol) was dissolved in a mixture of 5% TFA in CH$_2$Cl$_2$ (30.2 mL) and stirred at r.t. After 5 min, anhydrous anisole (0.45 mL, 4.14 mmol) was added. The reaction was quenched after 13 h by addition of sat. aq. NaHCO$_3$-solution (195 mL) and CH$_2$Cl$_2$ (98 mL). The aqueous layer was separated and extracted with CH$_2$Cl$_2$ (3×200 mL). The solvent was removed in vacuo and the crude product was purified by column chromatography on silica gel (Hexanes/EtOAc=1.2:1 to 1:1.2) to afford 10* (1.26 g, α/β=3.9/1, 88%) as white foam. [α]$_D^{25}$=82.49 (c=1.12, CHCl$_3$); $^1$H NMR (400 MHz, CDCl$_3$) δ 7.34-7.15 (m, 10H), 5.87-5.75 (m, 3H), 5.47 (d, J=5.6 Hz, 1H), 5.21 (d, J=15.6 Hz, 1H), 5.10 (d, J=10.4 Hz, 1H), 4.68 (d, J=12.4 Hz, 1H), 4.63 (d, J=12.4 Hz, 1H), 4.59 (m, 1H), 4.16-3.99 (m, 5H), 3.75 (dd, J=3.2, 10.0 Hz, 1H), 3.20 (dd, J=3.2, 13.6 Hz, 1H), 2.64-2.39 (m, 7H), 2.02 (s, 3H), 1.19 (t, J=7.2 Hz, 3H); $^{13}$C NMR (101 MHz, CHCl$_3$) δ 205.8, 172.3, 166.9, 153.3, 138.0, 135.5, 134.3, 129.3, 129.1, 128.4, 128.0, 127.8, 127.3, 117.4, 84.3, 75.6, 74.0, 72.9, 71.1, 69.5, 68.7, 67.3, 55.4, 37.9, 37.3, 29.8, 28.0, 24.2, 14.6; HRMS (ESI): calcd for C$_{33}$H$_{39}$O$_9$NS$_2$Na [M+Na]$^+$: 648.2243, found: 648.2237.

Example A-9: Synthesis of Methyl (ethyl 3-O-allyl-2-O-benzyl-4-O-levulinoyl-1-thio-α-D-galactopyranosid)uronate (11*)

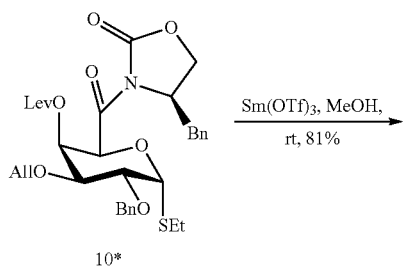

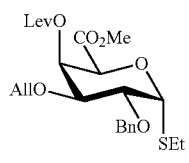

11*

Oxazolidinone 10* (1.02 g, 1.63 mmol) was dissolved in MeOH (9.7 mL) and Sm(OTf)$_3$ (293 mg, 0.49 mmol) was added. The mixture was vigorously stirred for 60 h at r.t. The solvents were then removed in vacuo and the crude product was purified by silica gel flash column chromatography (Hexanes/EtOAc=1.2/1) to afford compound 11* (634 mg, 81%). $[\alpha]_D^{25}$=122.62 (c=1.05, CHCl$_3$); $^1$H NMR (400 MHz, CDCl$_3$) δ 7.31-7.19 (m, 5H), 5.78 (m, 1H), 5.64 (dd, J=1.6, 3.6 Hz, 1H), 5.41 (d, J=5.6 Hz, 1H), 5.19 (d, J=17.6 Hz, 1H), 5.08 (d, J=10.4 Hz, 1H), 4.86 (br s, 1H), 4.65 (d, J=12.0 Hz, 1H), 4.59 (d, J=12.0 Hz, 1H), 4.05 (dd, J=5.2, 12.8 Hz, 1H), 3.95 (dd, J=5.6, 12.8 Hz, 1H), 3.88 (dd, J=5.6, 9.6 Hz, 1H), 3.69 (s, 3H), 3.63 (dd, J=3.6, 10.0 Hz, 1H), 2.71-2.39 (m, 6H), 2.08 (s, 3H), 1.18 (t, J=7.6 Hz, 3H); $^{13}$C NMR (101 MHz, CHCl$_3$) δ 205.9, 171.3, 168.0, 137.9, 134.3, 128.3, 127.9, 127.8, 117.2, 83.9, 75.4, 74.0, 72.9, 71.0, 69.0, 68.8, 52.6, 37.9, 29.7, 27.9, 24.0, 14.6; HRMS (ESI): calcd for C$_{24}$H$_{32}$O$_8$NSNa [M+Na]$^+$: 503.1716, found: 503.1701.

Example A-10: Synthesis of Methyl (ethyl 3-O-allyl-2-O-benzyl-1-thio-α-D-galactopyranosid)uronate (12*)

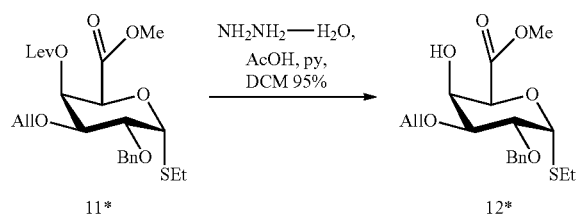

Levulinate ester 11* (322 mg, 0.67 mmol) was dissolved in CH$_2$Cl$_2$ (7 mL). Subsequently, pyridine (1.6 mL), AcOH (1.1 mL) and hydrazine hydrate (65 µL) were added. After stirring at r.t. for 2.5 h, the reaction mixture was quenched by the addition of acetone (7 mL) and the solvents were removed in vacuo. The crude product was purified by silica gel flash column chromatography (Hexanes/EtOAc=1.5/1 to 1/1) to give alcohol 12* (244 mg, 95%). $[\alpha]_D^{25}$=84.74 (c=0.23, CHCl$_3$); $^1$H NMR (400 MHz, CDCl$_3$) δ 7.31-7.20 (m, 5H), 5.85 (m, 1H), 5.39 (d, J=5.2 Hz, 1H), 5.21 (d, J=17.2 Hz, 1H), 5.13 (d, J=10.4 Hz, 1H), 4.77 (br s, 1H), 4.61 (s, 2H), 4.31 (br s, 1H), 4.19-4.06 (m, 2H), 3.97 (m, 1H), 3.75 (s, 3H), 3.58 (dd, J=3.2, 9.6 Hz, 1H), 2.58-2.42 (m, 3H), 1.20 (t, J=7.2 Hz, 3H); $^{13}$C NMR (101 MHz, CDCl$_3$) δ 169.2, 137.8, 134.3, 128.4, 128.0, 127.8, 117.6, 83.4, 74.4, 72.7, 71.8, 70.1, 68.5, 52.5, 24.0, 14.7; HRMS (ESI): calcd for C$_{19}$H$_{26}$O$_6$SNa [M+Na]$^+$: 405.1348, found: 405.1329.

Example A-11: Synthesis of Methyl 2-O-acetyl-3,4-di-O-benzyl-α-L-rhamnopyranosyl-(1→4)-(ethyl 3-O-allyl-2-O-benzyl-1-thio-α-D-galactopyranosid) uronate (14*)

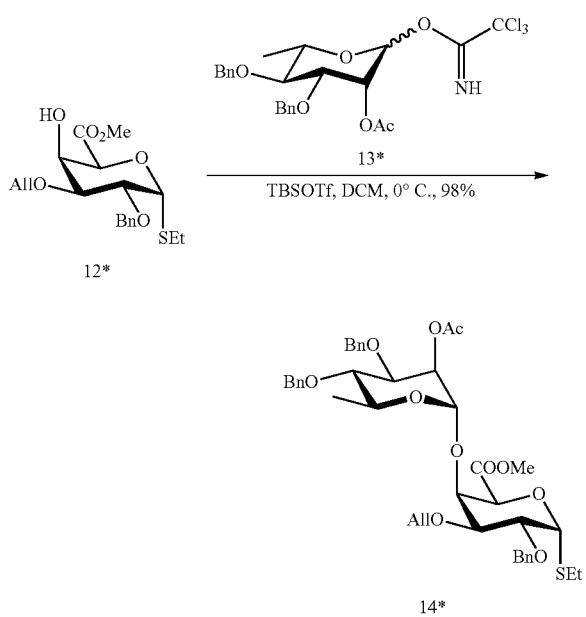

Donor 13* (*Eur. J. Org. Chem.* 2008, 5526-5542) (885 mg, 1.66 mmol) and acceptor 12* (319 mg, 0.83 mmol) were dissolved in dry CH$_2$Cl$_2$ (8 mL). 4 Å MS (800 mg) were added. The mixture was stirred at r.t. for 20 min and then cooled to 0° C., followed by slow addition of TBSOTf (38 µL, 0.16 mmol). After 1 h, the reaction was quenched with Et$_3$N. The reaction mixture was filtered and concentrated in vacuo. The residue was purified by column chromatography on silica gel (Hexanes/EtOAc=3/1) to give 14* (612 mg, 98%). $[\alpha]_D^{25}$=50.77 (c=0.25, CHCl$_3$); $^1$H NMR (400 MHz, CDCl$_3$) δ 7.34-7.15 (m, 15H), 5.84 (m, 1H), 5.44 (br, 1H), 5.39 (d, J=5.6 Hz, 1H), 5.20 (d, J=17.6 Hz, 1H), 5.09 (d, J=9.6 Hz, 1H), 5.07 (br, 1H), 4.79 (d, J=11.2 Hz, 1H), 4.76 (br, 1H), 4.65 (s, 2H), 4.55 (d, J=9.2 Hz, 1H), 4.48 (d, J=10.4 Hz, 1H), 4.38 (br s, 1H), 4.30 (d, J=12.4 Hz, 1H), 4.20-4.08 (m, 2H), 3.99 (m, 1H), 3.76 (m, 1H), 3.70 (s, 3H), 3.62 (m, 1H), 3.53 (m, 1H), 3.28 (t, J=8.0 Hz, 1H), 2.55-2.39 (m, 2H), 2.06 (s, 3H), 1.19 (m, 6H); $^{13}$C NMR (101 MHz, CHCl$_3$) δ 170.1, 168.8, 139.0, 138.2, 137.8, 134.6, 128.5, 128.5, 128.4, 128.2, 128.2, 128.2, 128.1, 128.0, 127.7, 127.5, 127.4, 117.0, 99.3, 84.1, 79.6, 78.1, 78.0, 75.1, 74.8, 73.7, 72.8, 72.0, 71.9, 70.4, 68.8, 68.4, 52.6, 24.2, 21.2, 18.1, 14.8; HRMS (ESI): calcd for C$_{41}$H$_{50}$O$_{11}$SNa [M+Na]$^+$: 773.2972, found: 773.2953.

Example A-12: Synthesis of Methyl 2-O-acetyl-3,4-di-O-benzyl-α-L-rhamnopyranosyl-(1→4)-(ethyl 2-O-benzyl-1-thio-α-D-galactopyranosid)uronate (15*)

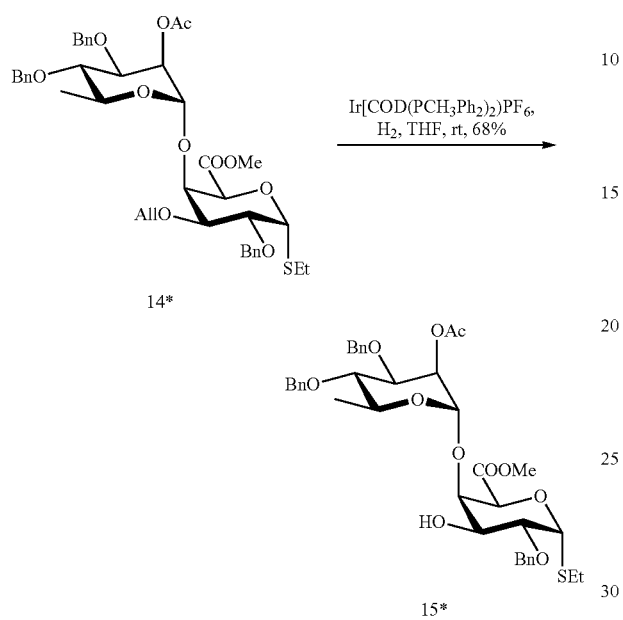

Under an argon atmosphere, a solution of Ir[COD (PCH$_3$Ph$_2$)$_2$]PF$_6$ (5.63 mg, 6.66 µmol) in THF (1 mL) was degassed by vacuum and gassed with H$_2$ (~5 cycles). The reaction was stirred under H$_2$ atmosphere at r.t. for 20 min before the solution was degassed by vacuum and gassed with argon (~5 cycles). To this reaction flask, a solution of an allyl protected disaccharide 14* (25 mg, 33 µmol) in THF (1 mL) was added via syringe in one portion at r.t. The reaction was stirred at r.t. for 21 h before concentrated in vacuo. The crude product was treated with p-TsOH (1.3 mg, 6.66 µmol) in a mixture of CH$_2$Cl$_2$ and MeOH (2 mL, v/v=1/1) for 12 h at r.t. The mixture was diluted with EtOAc, washed with sat NaHCO$_3$, dried over Mg$_2$SO$_4$ and concentrated in vacuo. The residue was purified by column chromatography on silica gel (Hexanes/EtOAc=2/1) to give alcohol 15* (16 mg, 68%). [α]$_D^{25}$=38.5 (c=0.16, CHCl$_3$); $^1$H NMR (400 MHz, CDCl$_3$) δ 7.34-7.19 (m, 15H), 5.55 (d, J=4.8 Hz, 1H), 5.41 (br s, 1H), 5.11 (br s, 1H), 4.80 (d, J=11.2 Hz, 1H), 4.78 (br s, 1H), 4.65 (d, J=11.2 Hz, 1H), 4.55 (d, J=11.2 Hz, 1H), 4.49 (d, J=11.2 Hz, 1H), 4.46 (d, J=11.6 Hz, 1H), 4.40 (br s, 1H), 4.34 (d, J=10.8 Hz, 1H), 3.94 (m, 1H), 3.86 (dd, J=2.4, 10.0 Hz, 1H), 3.75 (dd, J=3.2, 9.2 Hz, 1H), 3.72 (s, 3H), 3.55 (m, 1H), 3.29 (t, J=9.6 Hz, 1H), 2.40-2.57 (m, 2H), 2.06 (s, 3H), 1.20 (m, 6H); $^{13}$C NMR (101 MHz, CDCl$_3$) δ 170.3, 168.7, 139.0, 138.2, 137.0, 128.7, 128.4, 128.4, 128.3, 128.2, 127.7, 127.5, 127.4, 99.4, 83.2, 79.7, 78.0, 75.6, 74.9, 74.9, 71.9, 71.9, 70.7, 70.2, 68.8, 68.4, 52.6, 29.8, 24.3, 21.3, 18.1, 14.9; HRMS (ESI): calcd for C$_{38}$H$_{46}$O$_{11}$SNa [M+Na]$^+$: 733.2659, found: 733.2680.

Example A-13: Synthesis of Methyl 2-O-acetyl-3,4-di-O-benzyl-α-L-rhamnopyranosyl-(1→4)-[2-O-acetyl-3,4,6-tri-O-benzyl-β-D-galactopyranosyl-(1→3)]-(ethyl 2-O-benzyl-1-thio-α-D-galactopyranosid)uronate (17*)

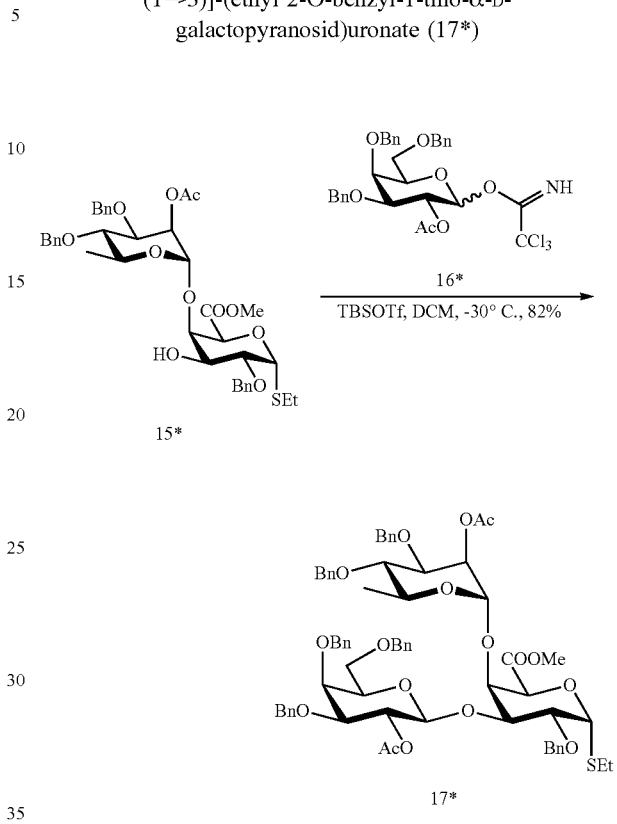

Donor 16* (*J. Am. Chem. Soc.* 2012, 134, 15556-15562) (323 mg, 0.51 mmol) and acceptor 15* (90 mg, 0.12 mmol) were dissolved in CH$_2$Cl$_2$ (2 mL). 4 Å MS (200 mg) were added. The mixture was stirred for 30 min at r.t., then cooled to −30° C., followed by slow addition of TBSOTf (9 µL, 0.038 mmol). After stirring at −30° C. for 1.5 h, the reaction mixture was quenched with Et$_3$N. The mixture was filtered and concentrated in vacuo. The residue was purified by column chromatography on silica gel (Hexanes/EtOAc=3/1 to 2/1) to afford trisaccharide 17* (123 mg, 82%). [α]$_D^{25}$=20.48 (c=0.18, CHCl$_3$); $^1$H NMR (400 MHz, CDCl$_3$) δ 7.30-7.14 (m, 30H), 5.43 (m, 1H), 5.31 (d, J=5.6 Hz, 1H), 5.28-5.24 (m, 2H), 4.86 (d, J=12 Hz, 1H), 4.81 (d, J=11.2 Hz, 1H), 4.70-4.47 (m, 9H), 4.41-4.32 (m, 4H), 4.05 (dd, J=6.0, 10.0 Hz, 1H), 3.94 (dd, J=2.0, 10.0 Hz, 1H), 3.81 (br, 1H), 3.74 (dd, J=3.2, 9.2 Hz, 1H), 3.64 (s, 3H), 3.55 (m, 2H), 3.49-3.44 (m, 2H), 3.38 (dd, J=2.8, 10.0 Hz, 1H), 3.27 (t, J=12.0 Hz, 1H), 2.52-2.35 (m, 2H), 1.97 (s, 3H), 1.87 (s, 3H), 1.17 (m, 6H); $^{13}$C NMR (101 MHz, CDCl$_3$) δ 170.2, 169.3, 168.6, 163.4, 139.0, 138.5, 138.4, 137.8, 137.8, 137.4, 128.6, 128.4, 128.4, 128.4, 128.3, 128.3, 128.2, 128.1, 128.1, 127.8, 127.8, 127.7, 127.5, 127.5, 127.4, 127.3, 102.1, 98.6, 83.8, 80.0, 79.5, 78.4, 77.1, 76.1, 74.7, 74.4, 73.8, 73.7, 73.5, 72.7, 72.6, 71.9, 71.7, 71.2, 70.4, 68.6, 68.2, 68.1, 52.5, 24.0, 21.1, 20.9, 18.0, 14.7; HRMS (ESI): calcd for C$_{67}$H$_{76}$O$_{17}$SNa [M+Na]$^+$: 1207.4701, found: 1207.4667.

Example A-14: Synthesis of 2-O-acetyl-3,4-di-O-benzyl-α-L-rhamnopyranosyl-(1→4)-[2-O-acetyl-3,4,6-tri-O-benzyl-β-D-galactopyranosyl-(1→3)]-(methyl 2-O-benzyl-D-galactopyranosid)uronate 1-N-phenyltrifluoroacetimidate (18*)

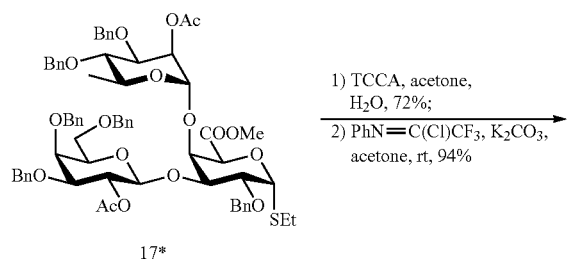

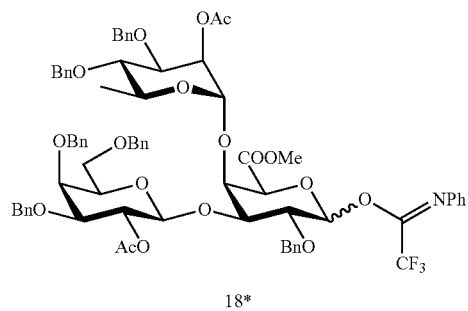

To a solution of trisaccharide 17* (140 mg, 0.118 mmol) in acetone and water (4/1, 5 mL), trichloroisocyanuric acid (27 mg, 0.118 mmol) was added at 0° C. Then, the reaction mixture was gradually warmed to r.t. and stirred overnight. Acetone was evaporated in vacuo. The residue was diluted with $CH_2Cl_2$ and washed with sat. $NaHCO_3$ and water. The organic layer was dried over anhydrous $MgSO_4$. The residue was purified by column chromatography (Hexanes/EtOAc=1/1.5-1/2) to give the hemiacetal (90 mg, 72%). To a solution of hemiacetal (90 mg, 0.079 mmol) in acetone (4 mL) was added $K_2CO_3$ (33 mg, 0.24 mmol) and PhN=C(Cl)CF$_3$ (49 mg, 0.24 mmol). The mixture was stirred overnight at r.t. The solution was filtered and concentrated in vacuo. The residue was purified by column chromatography on silica gel (Hexanes/EtOAc=2.5/1) to give imidate 18* (97 mg, 94%). $^1$H NMR (400 MHz, CDCl$_3$) δ 7.37-7.26 (m, 32H), 7.09 (m, 1H), 6.83 (d, J=7.6 Hz, 2H), 5.53 (br, 1H), 5.44 (br, 1H), 5.40 (dd, J=8.4, 10.0 Hz, 1H), 4.99-4.90 (m, 2H), 4.85-4.80 (m, 3H), 4.70-4.50 (m, 8H), 4.43 (s, 2H), 3.97-3.90 (m, 4H), 3.78 (s, 3H), 3.64-3.56 (m, 2H), 3.53-3.37 (m, 4H), 2.14 (s, 3H), 2.02 (s, 3H), 1.31 (d, J=8.0 Hz, 3H); $^{13}$C NMR (101 MHz, CDCl$_3$) δ 170.2, 169.1, 167.2, 143.3, 139.1, 138.5, 138.4, 137.9, 137.8, 137.3, 128.6, 128.5, 128.5, 128.4, 128.3, 128.3, 128.2, 128.2, 127.9, 127.9, 127.6, 127.6, 127.5, 127.5, 127.3, 124.3, 119.3, 101.6, 98.3, 79.9, 79.5, 78.2, 78.0, 77.5, 75.5, 74.8, 74.5, 74.4, 73.9, 73.8, 73.6, 72.6, 71.9, 71.8, 71.0, 68.5, 68.2, 68.2, 52.8, 21.3, 20.8, 18.0; HRMS (ESI): calcd for $C_{73}H_{76}F_3NO_{18}Na$ [M+Na]$^+$: 1334.4912, found: 1334.4892.

Example A-15: Synthesis of N-(Benzyl)benzyloxycarbonyl-5-amino-pentanyl 3,4-di-O-benzyl-α-L-rhamnopyranoside (19*)

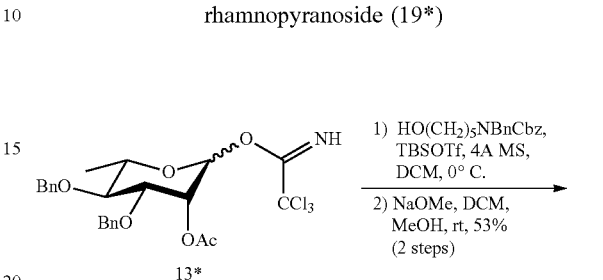

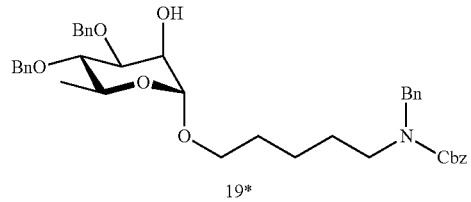

Donor 13* (209 mg, 0.39 mmol) and the linker (*Org. Lett.* 2013, 15, 2270-2273) (99 mg, 0.3 mmol) were dissolved in dry $CH_2Cl_2$ (4 mL). 4 Å MS (200 mg) was added. The mixture was stirred at r.t. for 30 min and then cooled to 0° C. TBSOTf (18 μL, 0.079 mmol) was added slowly to the reaction mixture. After stirring 1 h, the reaction mixture was quenched with Et$_3$N. The mixture was filtered and concentrated in vacuo. The residue was purified by column chromatography on silica gel (Hexanes/EtOAc=2.8/1) to give the intermediate monosaccharide. Said monosaccharide was dissolved in dry MeOH/CH$_2$Cl$_2$ (3 mL, v/v=1/1). A solution of NaOMe (0.09 mL, 0.5 M) was added and the reaction mixture was stirred overnight at r.t. Then, the reaction was concentrated in vacuo and the residue was purified by column chromatography on silica gel (Hexanes/EtOAc=2.8/1 to 1/1) to give alcohol 19* (102 mg, 53% for two steps). $[\alpha]_D^{25}$=−23.36 (c=1.02, CHCl$_3$); $^1$H NMR (400 MHz, CDCl$_3$) δ 7.27-7.09 (m, 20H), 5.07 (d, J=12.4 Hz, 2H), 4.78 (dd, J=2.4, 10.8 Hz, 1H), 4.67 (br, 1H), 4.59 (br, 2H), 4.52 (dd, J=2.4, 11.2 Hz, 1H), 4.39 (d, J=9.2 Hz, 2H), 3.92 (br, 1H), 3.73 (m, 1H), 3.61 (br, 1H), 3.50 (m, 1H), 3.36 (t, J=9.2 Hz, 1H), 3.24-3.10 (m, 3H), 1.44 (m, 4H), 1.22 (d, J=6.0 Hz, 3H), 1.18 (m, 2H); $^{13}$C NMR (101 MHz, CDCl$_3$) δ 156.7, 156.1, 138.3, 138.0, 137.9, 136.8, 136.7, 128.5, 128.5, 128.4, 128.0, 127.9, 127.8, 127.8, 127.7, 127.3, 127.2, 98.9, 80.1, 80.0, 75.4, 71.9, 68.5, 67.2, 67.2, 50.5, 50.2, 47.1, 46.1, 29.1, 27.9, 27.5, 23.4, 17.9; HRMS (ESI): calcd for $C_{40}H_{47}NO_7Na$ [M+Na]$^+$: 676.3250, found: 676.3265.

Example A-16: Synthesis of N-(Benzyl)benzyloxy-carbonyl-5-amino-pentanyl 3,4-di-O-benzyl-α-L-rhamnopyranosyl-(1→2)-3,4-di-O-benzyl-α-L-rhamnopyranoside (20*)

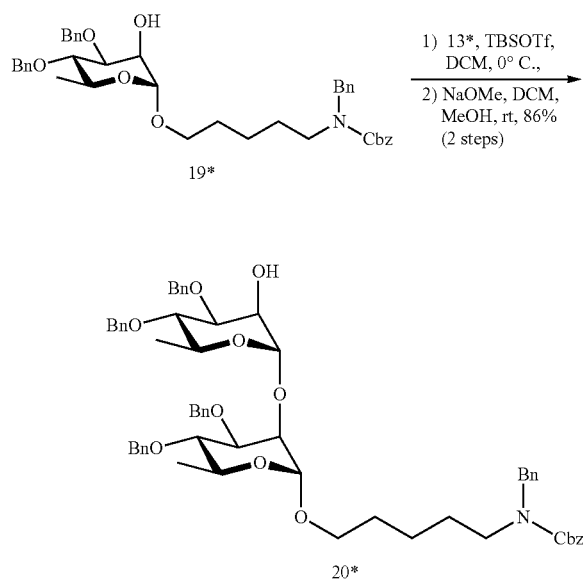

Acceptor 19* (303 mg, 0.46 mmol) and the donor 13* (369 mg, 0.69 mmol) were dissolved in dry CH$_2$Cl$_2$ (4.5 mL). 4 Å MS (600 mg) were added. The mixture was stirred at r.t. for 30 min and then cooled to 0° C. TBSOTf (21 µL, 0.093 mmol) was added slowly to the reaction mixture. After stirring 1 h, the reaction was quenched with Et$_3$N. The mixture was filtered and concentrated in vacuo. The residue was purified by column chromatography on silica gel (Hexanes/EtOAc=2.8/1) to give the intermediate disaccharide. Said disaccharide was dissolved in CH$_2$Cl$_2$/MeOH (2 mL, v/v=1/1). NaOMe (50 mg, 0.93 mmol) was added. The mixture was stirred overnight at r.t. The reaction mixture was quenched with acid resin, and concentrated in vacuo. The residue was purified by column chromatography on silica gel (Hex/EA=2/1) to afford alcohol 20* (389 mg, 86%). $[\alpha]_D^{25}$=−20.34 (c=0.88, CHCl$_3$);); $^1$H NMR (400 MHz, CDCl$_3$) δ 7.27-7.09 (m, 30H), 5.07 (d, J=12.8 Hz, 2H), 5.00 (br, 1H), 4.79 (d, J=6.8 Hz, 1H), 4.77 (d, J=6.8 Hz, 1H), 4.62 (s, 2H), 4.60-4.56 (m, 3H), 4.52 (d, J=4.0 Hz, 1H), 4.39 (d, J=9.6 Hz, 2H), 4.05 (m, 1H), 3.90 (br, 1H), 3.79 (dd, J=7.2, 9.2 Hz, 1H), 3.76-3.70 (m, 2H), 3.55 (m, 1H), 3.46 (m, 1H), 3.39 (t, J=9.2 Hz, 1H), 3.29 (t, J=9.6 Hz, 1H), 3.23-3.09 (m, 3H), 1.41 (m, 4H), 1.21 (d, J=6.4 Hz, 3H), 1.19 (d, J=6.0 Hz, 3H), 1.16 (m, 2H); $^{13}$C NMR (101 MHz, CDCl$_3$) δ 156.7, 156.2, 138.5, 138.4, 138.3, 138.0, 137.9, 128.8, 128.6, 128.5, 128.4, 128.4, 128.2, 128.2, 128.0, 128.0, 128.0, 127.9, 127.8, 127.7, 127.3, 127.2, 100.7, 98.8, 80.4, 80.0, 79.9, 79.5, 75.4, 74.7, 72.2, 72.2, 68.7, 67.9, 67.8, 67.2, 50.5, 50.2, 47.1, 46.1, 29.2, 28.0, 27.6, 23.4, 18.1, 18.0; HRMS (ESI): calcd for C$_{60}$H$_{69}$NO$_{11}$Na [M+Na]$^+$: 1002.4768, found: 1002.4791.

Example A-17: Synthesis of N-(Benzyl)benzyloxy-carbonyl-5-amino-pentanyl 3,4-di-O-benzyl-α-L-rhamnopyranosyl-(1→2)-3,4-di-O-benzyl-α-L-rhamnopyranosyl-(1→2)-3,4-di-O-benzyl-α-L-rhamnopyranoside (21*)

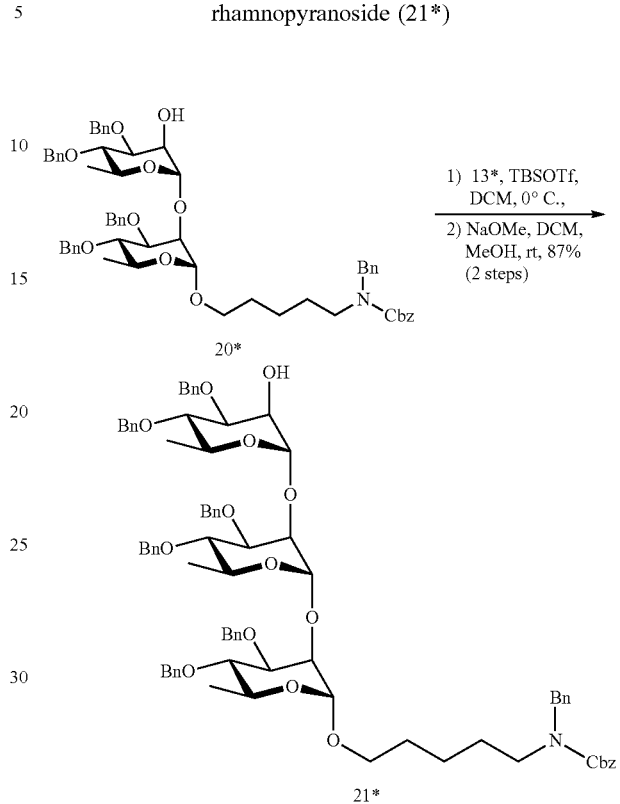

Acceptor 20* (389 mg, 0.39 mmol) and donor 13* (316 mg, 0.59 mmol) were dissolved in dry CH$_2$Cl$_2$ (4 mL). 4 Å MS (650 mg) were added. The mixture was stirred at r.t. for 30 min and then cooled to 0° C., followed by slow addition of TBSOTf (18 µL, 0.079 mmol). After 1 h of stirring at 0° C., the reaction mixture was quenched with Et$_3$N. The mixture was filtered and concentrated in vacuo. The residue was purified by column chromatography on silica gel (Hexanes/EtOAc=2.8/1) to give the intermediate trisaccharide. Said trisaccharide was dissolved in CH$_2$C$_2$/MeOH (2 mL, v/v=1/1). NaOMe (43 mg, 0.79 mmol) was added. The mixture was stirred overnight at r.t., then the reaction mixture was quenched with acid resin, and concentrated in vacuo. The residue was purified by column chromatography on silica gel (Hexanes/EtOAc=2.5/1) to afford alcohol 21* (449 mg, 87%). $[\alpha]_D^{25}$=−25.55 (c=1.00, CHCl$_3$); $^1$H NMR (400 MHz, CDCl$_3$) δ 7.44-7.21 (m, 40H), 5.23 (d, J=12.4 Hz, 2H), 5.19 (br, 1H), 5.14 (br, 1H), 4.95-4.90 (m, 3H), 4.76-4.62 (m, 9H), 4.55 (d, J=9.6 Hz, 2H), 4.19 (br, 2H), 3.96-3.78 (m, 7H), 3.65-3.37 (m, 6H), 3.34-3.21 (m, 3 H), 1.56-1.45 (m, 4H), 1.42 (m, 2H), 1.36 (d, J=6.0 Hz, 3H), 1.32 (d, J=6.0 Hz, 3H), 1.27 (d, J=6.0 Hz, 3H); $^{13}$C NMR (101 MHz, CDCl$_3$) δ 156.7, 156.2, 138.5, 138.4, 138.3, 138.3, 138.0, 137.9, 136.9, 136.8, 128.6, 128.6, 128.6, 128.5, 128.4, 128.4, 128.2, 128.1, 128.0, 128.0, 127.9, 127.9, 127.8, 127.7, 127.7, 127.6, 127.3, 127.2, 100.5, 100.5, 98.8, 80.4, 80.3, 80.1, 79.7, 79.6, 79.2, 75.5, 75.3, 74.6, 74.5, 72.4, 72.2, 72.0, 68.8, 68.4, 68.0, 67.9, 67.2, 50.5, 50.2, 47.1, 46.1, 29.7, 29.2, 28.0, 27.6, 23.4, 18.1, 18.1, 17.9; HRMS (ESI): calcd for C$_{80}$H$_{91}$NO$_{15}$Na [M+Na]$^+$: 1328.6286, found: 1328.6217.

Example A-18: Synthesis of N-(Benzyl)benzyloxy-carbonyl-5-amino-pentanyl 2-O-acetyl-3,4-di-O-benzyl-α-L-rhamnopyranosyl-(1→4)-[2-O-acetyl-3,4,6-tri-O-benzyl-β-D-galactopyranosyl-(1→3)]-(methyl 2-O-benzyl-α-D-galactopyranosyluronate)-(1→2)-3,4-di-O-benzyl-α-L-rhamnopyranosyl-(1→2)-3,4-di-O-benzyl-α-L-rhamnopyranosyl-(1→2)-3,4-di-O-benzyl-α-L-rhamnopyranoside (22*)

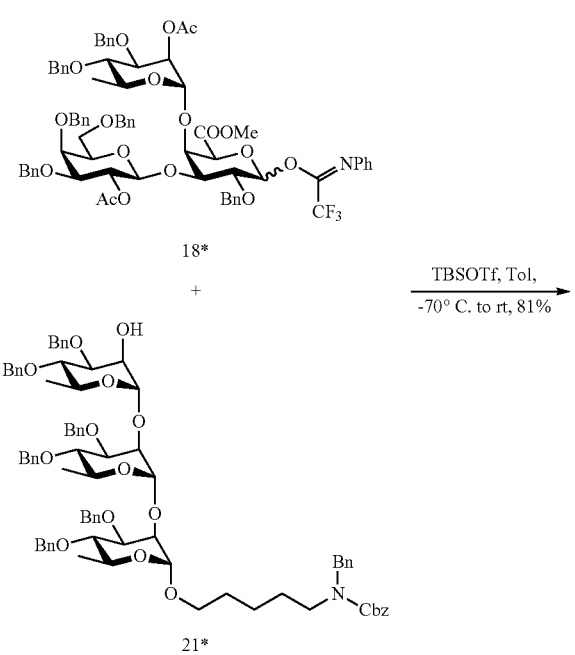

N-phenyltrifluoroacetimidate 18* (65 mg, 0.050 mmol) and trisaccharide acceptor 21* (32 mg, 0.025 mmol) were dissolved in Tol/Et$_2$O (1.1 mL, v/v 10/1). 4 Å MS (100 mg) were added. The mixture was stirred at r.t. for 20 min, and then cooled to −70° C. TBSOTf solution in toluene (0.10 mL, 0.05 M) was added slowly. After stirring at −70° C. for 3 h, the reaction mixture was slowly warmed to r.t. The reaction mixture was quenched with Et$_3$N. The reaction mixture was filtered and concentrated in vacuo. The residue was purified by column chromatography on silica gel (Toluene/EtOAc=10/1) to give hexasaccharide α isomer 22* (48.8 mg, 81%) and β isomer 22* (10.2 mg, 17%). Hexasaccharide α isomer 22*: $[α]_D^{25}$=15.01 (c=0.11, CHCl$_3$); $^1$H NMR (400 MHz, CDCl$_3$) δ 7.35-7.09 (m, 70H), 5.56 (br, 1H), 5.39-5.35 (m, 2H), 5.17 (d, J=10.0 Hz, 2H), 5.09 (br, 1H), 4.98 (br, 1H), 4.95-4.77 (m, 8H), 4.73-4.66 (m, 3H), 4.63-4.53 (m, 11H), 4.48-4.28 (m, 9H), 4.18-4.11 (m, 3H), 4.09 (m, 1H), 3.89-3.84 (m, 4H), 3.82 (d, J=3.2 Hz, 1H), 3.80-3.74 (m, 3H), 3.73-3.68 (m, 2H), 3.67-3.61 (m, 2H), 3.58-3.53 (m, 3H), 3.51-3.48 (m, 2H), 3.47 (s, 3H), 3.42 (dd, J=2.8, 10.0 Hz, 1H), 3.37-3.32 (m, 2H), 3.31 (m, 1H), 3.28-3.15 (m, 5H), 2.01 (s, 3H), 1.83 (s, 3H), 1.50-1.41 (m, 4H), 1.33-1.15 (m, 14H); $^{13}$C NMR (151 MHz, CDCl$_3$) δ 169.9, 169.2, 169.0, 139.2, 138.8, 138.6, 138.4, 138.0, 137.9, 128.6, 128.5, 128.5, 128.5, 128.4, 128.4, 128.4, 128.3, 128.2, 128.2, 128.1, 128.0, 128.0, 127.9, 127.8, 127.8, 127.7, 127.7, 127.6, 127.5, 127.4, 127.3, 127.3, 113.6, 102.4, 100.6, 98.8, 98.7, 98.5, 96.9, 80.7, 80.5, 80.4, 80.3, 79.7, 79.5, 79.1, 78.5, 78.4, 76.6, 75.5, 75.3, 74.8, 74.6, 74.6, 74.4, 74.2, 73.8, 73.7, 72.9, 72.4, 72.3, 72.0, 72.0, 71.9, 71.7, 71.4, 70.6, 68.9, 68.7, 68.6, 68.4, 68.1, 67.9, 67.3, 67.3, 52.2, 32.0, 31.9, 29.8, 29.5, 29.2, 23.5, 22.8, 21.1, 20.9, 18.2, 18.1, 18.1, 14.2, 1.1; HRMS (ESI): calcd for C$_{145}$H$_{161}$O$_{32}$NNa [M+Na]$^+$: 2451.0899, found: 2451.0881.

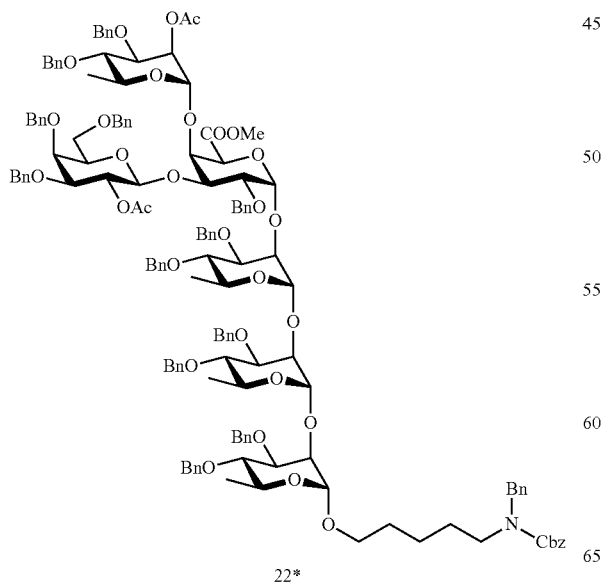

Example A-19: Synthesis of 5-Amino-pentanyl α-L-rhamnopyranosyl-(1→4)-[P3-D-galactopyranosyl-(1→3)]-α-D-galactopyranosyluronic acid-(1→2)-α-L-rhamnopyranosyl-(1→2)-α-L-rhamnopyranosyl-(1→2)-α-L-rhamnopyranoside (23*)

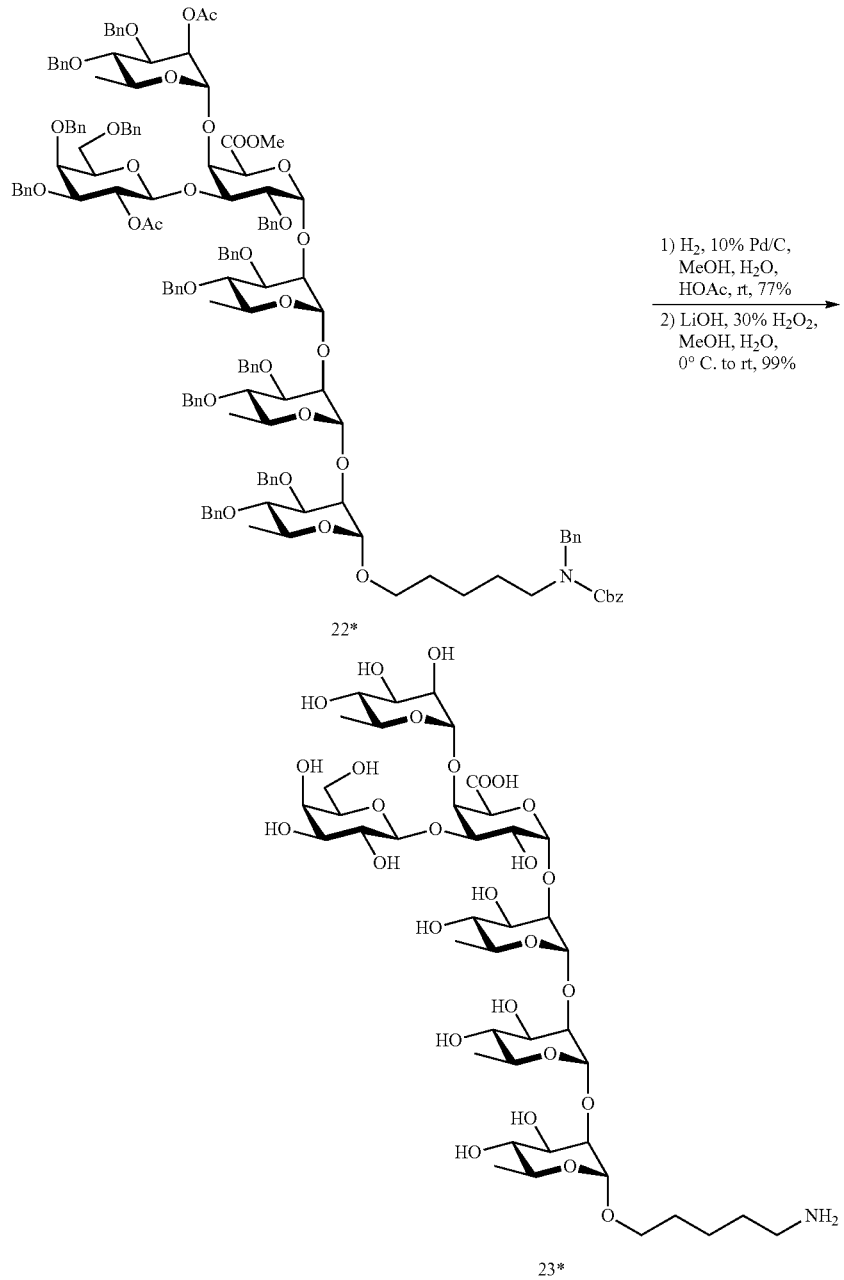

A mixture of hexasaccharide 22* (32 mg, 0.013 mmol) and Pd/C (143 mg, 10%) in MeOH/H₂O/HOAc (140/10/1, v/v/v, 7.55 mL) was stirred overnight at r.t. under H$_2$ atmosphere. After stirring 24 h, the reaction mixture was filtered and concentrated in vacuo. The residue was purified by Sephadex LH-20 column (MeOH/H$_2$O=8/1) to give the benzyl deprotected hexasaccharide (10 mg, 77%). The above hexasaccharide (6 mg, 5.34 ummol) was dissolved in MeOH and water (1 mL, v/v=1/1) and cooled to 0° C. Premixed solution of 1M LiOH (0.27 mL, 0.27 mmol) and 30% H$_2$O$_2$ (0.12 mL, 1.17 mmol) was added. The reaction mixture was allowed to warm to r.t. After 8 h, the reaction was neutralized with AcOH (18 uL, 0.32 mmol) and concentrated in vacuo. The residue was purified by Sep-Pak C18 (H$_2$O, 10% MeOH, 25% MeOH, 50% MeOH) to give target hexasaccharide 23* (5.4 mg, 99%) as a white solid. $[\alpha]_D^{25}$=8.36 (c=0.11, H$_2$O); $^1$H NMR (400 MHz, D$_2$O) δ 5.41 (br, 1H), 5.10 (br, 1H), 5.07 (br, 1H), 5.06 (br, 1H), 4.85 (br, 1H), 4.66 (br, 2H), 4.58 (d, J=8.0 Hz, 1H), 4.20 (dd, J=2.8, 10.8 Hz, 1H), 4.12 (m, 1H), 4.11 (m, 1H), 4.08 (m, 1H), 4.06 (m, 1H), 3.90 (m, 3H), 3.86 (m, 2H), 3.81 (m, 1H), 3.78 (m, 1H), 3.75 (m, 1H), 3.73 (m, 2H), 3.71 (m, 1H), 3.69 (m, 1H), 3.68 (m, 2H), 3.66 (m, 1H), 3.58 (m, 1H), 3.53 (m, 1H), 3.49 (m, 2H), 3.46 (m, 1H), 3.36 (t, J=9.6 Hz, 1H), 2.98 (t, J=7.6 Hz, 2H), 1.71-1.60 (m, 4H), 1.47-1.38 (m, 2H), 1.29 (m, 9H), 1.21 (d, J=6.0 Hz, 3H); $^{13}$C NMR (151 MHz, D$_2$O) δ 176.4, 106.4, 102.4, 101.4, 101.2, 99.9, 98.9, 81.4, 80.2, 80.1, 78.1, 77.1, 76.8, 74.2, 73.8, 73.7, 73.6, 73.3, 73.0, 72.9, 71.9, 71.7, 71.7, 71.4, 70.9, 70.9, 70.4, 70.3, 70.3, 69.2, 68.8, 62.7, 40.9, 29.5, 28.1, 24.0, 18.2, 18.2, 18.2, 18.1; HRMS (ESI): calcd for C$_{41}$H$_{71}$O$_{28}$NNa [M+Na]$^+$: 1048.4060, found: 1048.4002.

Example A-20: Synthesis of 2-O-acetyl-3,4-di-O-benzyl-α-L-rhamnopyranosyl-(1→4)-(methyl 2-O-benzyl-3-O-levulinoyl-D-galactopyranosid)uronate 1-N-phenyltrifluoroacetimidate (24*)

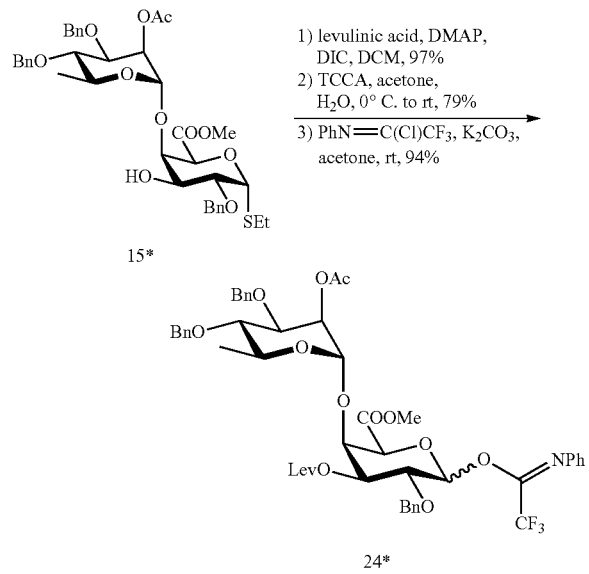

Alcohol 15* (136 mg, 0.19 mmol) was dissolved in CH$_2$Cl$_2$ (2 mL). Levulinic acid (0.1 mL, 0.96 mmol), 4-dimethylaminopyridine (140 mg, 1.15 mmol) and di-isopropylcarbodiimide (0.15 mL, 0.96 mmol) were added. The reaction mixture was stirred at r.t. overnight. The mixture was diluted with CH$_2$Cl$_2$, washed with brine and then concentrated in vacuo. The crude product was purified by chromatography column on silica gel (Hexanes/EtOAc=1:1) to afford the levulinate ester (150 mg, 97%). The levulinate ester (161 mg, 0.199 mmol) was dissolved in acetone and water (6.25 mL, v/v=4/1) at 0° C. TCCA (46 mg, 0.199 mmol) was added. The reaction mixture was allowed to warm to r.t. overnight. The reaction mixture was diluted with ethyl acetate, washed with sat NaHCO$_3$ and brine. The organic layer was dried over MgSO$_4$, filtered and concentrated in vacuo. The residue was purified by column chromatography on silica gel (Hexanes/EtOAc=1/2) to give the hemiacetal (121 mg, 79%). To a solution of hemiacetal (121 mg, 0.158 mmol) in acetone (3 mL) was added K$_2$CO$_3$ (66 mg, 0.48 mmol) and PhN=C(Cl)CF$_3$ (98 mg, 0.48 mmol). The mixture was stirred overnight at r.t. The solution was filtered and concentrated in vacuo. The residue was purified by column chromatography on silica gel (Hexanes/EtOAc=2.2/1 to 1/1) to give the imidate 24* (139 mg, 94%). [α]$_D^{25}$=59.57 (c=0.25, CHCl$_3$); $^1$H NMR (400 MHz, CDCl$_3$) δ 7.31-7.25 (m, 16H), 7.19 (m, 1H), 7.09 (m, 1H), 6.73 (m, 3H), 5.42 (brs, 1H), 5.31 (dd, J=2.0, 10.8 Hz, 1H), 4.97 (br, 1H), 4.86 (d, J=10.8 Hz, 1H), 4.74-4.56 (m, 6H), 4.37 (d, J=11.2 Hz, 1H), 4.01 (dd, J=2.8, 10.4 Hz, 1H), 3.79 (s, 3H), 3.77 (m, 1H), 3.68 (m, 1H), 3.36 (t, J=9.6 Hz, 1H), 2.89-2.69 (m, 3H), 2.52 (m, 1H), 2.18 (s, 3H), 2.11 (s, 3H), 1.29 (d, J=6.4 Hz, 3H); $^{13}$C NMR (101 MHz, CDCl$_3$) δ 206.31, 172.54, 170.44, 167.16, 143.40, 138.75, 138.08, 137.33, 128.88, 128.64, 128.53, 128.38, 128.23, 128.20, 127.89, 127.76, 127.67, 127.61, 124.44, 119.45, 100.57, 79.70, 77.76, 77.31, 75.19, 73.11, 72.07, 72.01, 71.75, 71.18, 68.94, 68.86, 52.79, 37.97, 29.81, 27.86, 21.27, 18.08; HRMS (ESI): calcd for C$_{49}$H$_{52}$F$_3$NO$_{14}$Na [M+Na]$^+$: 958.3238, found: 958.3303.

Example A-21: Synthesis of N-(Benzyl)benzyloxycarbonyl-5-amino-pentanyl 2-O-acetyl-3,4-di-O-benzyl-α-L-rhamnopyranosyl-(1→4)-(methyl 2-O-benzyl-3-levulinoyl-α-D-galactopyranosid)uronate (25*)

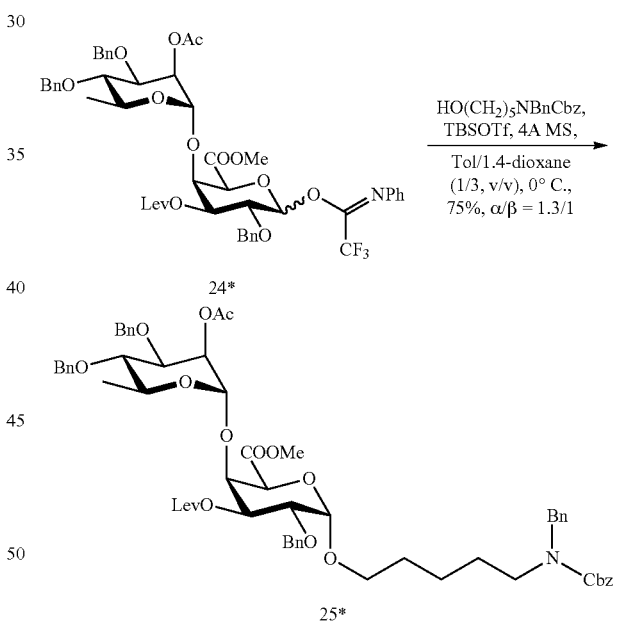

Donor 24* (139 mg, 0.149 mmol) and the linker (49 mg, 0.149 mmol) were dissolved in a mixture toluene/1,4-dioxane (4 mL, ⅓). 4 Å MS (200 mg) were added. The reaction mixture was stirred at r.t. for 20 min and then cooled to 0° C. TBSOTf (7 μL, 0.03 mmol) in toluene was slowly added. The reaction was stirred at 0° C. After 3 h, the reaction was quenched with Et$_3$N and filtered, then concentrated in vacuo. The residue was purified by column chromatography on silica gel (Hexanes/EtOAc=1/1 to 1/2) to give the disaccharide 25* (119 mg, 75%, α/β=1.3/1). α isomer 25*: [α]D$_{25}$=33.46 (c=0.20, CHCl$_3$); $^1$H NMR (400 MHz, CDCl$_3$) δ 7.36-7.17 (m, 30H), 5.46 (m, 1 H), 5.30 (dd, J=2.8, 10.8 Hz, 1H), 5.18 (m, 3H), 4.94 (d, J=1.6 Hz, 1H), 4.89 (m, 2H), 4.67 (m, 1H), 4.61-4.55 (m, 2H), 4.51-4.41 (m, 5H), 3.88 (dd, J=3.6, 10.4 Hz, 1H), 3.84 (dd, J=3.2, 9.6 Hz, 1H), 3.75 (s, 3H), 3.68 (m, 1H), 3.61 (m, 1H), 3.54 (m, 1H), 3.36 (t, J=9.6 Hz, 1H), 3.29 (m, 1H), 3.19 (m, 1H), 2.87-2.66 (m, 3H), 2.55-2.48 (m, 1H), 2.16 (s, 3H), 2.11 (s, 3H), 1.51 (m, 4H), 1.34 (m, 2H), 1.27 (d, J=6.0 Hz, 3H); $^{13}$C NMR (101 MHz, cdcl$_3$) δ 206.2, 172.4, 170.4, 168.2, 138.8, 138.1, 137.9, 137.9, 128.6, 128.5, 128.4, 128.2, 128.1, 128.0, 127.9, 127.9, 127.7, 127.5, 127.4, 127.3, 100.1, 97.5, 79.7, 77.7, 77.6, 75.0, 72.9, 72.6, 71.9, 71.5, 69.6, 68.9, 68.7, 67.2, 52.5, 37.9, 32.3, 29.7, 29.1, 27.8, 23.4, 21.2, 18.0; HRMS (ESI): calcd for C$_{61}$H$_{71}$NO$_{16}$Na [M+Na]$^+$: 1096.4671, found: 1096.4595.

Example A-22: Synthesis of N-(Benzyl)benzyloxy-carbonyl-5-amino-pentanyl 2-O-acetyl-3,4-di-O-benzyl-α-L-rhamnopyranosyl-(1→4)-(methyl 2-O-benzyl-α-D-galactopyranosid)uronate (26*)

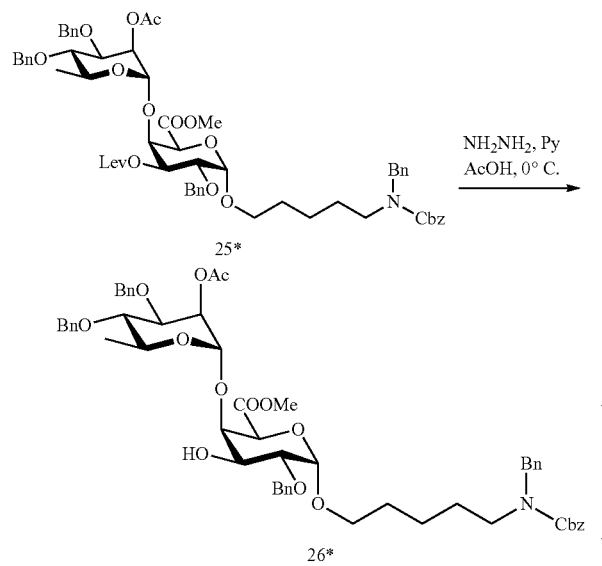

Levulinate ester 25* (52 mg, 48 umol) was dissolved in pyridine (2 mL) and cooled to 0° C. Subsequently, a solution of NH$_2$NH$_2$ (1 M in 3:2 Pyridine.AcOH, 0.2 mL) was added. The mixture was stirred at r.t. After 4 h of stirring, the reaction was quenched by the addition of acetone (2 mL) and the solvents were removed in vacuo. The crude product was purified by silica gel flash column chromatography (Hexanes/EtOAc=1.3/1) to give the product 26* (46 mg, 97%). [α]$_D^{25}$=28.84 (c=0.14, CHCl$_3$); $^1$H NMR (400 MHz, CDCl$_3$) δ 7.36-7.17 (m, 30H), 5.51 (br, 1H), 5.19 (m, 3H), 4.90 (m, 2H), 4.69-4.57 (m, 4H), 4.50-4.38 (m, 5H), 4.12 (m, 1H), 3.86 (dd, J=3.2, 9.2 Hz, 1H), 3.77 (s, 3H), 3.74 (m, 1H), 3.65-3.58 (m, 2H), 3.55 (m, 1H), 3.37 (t, J=9.6 Hz, 1H), 3.25 (m, 1H), 3.18 (m, 1H), 2.13 (s, 3H), 1.55-1.45 (m, 4H), 1.31 (m, 2H), 1.29 (d, J=6.0 Hz, 3H); $^{13}$C NMR (101 MHz, CDCl$_3$) δ 170.3, 168.8, 138.9, 138.2, 137.9, 137.7, 128.7, 128.6, 128.5, 128.4, 128.3, 128.3, 128.2, 128.1, 128.0, 127.9, 127.7, 127.6, 127.5, 127.2, 99.4, 96.9, 79.7, 78.0, 77.3, 76.2, 75.9, 75.0, 72.8, 71.9, 70.1, 69.5, 68.8, 68.4, 67.3, 52.6, 29.8, 29.2, 23.5, 21.3, 18.1; HRMS (ESI): calcd for C$_{56}$H$_{65}$NO$_{14}$Na [M+Na]$^+$: 998.4303, found: 998.4289.

Example A-23: Synthesis of N-(Benzyl)benzyloxy-carbonyl-5-amino-pentanyl 2-O-acetyl-3,4-di-O-benzyl-α-L-rhamnopyranosyl-(1→4)-[2-O-acetyl-3,4,6-tri-O-benzyl-β-D-galactopyranosyl-(1→3)]-(methyl 2-O-benzyl-D-galactopyranosid)uronate (27*)

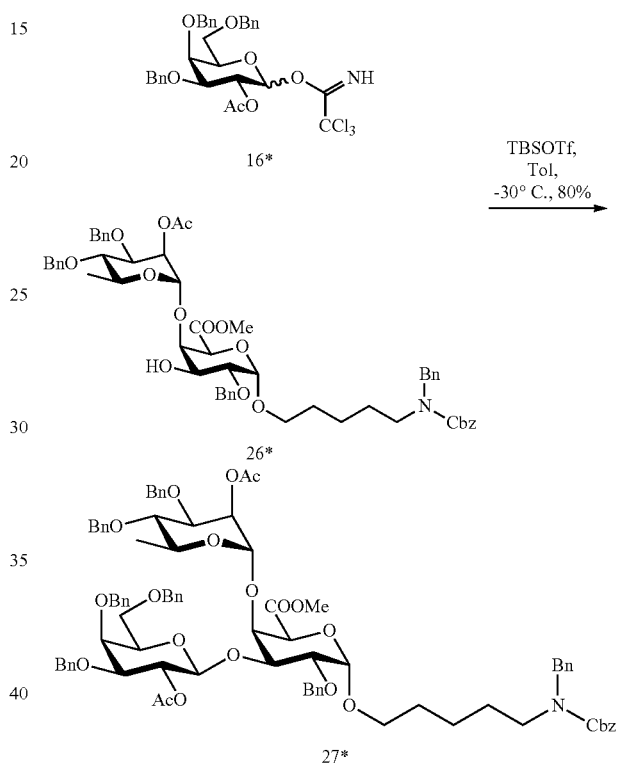

Disaccharide acceptor 26* (20 mg, 0.020 mmol) and monosaccharide donor 16* (52 mg, 0.082 mmol) were dissolved in dry toluene (1 mL). 4 Å MS (100 mg) were added. The reaction mixture was stirred at r.t. for 30 min, then cooled to −30° C. TBSOTf (0.1 mL, 0.08 M) in toluene was added slowly. The reaction mixture was allowed to warm to r.t. After 3 h of stirring, the mixture was quenched with Et$_3$N. The mixture was filtered and concentrated in vacuo. The residue was purified by column chromatography on silica gel (Hex/EA=1.8/1) to give the trisaccharide 27* (24 mg, 80%). [α]$_D^{25}$=6.74 (c=0.11, CHCl$_3$); $^1$H NMR (400 MHz, CDCl$_3$) δ 7.35-7.22 (m, 40H), 5.52 (br, 1H), 5.40 (br, 1H), 5.37 (dd, J=8.0, 10.0 Hz, 1H), 5.16 (m, 2H), 4.96 (d, J=12.0 Hz, 1H), 4.89 (d, J=11.6 Hz, 1H), 4.78-4.72 (m, 4H), 4.66-4.41 (m, 11H), 4.35 (m, 1H), 4.16 (m, 1H), 3.91 (m, 1H), 3.87 (dd, J=3.6, 10.4 Hz, 1H), 3.82 (dd, J=3.2, 9.2 Hz, 1H), 3.72 (s, 3H), 3.64-3.49 (m, 5H), 3.47 (dd, J=2.4, 10.0 Hz, 1H), 3.35 (m, 2H), 3.24 (m, 1H), 3.16 (m, 1H), 2.05 (s, 3H), 1.97 (s, 3H), 1.57-1.45 (m, 4H), 1.27 (m, 2H), 1.26 (d, J=5.6 Hz, 3H); $^{13}$C NMR (101 MHz, CDCl$_3$) δ 170.1, 169.1, 168.9, 139.1, 138.7, 138.5, 138.0, 128.7, 128.6, 128.5, 128.5, 128.3, 128.3, 128.3, 128.2, 128.1, 128.1, 127.9, 127.9, 127.9, 127.8, 127.6, 127.5, 127.5, 127.3, 102.2, 98.5, 97.7, 80.3, 79.6, 78.5, 77.3, 76.6, 76.2, 74.7, 74.4, 74.4, 73.7, 73.6, 73.5, 72.8, 72.0, 71.8, 71.2, 70.3, 68.7, 68.3, 68.1, 67.3, 52.6, 29.8, 23.3, 21.2, 21.0, 18.1; HRMS (ESI): calcd for $C_{85}H_{95}NO_{20}Na$ [M+Na]$^+$: 1472.6345, found: 1472.6374.

Example A-24: Synthesis of 5-amino-pentanyl α-L-rhamnopyranosyl-(1→4)-α-D-galactopyranosyluronic acid (28*)

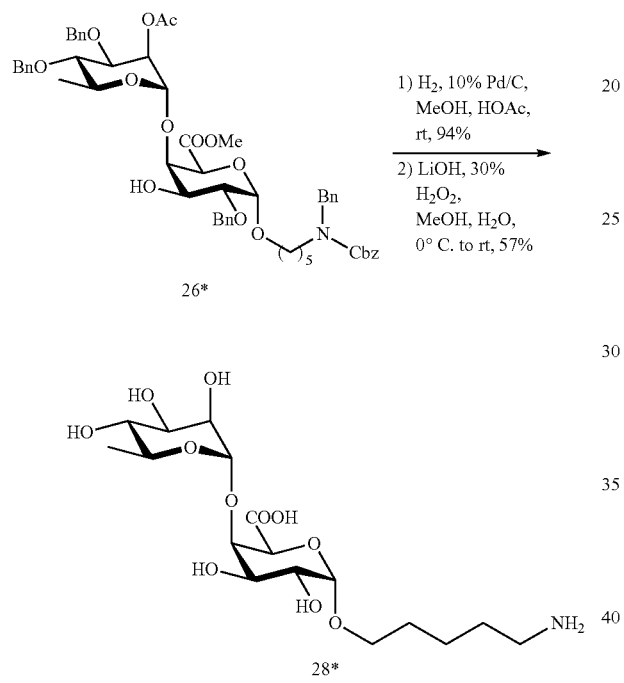

Disaccharide 26* (13 mg, 0.013 mmol) was dissolved in MeOH and HOAc (100/1, 5.05 mL). Pd/C (56.7 mg, 10%) was added. The reaction mixture was stirred under $H_2$ atmosphere at r.t. After 24 h of stirring, the reaction mixture was filtered and concentrated in vacuo. The residue was purified by LH-20 (MeOH) to give the product (6 mg, 94%). The above disaccharide (6 mg, 12 ummol) was dissolved in MeOH and water (2 mL, v/v=1/1) and cooled to 0° C. Premixed solution of 1M LiOH (0.62 mL, 0.62 mmol) and 30% $H_2O_2$ (0.28 mL, 2.74 mmol) was added. The reaction mixture was allowed to warm to r.t. After 8 h of stirring, the reaction was neutralized with AcOH (43 μL, 0.75 mmol) and concentrated in vacuo. The residue was purified by Sep-pak® C18 ($H_2O$, 10% MeOH, 25% MeOH, 50% MeOH) to give the product 28* (3 mg, 57%). $[α]_D^{25}$=51.50 (c=0.03, $H_2O$); $^1$H NMR (400 MHz, $D_2O$) δ 5.20 (d, J=2.4 Hz, 1H, H-1'), 4.93 (d, J=3.6 Hz, 1H, H-1), 4.36 (br, 1H, H-4), 4.19 (m, 1H, H-5), 4.03 (m, 1H, H-2'), 4.01 (m, 1H, H-3), 3.09 (m, 1H, H-2), 3.79-3.72 (m, 2H, H-3', H-5'), 3.65 (m, 1H, OCH$_2$), 3.53 (m, 1H, OCH$_2$), 3.32 (t, J=9.6 Hz, 1H, H-4'), 3.13 (m, 1H, NCH$_2$), 2.96 (t, J=7.6 Hz, 1H, NCH$_2$), 1.65- 1.55 (m, 4H, CCH$_2$C), 1.46-1.33 (m, 2H, CCH$_2$C), 1.21 (d, J=6.4 Hz, 3H, H-6'); $^{13}$C NMR (151 MHz, $D_2O$) δ 177.3, 103.1, 100.9, 78.8, 74.7, 73.5, 73.3, 72.9, 72.6, 71.3, 70.6, 70.5, 41.9, 30.6, 28.9, 24.9, 19.2; HRMS (ESI): calcd for $C_{17}H_{31}NO_{11}Na$ [M+Na]$^+$: 448.1795, found: 448.1808.

Example A-25: Synthesis of 5-Amino-pentanyl α-L-rhamnopyranosyl-(1-4)-[β-D-galactopyranosyl-(1→3)]-α-D-galactopyranosyluronic acid (29*)

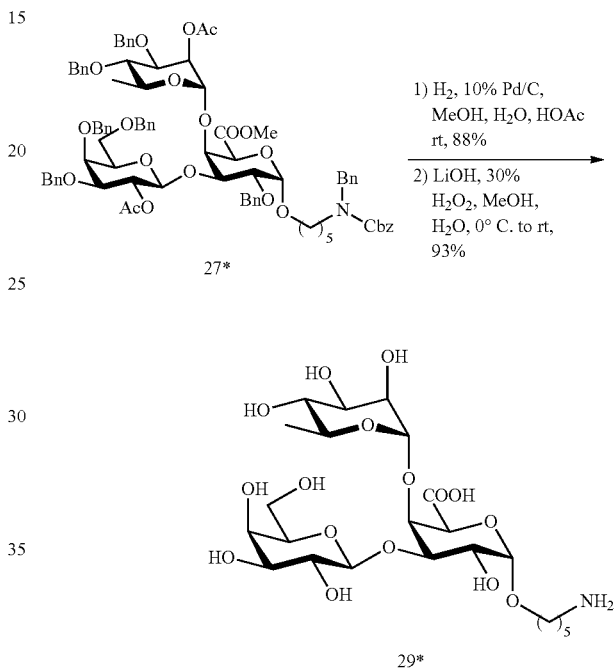

Trisaccharide 27* (12 mg, 0.013 mmol) was dissolved in MeOH, $H_2O$ and HOAc (100/1/1, 5.1 mL). Pd/C (70.4 mg, 10%) was added. The reaction mixture was stirred under $H_2$ atmosphere at r.t. After 24 h of stirring, the reaction mixture was filtered and concentrated in vacuo. The residue was purified by LH-20 (MeOH) to give the debenzylated product (5 mg, 88%). The debenzylated trisaccharide (5 mg, 7.3 mmol) was dissolved in MeOH and water (1.2 mL, v/v=1/1) and cooled to 0° C. Premixed solution of 1M LiOH (0.37 mL, 0.37 mmol) and 30% $H_2O_2$ (0.17 mL, 1.6 mmol) was added. The reaction mixture was allowed to warm to r.t. After 18 h, the reaction was neutralized with AcOH (25 μL, 0.44 mmol) and concentrated in vacuo. The residue was purified by Sephadex® LH 20 to give the product 29* (4 mg, 93%). $[α]_D^{25}$=32.62 (c=0.05, $H_2O$); $^1$H NMR (400 MHz, $D_2O$) δ 5.41 (br, 1H), 4.96 (br, 1H), 4.63 (br, 1H), 4.55 (d, J=7.6 Hz, 1H), 4.24 (br, 1H), 4.10-3.97 (m, 3H), 3.90-3.63 (m, 8H), 3.58-3.54 (m, 2H), 3.37 (t, J=10.0 Hz, 1H), 2.99 (t, J=7.6 Hz, 2H, NCH$_2$), 1.69-1.57 (m, 4H, CCH$_2$C), 1.48-1.39 (m, 2H, CCH$_2$C), 1.22 (d, J=6.0 Hz, 3H); $^{13}$C NMR (151 MHz, $D_2O$) δ 177.2, 107.5, 102.4, 100.7, 83.0, 79.0, 77.8, 75.1, 74.7, 73.9, 73.5, 72.9, 72.6, 71.4, 71.3, 70.5, 69.8, 63.8, 41.9, 30.7, 28.9, 24.9, 19.2; HRMS (ESI): calcd for $C_{23}H_{43}NO_{16}$ [M+H]$^+$: 588.2504, found: 588.2517.

Example A-26: Synthesis of Methyl (ethyl 2-O-benzyl-4-O-levulinoyl-1-thio-α-D-galactopyranosid)uronate (30*)

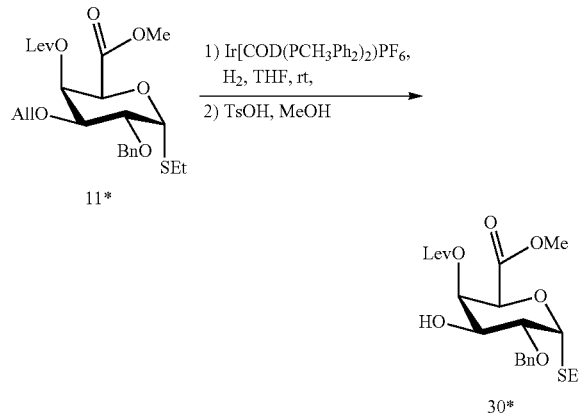

Under an argon atmosphere, a solution of Ir[COD(PCH₃Ph₂)₂]PF₆ (29.6 mg, 0.035 mmol) in THF (2.5 mL) was degassed by vacuum and gassed with H₂ balloon (~5 cycles). The reaction was stirred under H₂ atmosphere at r.t. for 20 min before the solution was degassed by vacuum and gassed with argon (~5 cycles). To this reaction flask, a solution of monosaccharide 11* (84 mg, 0.18 mmol) in THF (2.5 mL) was added via syringe in one portion at r.t. The reaction was stirred at r.t. for 3.5 h before being concentrated in vacuo. The crude product was treated with p-TsOH (7 mg, 0.035 mmol) in MeOH (2.5 mL) at r.t. After 16.5 h, the mixture was diluted with ethyl acetate, washed with sat. NaHCO₃, dried over MgSO₄, and concentrated in vacuo. The residue was purified by column chromatography on silica gel (Hexanes/EtOAc=1/2) to give the product 30* (59 mg, 77%). $[\alpha]_D^{25}$=135.61 (c=0.50, CHCl₃); ¹H NMR (400 MHz, CDCl₃) δ 7.39-7.26 (m, 5H), 5.66 (dd, J=1.2, 3.2 Hz, 1H), 5.56 (d, J=5.2 Hz, 1H), 4.93 (d, J=1.2 Hz, 1H), 4.69 (d, J=11.6 Hz, 1H), 4.59 (d, J=11.6 Hz, 1H), 4.02 (m, 1H), 3.92 (dd, J=5.2, 10.0 Hz, 1H), 3.74 (s, 3H), 2.74-2.67 (m, 3H), 2.60-2.48 (m, 4H), 2.14 (s, 3H), 1.23 (t, J=7.6 Hz, 3 H); ¹³C NMR (101 MHz, CDCl₃) δ 206.6, 172.0, 168.1, 137.3, 128.5, 128.4, 128.3, 128.2, 128.0, 83.4, 75.3, 72.4, 71.0, 69.0, 68.7, 52.7, 38.1, 29.8, 28.0, 24.2, 14.7; HRMS (ESI): calcd for C₂₁H₂₈O₈SNa [M+Na]⁺: 463.1403, found: 463.1412.

Example A-27: Synthesis of 2-O-acetyl-3,4,6-tri-O-benzyl-β-D-galactopyranosyl-(1→3)-methyl (ethyl 2-O-benzyl-4-O-levulinoyl-1-thio-α-D-galactopyranosid)uronate (31*)

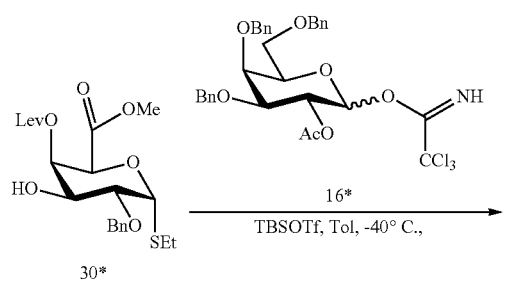

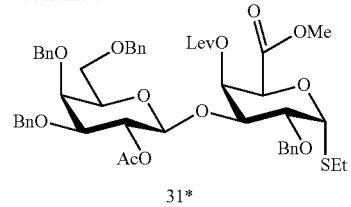

The donor 16* (286 mg, 0.45 mmol) and the acceptor 30* (59 mg, 0.13 mmol) were dissolved in toluene (1.3 mL). 4 Å MS (300 mg) were added. The mixture was stirred for 30 min at r.t., then cooled to −40° C. TBSOTf (10 μL, 0.046 mmol) was added. The reaction was allowed to warm to r.t. After 2.5 h, the reaction was quenched with Et₃N. The mixture was filtered and concentrated in vacuo. The residue was purified by column chromatography on silica gel (Hexanes/EtOAc=1.2/1) to give product 31* (92 mg, 75%). $[\alpha]_D^{25}$=83.33 (c=0.63, CHCl₃); ¹H NMR (400 MHz, CDCl₃) δ 7.36-7.28 (m, 20H), 5.62 (br, 1H), 5.41 (d, J=5.2 Hz, 1H), 5.31 (dd, J=8.0, 10.0 Hz, 1H), 4.92-4.87 (m, 2H), 4.67-4.43 (m, 8H), 4.02 (m, 1H), 3.95 (m, 2H), 3.70 (s, 3H), 3.67-3.52 (m, 3H), 3.43 (m, 1H), 2.76-2.44 (m, 6H), 2.08 (s, 3H), 1.88 (s, 3H), 1.23 (t, J=7.6 Hz, 3H); ¹³C NMR (101 MHz, CDCl₃) δ 206.6, 171.4, 169.5, 168.0, 138.6, 138.0, 137.9, 137.7, 128.5, 128.4, 128.2, 128.2, 128.0, 128.0, 127.8, 127.8, 127.5, 127.5, 101.8, 83.5, 79.9, 75.6, 74.5, 74.5, 73.6, 73.5, 73.1, 72.6, 71.8, 71.3, 70.9, 69.0, 68.3, 52.7, 38.4, 29.7, 28.2, 23.9, 21.0, 14.6; HRMS (ESI): calcd for C₅₀H₅₈O₁₄SNa [M+Na]⁺: 937.3445, found: 937.3445.

Example A-28: Synthesis of 2-O-acetyl-3,4,6-tri-O-benzyl-β-D-galactopyranosyl-(1→3)-methyl 2-O-benzyl-4-O-levulinoyl-α-D-galactopyranosid)uronate 1-N-phenyltrifluoroacetimidate (32*)

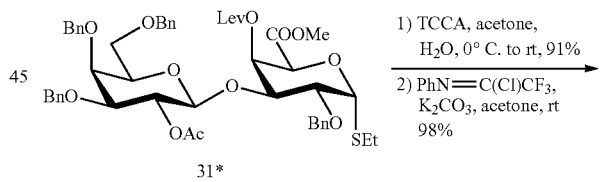

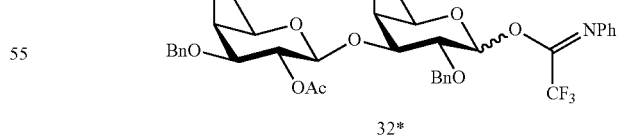

To a solution of disaccharide 31* (92 mg, 0.10 mmol) in acetone and water (4/1, 3 mL), TCCA (24 mg, 0.10 mmol) was added at 0° C. Then, the reaction was warmed gradually to r.t. After 5 h, acetone was evaporated in vacuo. The residue was diluted with ethyl acetate and washed with sat. NaHCO₃ and water. The organic layer was dried over anhydrous MgSO₄, filtered and concentrated in vacuo. The residue was purified by column chromatography (Hexanes/Ethyl Acetate=1/1.8) to give the intermediate hemiacetal (80 mg, 91%). To the above hemiacetal (80 mg, 0.092 mmol) in acetone (3 mL) was added K$_2$CO$_3$ (38 mg, 0.28 mmol) and PhN=C(Cl)CF$_3$ (57 mg, 0.28 mmol). The mixture was stirred at r.t. for 6 h. The solution was filtered and concentrated in vacuo. The residue was purified by column chromatography on silica gel (Hexanes/EtOAc=2.2/1) to give the target product 32* (94 mg, 98%).

Example A-29: Synthesis of N-(Benzyl)benzyloxycarbonyl-5-amino-pentanyl 2-O-acetyl-3,4,6-tri-O-benzyl-β-D-galactopyranosyl-(1→3)-(methyl 2-O-benzyl-D-galactopyranosid)urinate (33*)

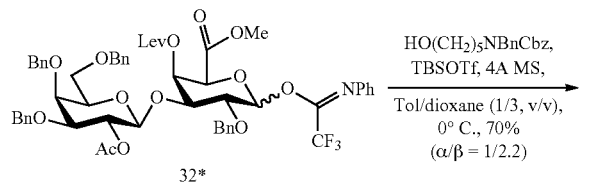

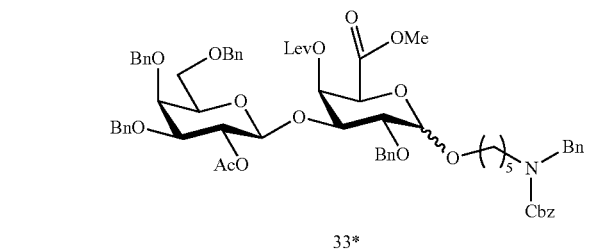

Donor 32* (44 mg, 0.042 mmol) and linker (14 mg, 0.042 mmol) was dissolved in Toluene/1,4-dioxane (1.2 mL, v/v=1/3). 4 Å MS (100 mg) was added. The reaction mixture was stirred at rt for 20 min and then cooled to 0° C. TBSOTf (0.1 mL, 0.08 M) in toluene was slowly added. The reaction mixture was stirred at 0° C. After 3 h, the reaction was quenched with Et$_3$N and filtered, then concentrated in vacuo. The residue was purified by column chromatography on silica gel (Hexanes/EtOAc=1/1 to 1/2) to give target product 33* (35 mg, 70%, α/β=1/2.2). α isomer: [α]$_D^{25}$=21.93 (c=0.18, CHCl$_3$); $^1$H NMR (400 MHz, CDCl$_3$) δ 7.36-7.14 (m, 30H), 5.55 (d, J=3.6 Hz, 1H), 5.30 (dd, J=8.0, 10.0 Hz, 1H), 5.19 (m, 3H), 4.92 (d, J=11.6 Hz, 1H), 4.83 (m, 1H), 4.68 (m, 2H), 4.58 (m, 2H), 4.51 (m, 2H), 4.45 (m, 3H), 4.29 (m, 1H), 4.06 (m, 1H), 3.95-3.90 (m, 2H), 3.81 (dd, J=3.2, 9.2 Hz, 1H), 3.72 (s, 3H), 3.63-3.54 (m, 3H), 3.48 (m, 1H), 3.42 (m, 1H), 3.29 (m, 1H), 3.13 (m, 1H), 2.79-2.53 (m, 4H), 2.09 (s, 3H), 1.83 (s, 3H), 1.56-1.46 (m, 4H), 1.33-1.29 (m, 2H); $^{13}$C NMR (101 MHz, CDCl$_3$) δ 206.7, 171.6, 169.4, 167.3, 138.6, 138.4, 138.0, 128.6, 128.6, 128.5, 128.5, 128.4, 128.3, 128.1, 128.0, 127.9, 127.9, 127.7, 127.6, 127.5, 127.4, 103.3, 101.6, 79.9, 78.8, 77.3, 75.1, 74.6, 73.6, 72.6, 72.6, 71.8, 71.4, 70.5, 68.3, 67.3, 67.2, 62.8, 60.5, 52.8, 50.6, 50.2, 47.0, 46.2, 38.3, 32.4, 29.8, 29.3, 28.2, 23.4, 23.0, 21.0, 14.3; HRMS (ESI): calcd for C$_{68}$H$_{77}$NO$_{17}$Na [M+Na]$^+$: 1202.5089, found: 1202.5129.

Example A-30: Synthesis of 5-amino-pentanyl β3-D-galactopyranosyl-(1→3)-β-D-galactopyranosyluronic acid (34β*)

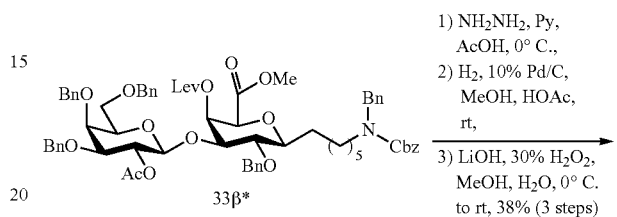

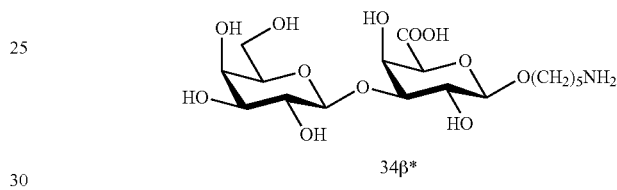

Levulinate ester 33* (20 mg, 0.017 mmol) was dissolved in pyridine (1 mL) and cooled to 0° C. Subsequently, a solution of NH$_2$NH$_2$ (1 M in 3:2 Pyridine.AcOH, 0.1 mL) was added. The mixture was stirred at rt. After 5 h, the reaction was quenched by the addition of acetone (2 mL) and the solvents were removed in vacuo. The crude product was purified by silica gel flash column chromatography (Hex/EA=1.3/1) to give the alcohol. The above alcohol was dissolved in MeOH, H$_2$O and HOAc (100/1/1, 5.1 mL). Pd/C (83 mg, 10%) was added. The reaction mixture was stirred under the atmosphere of H$_2$ at rt. After stirring 24 h, the reaction mixture was filtered and concentrated in vacuo. The residue was purified by Sephadex® LH-20 column (MeOH/H$_2$O=10/1) to give the corresponding disaccharide. The above disaccharide was dissolved in MeOH and water (1.6 mL, v/v=1/1) and cooled to 0° C. Premixed solution of 1 M LiOH (0.51 mL, 0.51 mmol) and 30% H$_2$O$_2$ (0.23 mL, 2.26 mmol) was added. The reaction mixture was allowed to warm to room temperature. After 18 h, the reaction was neutralized with AcOH (35 μL, 0.62 mmol), concentrated in vacuo. The residue was purified by Sephadex® LH-20 column to give the disaccharide 34* (2.5 mg, 38% for 3 steps) as a white solid. [α]$_D^{25}$=61.8 (c=0.02, H$_2$O); $^1$H NMR (400 MHz, D$_2$O) δ 4.61 (d, J=7.6 Hz, 1H, H-1'), 4.48 (m, 1H, H-4), 4.42 (d, J=8.0 Hz, 1H, H-1), 4.08 (m, 1H, H-5), 3.98 (m, 1H, OCH$_2$), 3.90 (m, 1H, H-4'), 3.84 (m, 1H, H-3), 3.79 (m, 1H, H-6'), 3.72 (m, 1H, H-5'), 3.69 (m, 1H, H-6'), 3.67 (m, 1H, OCH$_2$), 3.65 (m, 1H, H-2), 3.63 (m, 1H, H-3'), 3.59 (m, 1H, H-2'), 3.01 (t, J=7.6 Hz, 2H, NCH$_2$), 1.72 (m, 2H, CCH$_2$C), 1.64 (m, 2H, CCH$_2$C), 1.50 (m, 2H, CCH$_2$C); $^{13}$C NMR (151 MHz, D$_2$O) δ 106.9, 104.3, 85.2, 77.8, 77.5, 75.1, 73.6, 72.6, 72.2, 72.1, 71.2, 71.2, 63.6, 41.9, 30.5, 28.7, 24.5; HRMS (ESI): calcd for C$_{17}$H$_{31}$NO$_{12}$Na [M+Na]$^+$: 464.1744, found: 464.1723.

Example A-31: Synthesis of 5-amino-pentanyl β-D-galactopyranosyl-(1→3)-α-D-galactopyranosyluronic acid (34α*)

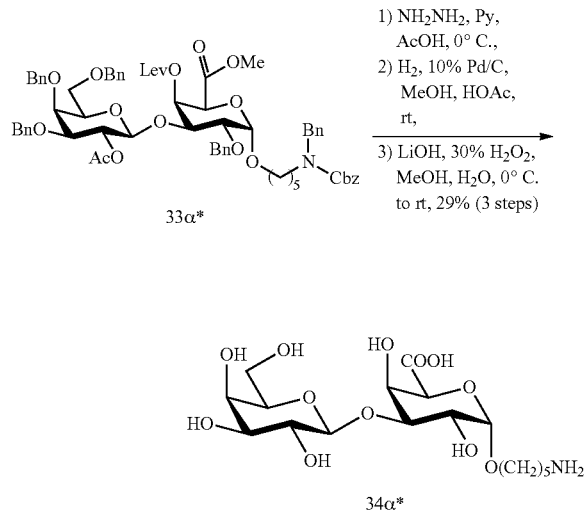

Levulinate ester 33a* (10 mg, 8.47 µmol) was dissolved in pyridine (1 mL) and cooled to 0° C. Subsequently, a solution of $NH_2NH_2$ (1 M in 3:2 Pyridine.AcOH, 0.1 mL) was added. The mixture was stirred at rt. After 5 h, the reaction was quenched by the addition of acetone (2 mL) and the solvents were removed in vacuo. The crude product was purified by silica gel flash column chromatography (Hex/EA=1.3/1) to give the intermediate secondary alcohol. The above secondary alcohol was dissolved in MeOH, $H_2O$ and HOAc (100/1/1, 5.1 mL). Pd/C (53 mg, 10%) was added. The reaction mixture was stirred under the atmosphere of $H_2$ at rt. After stirring for 24 h, the reaction mixture was filtered and concentrated in vacuo. The residue was purified by Sephadex® LH-20 column (MeOH/$H_2O$=10/1) to give the corresponding disaccharide. The disaccharide was dissolved in methanol and water (1.2 mL, v/v=1/1) and cooled to 0° C. Premixed solution of 1 M LiOH (0.17 mL, 0.17 mmol) and 30% $H_2O_2$ (0.077 mL, 0.75 mmol) was added. The reaction mixture was allowed to warm to room temperature. After 18 h, the reaction was neutralized with AcOH (12 uL, 0.21 mmol), concentrated in vacuo. The residue was purified by Sephadex® LH-20 column to give disaccharide 34α* (1.1 mg, 29% for 3 steps) as a white solid. $[\alpha]_D^{25}$=113.30 (c=0.02, $H_2O$); $^1$H NMR (400 MHz, $D_2O$) δ 4.95 (br, 1H, H-1), 4.58 (d, J=7.6 Hz, 1H, H-1'), 4.53 (br, 1H, H-4), 4.22 (br, 1H, H-5), 3.98 (m, 2H, H-2, H-3), 3.89 (m, 1H, H-4'), 3.79 (m, 1H, H-6'), 3.72 (m, 1H, H-5'), 3.68 (m, 1H, H-6'), 3.65 (m, 1H, $OCH_2$), 3.63 (m, 1H, H-3'), 3.59 (m, 1H, H-2'), 3.56 (m, 1H, $OCH_2$), 3.01 (t, J=7.6 Hz, 2H, $NCH_2$), 1.68 (m, 2H, $CCH_2C$), 1.60 (m, 2H, $CCH_2C$), 1.44 (m, 2H, $CCH_2C$); $^{13}$C NMR (151 MHz, $D_2O$) δ 178.1, 107.0, 100.7, 82.5, 77.8, 75.1, 73.7, 73.6, 73.1, 71.2, 70.5, 69.5, 63.6, 41.9, 30.7, 28.9, 25.8, 24.9; HRMS (ESI): calcd for $C_{17}H_{31}NO_{12}Na$ [M+Na]$^+$: 464.1744, found: 464.1737.

Example A-32: Synthesis of N-(Benzyl)benzyloxycarbonyl-5-amino-pentanyl 4,6-di-O-benzyl-2-O-benzoyl-3-O-fluorenylmethoxycarbonyl galactopyranoside (36*)

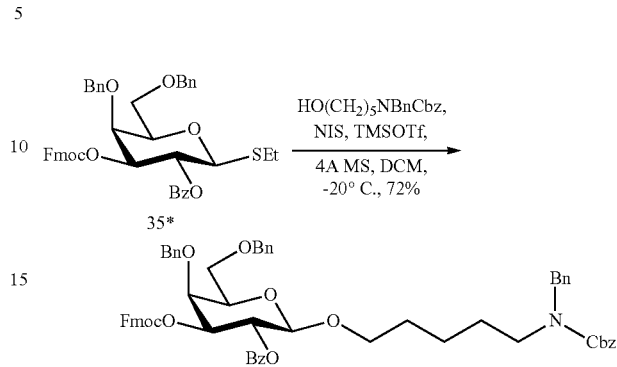

Thioglycoside 35* (117 mg, 0.16 mmol) and the linker (79 mg, 0.24 mmol) were dissolved in DCM (2 mL). 4A MS (200 mg) was added. The mixture was stirred at rt for 30 min. Then, the mixture was cooled to −20° C. NIS (47 mg, 0.21 mmol) in DCM (1 mL) was added, followed by TMSOTf (12 uL, 0.064 mmol). The reaction was allowed to warm to room temperature. After 3 h, the mixture was filtered. The solution was diluted with DCM, washed with sat.$NaHCO_3$, 1M $Na_2S_2O_3$ and brine. The mixture was filtered and concentrated in vacuo. The residue was purified by column chromatography on silica gel (petroleum ether/EtOAc=2/1) to give the monosaccharide 36* (114 mg, 72%) as a white foam. $[\alpha]_D^{25}$=15.50 (c=0.37, $CHCl_3$); $^1$H NMR (400 MHz, $CDCl_3$) δ 8.02 (d, J=6.8 Hz, 2H), 7.67 (t, J=6.8 Hz, 2H), 7.48-7.06 (m, 29H), 5.71 (dd, J=8.0, 10.4 Hz, 1H), 5.14 (br, 2H), 5.04 (dd, J=2.8, 10.4 Hz, 1H), 4.79 (d, J=11.6 Hz, 1H), 4.57-4.45 (m, 4H), 4.39-4.34 (m, 2H), 4.32-4.29 (m, 1H), 4.26 (m, 1H), 4.11-4.07 (m, 2H), 3.87 (m, 1H), 3.77 (m, 1H), 3.71-3.64 (m, 2H), 3.40 (m, 1H), 3.04 (m, 1H), 2.94 (m, 1H), 1.45-1.27 (m, 4H), 1.12 (m, 2H); $^{13}$C NMR (101 MHz, $CDCl_3$) δ 165.1, 154.6, 143.3, 142.9, 141.2, 141.1, 137.8, 137.8, 133.1, 129.8, 129.8, 128.5, 128.4, 128.3, 127.9, 127.9, 127.8, 127.2, 127.1, 125.2, 125.0, 120.0, 101.5, 77.9, 75.2, 73.8, 73.6, 73.3, 70.3, 70.1, 69.7, 69.6, 68.1, 67.1, 50.5, 50.2, 47.1, 46.5, 46.1, 29.1, 27.7, 27.3, 23.1; HRMS (ESI): calcd for $C_{62}H_{61}NO_{11}Na$ [M+Na]$^+$: 1018.4142, found: 1018.4133.

Example A-33: Synthesis of N-(Benzyl)benzyloxycarbonyl-5-amino-pentanyl 4,6-di-O-benzyl-2-O-benzoyl galactopyranoside (37*)

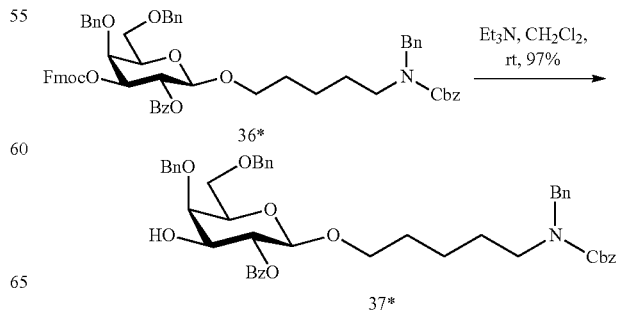

Monosaccharide 36* (37 mg, 0.037 mmol) was dissolved in DCM (1.5 mL). Et$_3$N (0.4 mL) was added. The mixture was stirred at rt. After 5 h, the mixture was diluted with toluene and concentrated in vacuo. The residue was purified by column chromatography on silica gel (Hex/EtOAc=1.8/1) to give target alcohol 37* (28 mg, 97%) as a foam. [α]$_D^{25}$=−8.52 (c=0.27, CHCl$_3$); $^1$H NMR (400 MHz, CDCl$_3$) δ 8.00 (d, J=7.2 Hz, 2H), 7.49-7.10 (m, 23H), 5.24 (dd, J=8.0, 9.6 Hz, 1H), 5.12 (br, 2H), 4.73 (s, 2H), 4.54-4.43 (m, 3H), 4.38-4.36 (m, 2H), 3.94 (d, J=3.2 Hz, 1H), 3.83 (m, 1H), 3.78 (m, 1H), 3.69-3.66 (m, 3H), 3.41 (m, 1H), 3.06 (m, 1H), 1.48-1.33 (m, 4H), 1.16-1.09 (m, 2H); $^{13}$C NMR (101 MHz, CDCl$_3$) δ 166.6, 156.6, 156.0, 138.0, 137.6, 133.1, 129.8, 129.7, 128.5, 128.4, 128.2, 128.0, 127.8, 127.7, 127.1, 101.0, 76.5, 75.4, 74.1, 73.5, 73.4, 73.1, 69.6, 69.5, 68.2, 67.0, 50.4, 50.1, 47.0, 46.0, 29.6, 29.0, 27.7, 27.3, 23.1; HRMS (ESI): calcd for C$_{47}$H$_{51}$NO$_9$Na [M+Na]$^+$: 796.3462, found: 796.3464.

Example A-34: Synthesis of N-(Benzyl)benzyloxy-carbonyl-5-amino-pentanyl 2-O-acetyl-3,4-di-O-benzyl-α-L-rhamnopyranosyl-(1→3)-4,6-di-O-benzyl-2-O-benzoyl galactopyranoside (38*)

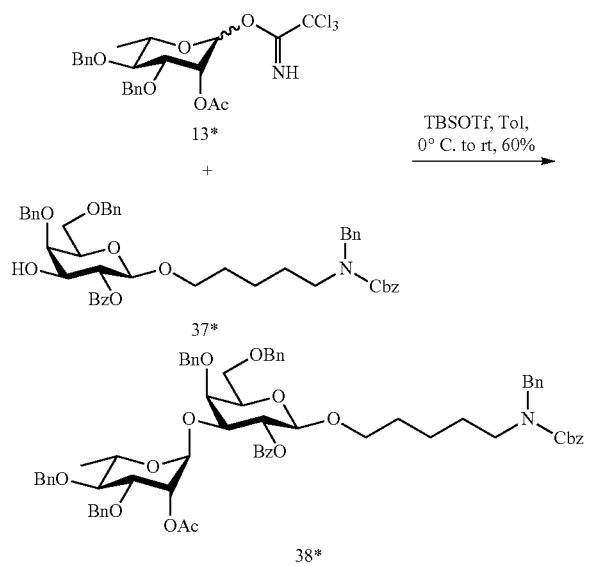

Acceptor 37* (25 mg, 0.032 mmol) and donor 13* (34 mg, 0.065 mmol) were dissolved in toluene (1 mL). 4A MS (100 mg) was added. The mixture was stirred at rt for 30 min, then cooled to 0° C. TBSOTf (0.1 mL, 0.06 M) in toluene was slowly added. After 3 h, the reaction was quenched with Et$_3$N. The mixture was filtered and concentrated in vacuo. The residue was purified by column chromatography on silica gel (Hexanes/EtOAc=1.8/1 to 1/1) to give disaccharide 38* (22 mg, 60%) as a white foam. [α]$_D^{25}$=10.42 (c=0.22, CHCl$_3$); $^1$H NMR (400 MHz, CDCl$_3$) δ 8.02 (d, J=7.6 Hz, 2H), 7.46-7.07 (m, 33H), 5.67 (dd, J=8.0, 10.0 Hz, 1H), 5.21 (m, 1H), 5.11 (m, 2H), 4.93-4.82 (m, 3H), 4.56-4.50 (m, 2H), 4.47-4.40 (m, 3H), 4.37-4.33 (m, 3H), 4.15 (d, J=11.2 Hz, 1H), 3.97 (m, 1H), 3.89 (m, 1H), 3.86-3.81 (m, 2H), 3.75 (dd, J=3.2, 9.2 Hz, 1H), 3.67 (m, 1H), 3.61 (m, 1H), 3.39-3.30 (m, 2H), 3.04 (m, 1H), 2.92 (m, 1H), 1.83 (s, 3H), 1.38 (m, 4H), 1.29 (d, J=6.0 Hz, 3H), 1.13 (m, 2H); $^{13}$C NMR (101 MHz, CDCl$_3$) δ 169.4, 165.0, 138.5, 138.3, 137.8, 137.8, 133.1, 129.8, 129.7, 128.5, 128.4, 128.3, 128.3, 128.2, 128.0, 127.9, 127.9, 127.7, 127.2, 101.5, 99.2, 79.6, 78.6, 77.5, 77.3, 75.4, 75.2, 74.9, 73.8, 73.7, 72.4, 71.5, 69.0, 68.5, 68.3, 67.1, 50.5, 50.2, 47.1, 46.1, 29.8, 29.1, 23.1, 21.2, 20.7, 18.2; HRMS (ESI): calcd for C$_{69}$H$_{75}$NO$_{14}$Na [M+Na]$^+$: 1164.5085, found: 1164.5069.

Example A-35: Synthesis of 5-amino-pentanyl α-L-rhamnopyranosyl-(1→3)-β-D-galactopyranoside (39*)

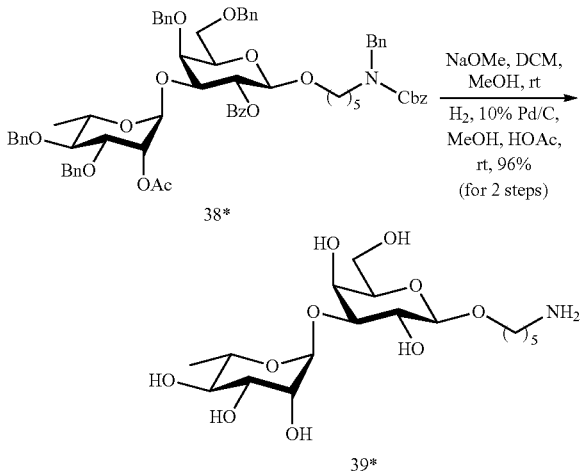

The disaccharide 38* (22 mg, 0.019 mmol) was dissolved in DCM and MeOH (1.2 mL, v/v=1/1). Sodium methoxide (5.2 mg, 0.096 mmol) was added. The mixture was stirred at rt overnight, then the mixture was neutralized with acid resin, filtered and concentrated in vacuo. The residue was purified by column chromatography on silica gel (Hex/AcOEt=1/1.5) to give the intermediate secondary alcohol, which was further dissolved in MeOH/H$_2$O/HOAc (5.55 mL, v/v/v=100/10/1) and treated with Pd/C (101 mg, 10%). The mixture was stirred under H$_2$ at rt. After 18 h, the mixture was filtered and concentrated. The residue was purified by Sep-pak® C18 (H$_2$O, 10% MeOH, 20% MeOH, 30% MeOH) to obtain disaccharide 39* (7.6 mg, 96% for two steps) as a white solid. [α]$_D^{25}$=173.72 (c=0.01, H$_2$O); $^1$H NMR (400 MHz, D$_2$O) δ 4.99 (br, 1H, H-1'), 4.42 (d, J=8.0 Hz, 1H, H-1), 4.04 (m, 1H, H-2'), 3.97 (m, 1H, H-4), 3.91 (m, 1H, OCH$_2$), 3.82 (m, 1H, H-5'), 3.79 (m, 1H, H-6), 3.74 (m, 1H, H-3'), 3.71 (m, 1H, H-5), 3.67-3.64 (m, 3H, OCH$_2$, H-6, H-3), 3.59 (m, 1H, H-2), 3.43 (t, J=9.6 Hz, 1H, H-4'), 2.97 (t, J=7.6 Hz, 2H, NCH$_2$), 1.69 (m, 2H, CCH$_2$C), 1.63 (m, 2H, CCH$_2$C), 1.43 (m, 2H, CCH$_2$C), 1.26 (d, J=6.4 Hz, 3H, H-6'); $^{13}$C NMR (101 MHz, D$_2$O) δ 102.3, 102.2, 80.4, 74.9, 71.7, 70.0, 69.9, 69.9, 69.8, 69.0, 68.2, 60.7, 39.2, 28.0, 26.2, 21.9, 16.4; HRMS (ESI): calcd for C$_{17}$H$_{35}$NO$_{10}$ [M+H]$^+$: 412.2183, found: 412.2180.

B. Biological Experiments

Example B-1: Conjugation of the Inventive Saccharides to CRM$_{197}$

The saccharide (1 equivalent) and bis-(4-nitrophenyl) adipate (7 equivalents) were added to a solution of pyridine and DMSO (1:1). The resulting mixture was stirred for 5 minutes for complete solubilization. Then, triethylamine (0.83 μL, 6 μmol, 10 equivalents) was added and the mixture was stirred for further 20 minutes. TLC indicated complete consumption of the starting material. The solvent was removed in vacuum. The residue was washed with dichloromethane (3×1 mL) to remove the excess of bis-(4-nitrophenyl) adipate and the white solid obtained was dried in vacuum.

40 equivalents of lyophilized $CRM_{197}$ was dissolved in 0.4 mL of sterile 0.1M sodium phosphate, pH 8.0 and transferred into upper chamber of 10,000 Da Millipore centrifugal filter (0.5 mL). The glass vial was rinsed with 3×0.4 mL of sterile 0.1M sodium phosphate, pH 8.0 and the rinsing solution was transferred to the same centrifugal filter. Following centrifugation at 10,000 rpm for 6-8 min (if needed, the centrifugation step is prolonged such that volume in upper chamber is 80-100 µL), the $CRM_{197}$ solution was then transferred into 1.5 mL tube containing the lyophilized saccharide derivatized with PNP ester and shacked slowly (around 180-200 rpm) for 18-24 h at room temperature. The conjugate was washed once with 0.1M sodium phosphate, pH 8.0 and 2-3 times with deionized, autoclaved water using 10,000 Da Millipore centrifugal filters. The average molecular size of the conjugate was determined by MALDI-MS analysis using $CRM_{197}$ as standard and calculate the average oligosaccharides attachments with per $CRM_{197}$ molecule.

Following the procedure, the hexasaccharide 23* was conjugated to $CRM_{197}$. Conjugate $CRM_{197}$-23*: ca. m/z 65705.7 (incorporation of 8 hexasaccharide molecules on average);

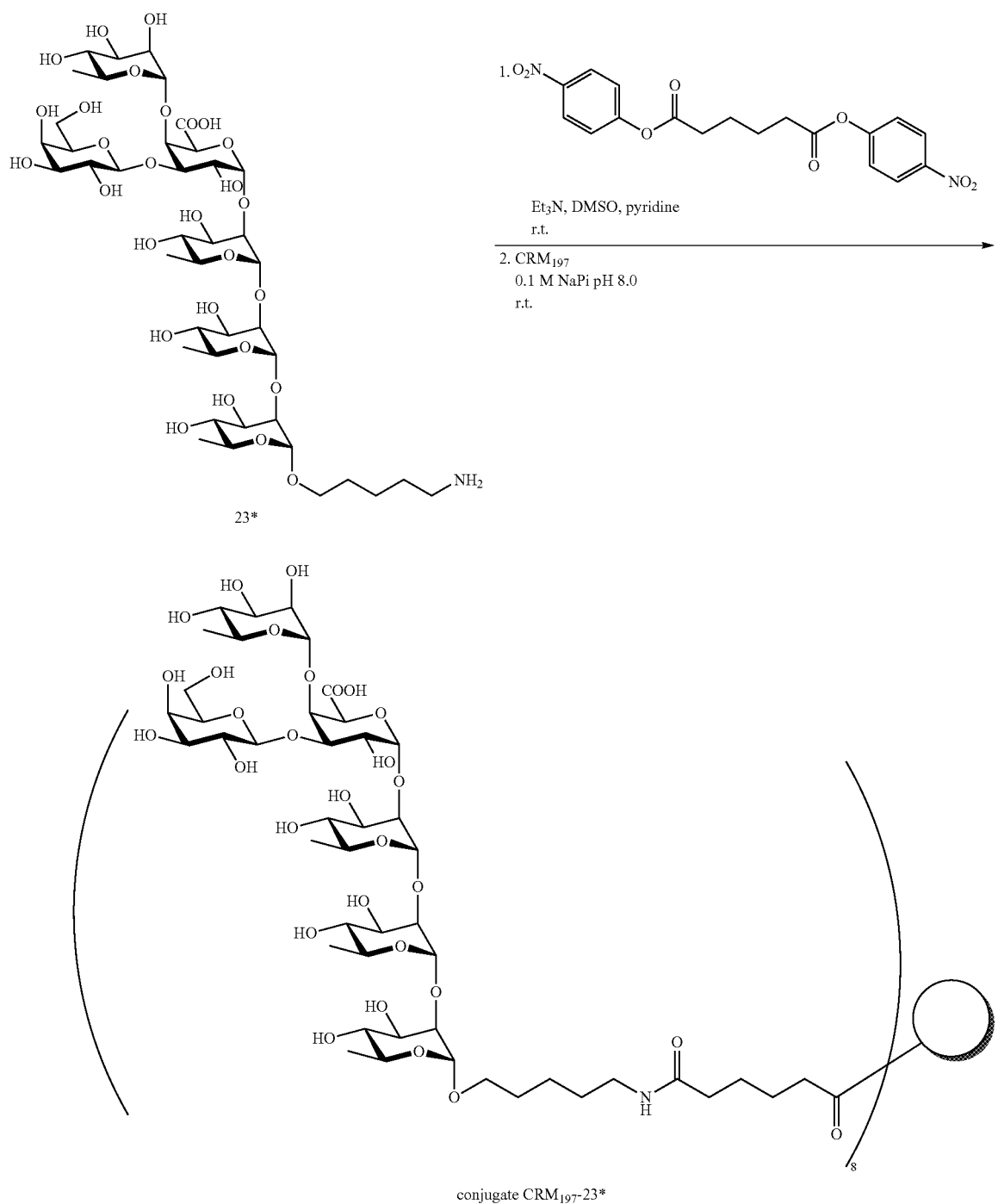

conjugate $CRM_{197}$-23*

Example B-2: Evaluation of the Immune Response Against the Conjugate CRM$_{197}$-23* in Mice Preparation of Microarrays Slides:

The CodeLink NHS activated glass slides (Surmodics) were spotted with synthetic glycans, polysaccharides, protein (CRM$_{197}$) and BSA-Spacer-dimannose at two different concentration (100 µM and 200 µM) in printing buffer (50 mM sodium phosphate, pH 8.5) by using a S3 piezoelectric microarray printer (Scienion) equipped with a type 4 coated nozzle (see FIG. 7A). The relative humidity of spotted chamber was constantly maintained at 65%. The spotted slides were incubated over night at room temperature in a humidifying chamber. The unreactive groups on the slides were blocked with 50 mM sodium phosphate, 100 mM ethanolamine pH 9.0 at room temperature for one hour. Slides were subsequently washed three times for 5 min with water, dried by centrifugation at 300 g for 5 min (CombiSlide system, Eppendorf) and stored at 4° C. until use.

Mice:

Six to eight week old female C57BL/6J inbred strains of mice were obtained from the Charles River, Sulzfeld (Germany). Animals were rested and handled in accordance with the Institutional Animal Ethics guidelines.

Mice Immunization and Generation of Polyclonal Sera

Groups of 3 C57BL/6J female 6-8 week old inbred mice were immunized subcutaneously with conjugate CRM$_{197}$-23* emulsified with 1:1 (v/v) Freund's adjuvant (3 µg of hexasaccharide 23*). On day 14 and 35 mice received a booster injection with the same amount of antigen emulsified with 1:1 (v/v) Freund's adjuvant. Mice were bled submandibularly weekly using sterile single-use blood lancet. Control mice received only alum in PBS. The antibody responses were measured by glycan microarray.

The hexasaccharide 23*-specific endpoint antibody titers of IgG and IgM in pooled sera were analyzed by glycan microarray for every week after the immunization as expressed in MFI (FIGS. 4B, 4C, 4G and 4H). The hexasaccharide-specific IgG subclasses were quantified by glycan microarray (FIG. 4D-4F). The results indicated that IgG1 and IgG2a were contributed bulk of the antigen-specific IgG titer.

The polyclonal sera (1 in 200 dilutions in 1% BSA-PBS) were further analyzed using microarray slides printed with oligosaccharides related to the capsular polysaccharides from carbapenem-resistant K. pneumoniae and polysaccharides (capsular polysaccharides of K. pneumoniae bacteria).

Slides were blocked with PBS-BSA (1%) for 1 h at room temperature and washed 3 times with PBS. The slides were dried by centrifugation at 1200 rpm for 5 min before use. A FlexWell 64 (Grace Bio-Labs, Bend, Oreg., USA) grid was applied to microarray slides. Slides were incubated with polyclonal sera raised in mice against the conjugate CRM$_{197}$-hexasaccharide 23* at multiple dilutions, diluted in 1% BSA in PBS (w/v) and incubated in a humid chamber for 1 h at room temperature. Slides were washed three times with PBST (0.1% Tween-20 in PBS) and dried by centrifugation (300×g, 5 min). Slides were incubated with a fluorescence-labeled goat anti-mouse secondary antibodies (Life Technologies) diluted in 1% BSA in PBS (w/v) in a humid chamber for 1 h at room temperature, washed three times with PBST, rinsed once with deionized water and dried by centrifugation (300×g, 5 min) prior to scanning with a GenePix 4300A microarray scanner (Molecular Devices, Sunnyvale, Calif., USA). Image analysis was carried out with the GenePix Pro 7 software (Molecular Devices). The photomultiplier tube (PMT) voltage was adjusted such that scans were free of saturation signals.

The microarray data show that the conjugate CRM$_{197}$-23* is immunogenic in mice and exhibits robust antibody response (see FIG. 5B). The microarray data also attests that the hyperimmune sera raised in mice immunized with conjugate CRM$_{197}$-23* emulsified with Freund's adjuvant recognize not only the hexasaccharide 23*, but also trisaccharides Rha(α1-2)Rha(α1-2)Rha(α1-1)aminopentanol, Gal(β1-3)Rha(α1-2)GalA(α1-2)aminopentanol and capsular polysaccharide from carbapenem-resistant K. pneumoniae strain 34 (CPS K34).

Example B-3: Evaluation of the Immune Response Against the Conjugate CRM$_{197}$-23* in Rabbits Rabbit Immunization and Generation of Polyclonal Sera:

Ten to twelve week old female ZIKA rabbits (n=3) were subcutaneously immunized at four different sites with CRM$_{197}$-23* conjugate in alhydrogel (aluminum hydroxide) formulation at day 0 and boosted at day 14 and sera were collected at day 0, 14 and 21. The antibody response was analyzed by glycan microarray and ELISA.

ELISA:

The antibody titer of rabbit sera were analyzed by ELISA. The high binding ninety six well polystyrene microtiter plates (Corning, USA) were coated overnight at 4° C. with capsular polysaccharide of carbapenem-resistant K. pneumoniae strains (Carbohydr. Res. 2013, 369, 6-9) (50 µl of 10 µg/ml per well) in PBS, pH 7.2. The plates were washed thrice with PBS containing 0.1% Tween-20 (PBST) and blocked with 10% FCS in PBS at room temperature for 1 hr. After washing thrice with PBST, the plate was incubated with the individual and pooled rabbit serum (n=3) at different dilutions in duplicate at room temperature for 1 hr. The plate was washed 4-5 times with PBST and incubated with horseradish peroxidase (HRP) conjugated goat anti-rabbit total Ig antibodies (diluted 1 in 10,000 in 10% FCS-PBS) followed by incubation at room temperature another 1 hr. The plate was washed thoroughly with PBST and developed using HRP substrate 3, 3', 5, 5'-tetramethylbenzidine (Thermo Scientific, USA). The reaction was stopped by adding 2% H$_2$SO$_4$ and absorbance were recorded at 450 nm.

Glycan Microarray Analysis:

Glycan microarray analysis was performed as described in Example B-2 using the same printed slides. Mean fluorescence intensity of spots was plotted.

Analysis of the Antibody Response by ELISA

The antibody response was analyzed by ELISA in rabbit sera (n=3) immunized with 10 µg of glycan's equivalent conjugate on day 0 and boosted at day 14 subcutaneously.

The immune response was analyzed at different time points. The specific immunoglobulins by end point titer were quantified (FIG. 6B). The ELISA data proves that CRM$_{197}$-23* conjugate is immunogenic and induces high antibody titers. The booster response after immunization in terms of fold change was further analyzed (FIG. 6C). The antibody response for individual animal was calculated and plotted as fold change at day 0 and day 21. Hence, ELISA analysis shows that hexasaccharide 23* is immunogenic in rabbits and generates cross reactive antibodies.

Analysis of the Antibody Response by Microarray

To analyze the hexasaccharide 23* specific immune response, the microarray slide(s) were incubated with rabbit sera (n=3) collected at different time points before and after immunization with CRM$_{197}$-23* conjugate. The microarray data shows that the hexasaccharide 23* specific antibodies are cross-reactive with native polysaccharide and other synthetic glycans (FIG. 7B). The mean fluorescence intensity of antibodies was analyzed and plotted (FIG. 7C). The microarray data further attests that the hexasaccharide 23* is immunogenic in rabbits and induces cross-reactive antibodies. Thus, the microarray data attests that the hyperimmune sera raised in rabbits immunized with conjugate CRM197-23* recognize not only the hexasaccharide 23*, but also trisaccharides Rha(α1-2)Rha(α1-2)Rha(α1-1)aminopentanol, Gal(β1-3)Rha(α1-2)GalA(α1-2)aminopentanol and capsular polysaccharide from carbapenem-resistant *K. pneumoniae* strain 34 (CPS K34).

The invention claimed is:

1. A synthetic saccharide of general formula (II)

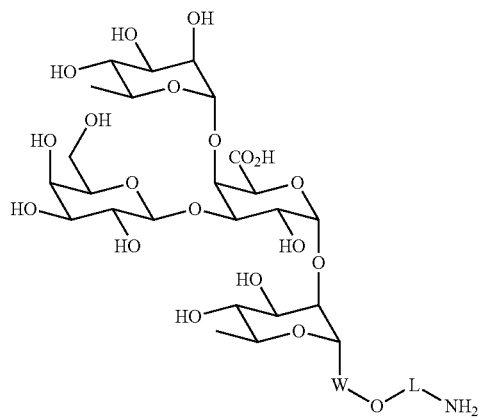

(II)

wherein

represents a bond,

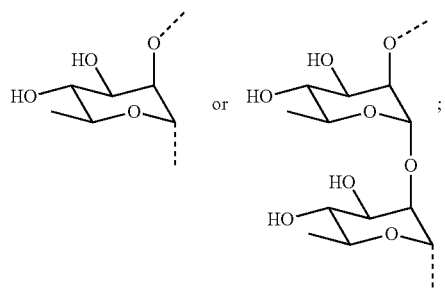

and
   L represents a linker;
   or a diastereoisomer or a pharmaceutically acceptable salt thereof.

2. The synthetic saccharide according to claim 1, wherein
   L- is selected from: -L$^a$-, -L$^a$-L$^e$-, -L$^a$-L$^b$-L$^e$-, -L$^a$-L$^d$-L$^e$-;
   L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$;
   L$^b$- represents —O—;

L$^d$- is selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;
   L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
   and o, q, p1 and p2 are independently of each other an integer selected from 1, 2, 3, 4, 5, and 6.

3. A conjugate comprising the saccharide according to claim 1.

4. The conjugate according to claim 3 of general formula (X)

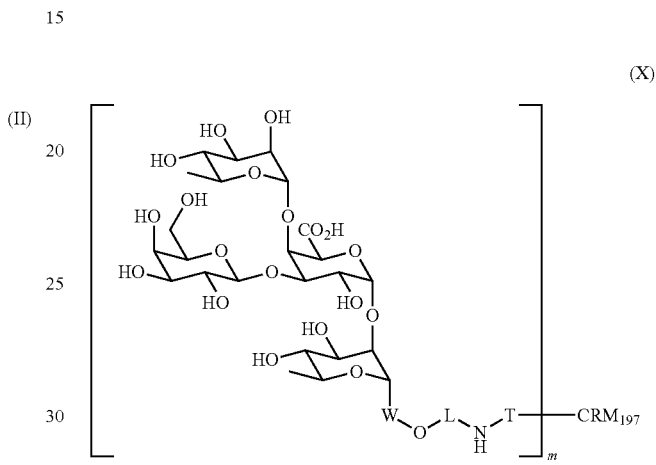

(X)

wherein

represents a bond,

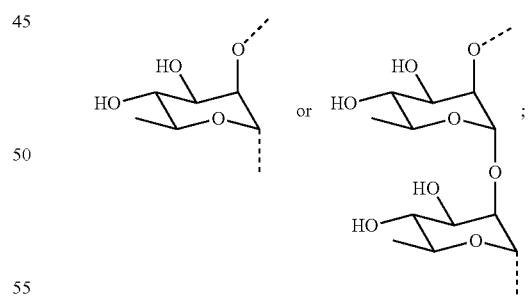

L represents a linker;
m is comprised between 2 and 18;
-T- is selected from:

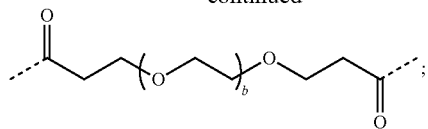

a represents an integer from 1 to 10; and
b represents an integer from 1 to 4.

5. The conjugate according to claim 4, wherein -T- represents

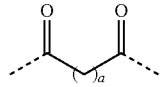

and a is an integer selected from 2, 3, 4, 5 and 6.

6. The conjugate according to claim 4, wherein -L- is selected from: $-L^a-$, $-L^a-L^e-$, $-L^a-L^b-L^e-$, $-L^a-L^d-L^e-$;

$L^a$- is selected from: $-(CH_2)_o-$, $-(CH_2-CH_2-O)_o-C_2H_4-$, $-(CH_2-CH_2-O)_o-CH_2$;

$L^b$- represents $-O-$;

$L^d$- is selected from: $-(CH_2)_q-$, $-(CF_2)_q-$, $-(CH_2-CH_2-O)_q-C_2H_4-$, and $-(CH_2-CH_2-O)_q-CH_2-$;

$L^e$- is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;

and o, q, p1 and p2 are independently of each other an integer selected from 1, 2, 3, 4, 5, and 6.

7. A method for raising a protective immune response in a human or animal host comprising administering to the human or animal host a saccharide according to claim 1, or a conjugate comprising the saccharide.

8. A method for increasing immunogenicity against or treating a disease associated with carbapenem-resistant *Klebsiella pneumoniae* comprising administering to a patient a saccharide according to claim 1.

9. A pharmaceutical composition comprising the saccharide according to claim 1 and/or a conjugate comprising the saccharide together with at least one pharmaceutically acceptable adjuvant or excipient.

10. A method comprising the use of the saccharide according to claim 1 as marker in immunological assays for detection of antibodies against carbapenem-resistant *Klebsiella pneumoniae*.

11. A method of synthesis of a saccharide of general formula (II)

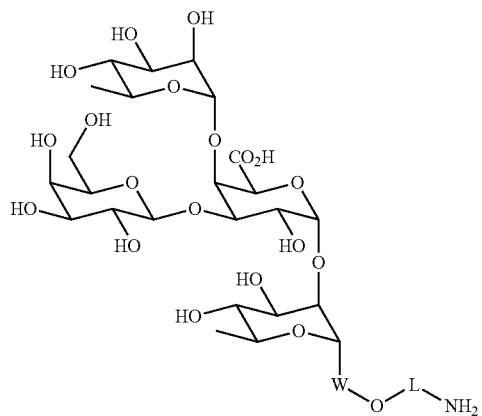

(II)

wherein

represents a bond,

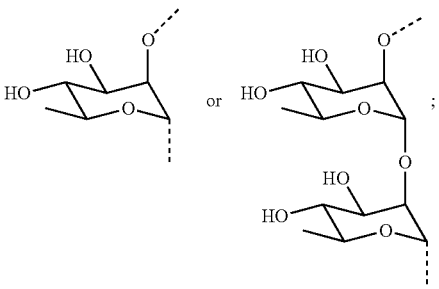

L represents a linker;
comprising the following steps:
A) reacting a compound 1 of the formula:

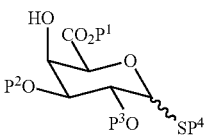

1 wherein $P^1$-$P^3$ represent protecting groups and $P^4$ is selected from:

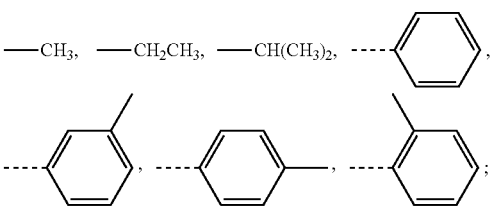

with a compound 2 of the formula:

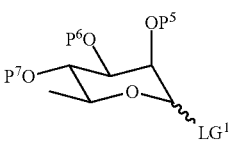

2 wherein $P^5$-$P^7$ represent protecting groups and $LG^1$ represents a leaving group selected from:

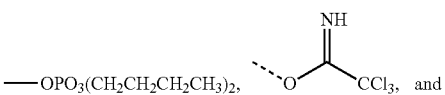

-continued

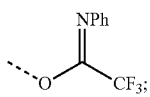

to provide a compound 3 of formula:

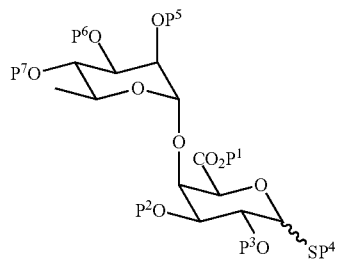

wherein $P^1$-$P^3$, $P^5$-$P^7$ represent protecting groups and $P^4$ is selected from:

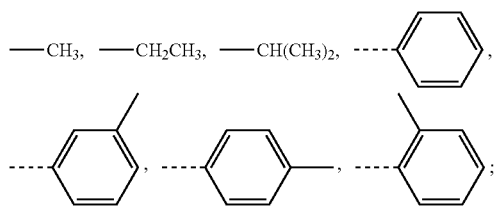

and
performing selective removal of protective group $P^2$ on compound 3 to obtain compound 4 of formula:

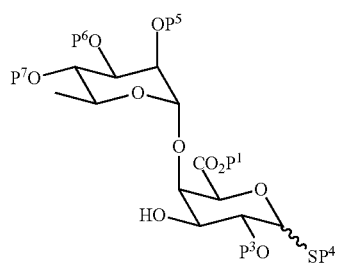

wherein $P^1$, $P^3$, $P^5$-$P^7$ represent protecting groups and $P^4$ is selected from:

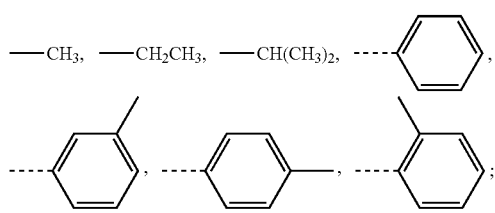

and
reacting compound 4 with compound 5 of formula:

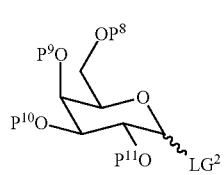

wherein $P^8$-$P^{11}$ represent protecting groups and $LG^2$ represents a leaving group selected from:

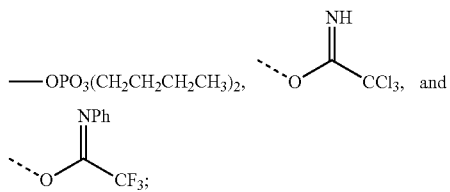

to obtain compound 6 of formula:

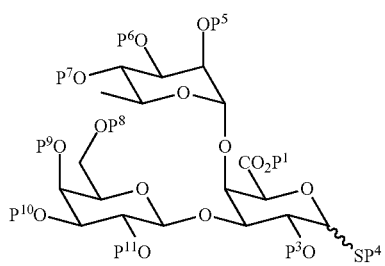

wherein $P^1$, $P^3$, $P^5$-$P^{11}$ represent protecting groups and $P^4$ is selected from:

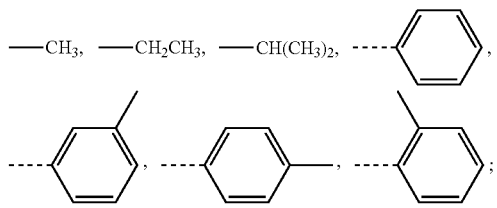

and
converting compound 6 to compound 7 of formula:

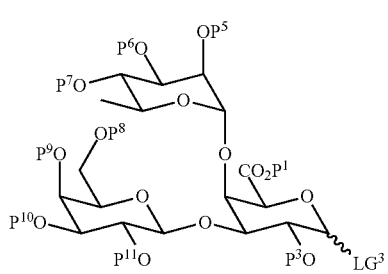

wherein $P^1$, $P^3$, $P^5$-$P^{11}$ represent protecting groups and $LG^3$ represents a leaving group selected from:

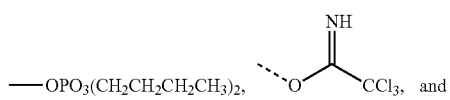

-continued

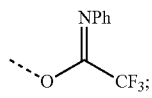

and

B1) reacting compound 2 with compound 8 of formula:

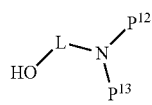

wherein $P^{12}$ and $P^{13}$ represent protecting groups to provide compound 9 of formula:

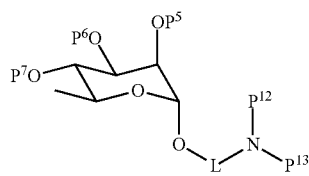

wherein $P^5$-$P^7$, $P^{12}$ and $P^{13}$ represent protecting groups; and performing selective removal of protective group $P^5$ on compound 9 to provide compound 10 of formula:

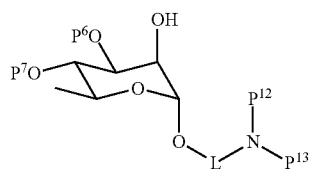

wherein $P^6$, $P^7$, $P^{12}$ and $P^{13}$ represent protecting groups; and

B2) reacting compound 2 with compound 10 to obtain compound 11 of formula:

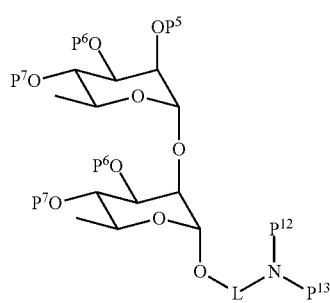

wherein $P^5$-$P^7$, $P^{12}$ and $P^{13}$ represent protecting groups; and performing selective removal of protective group $P^5$ on compound 11 to provide compound 12 of formula:

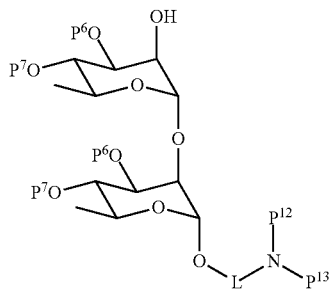

wherein $P^6$, $P^7$, $P^{12}$ and $P^{13}$ represent protecting groups; and

B3) reacting compound 2 with compound 12 to obtain compound 13 of formula:

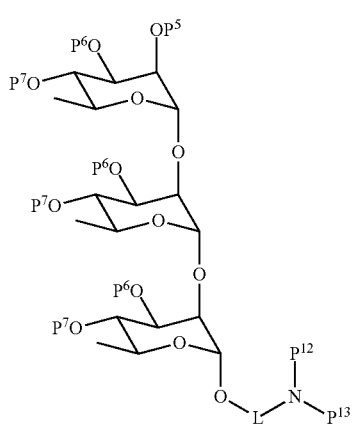

wherein $P^5$-$P^7$, $P^{12}$ and $P^{13}$ represent protecting groups; and performing selective removal of protective group $P^5$ on compound 13 to provide compound 14 of formula:

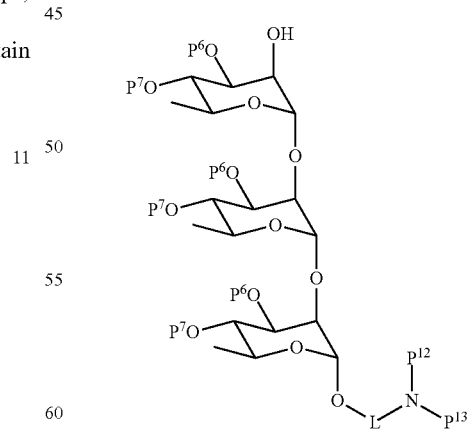

wherein $P^6$, $P^7$, $P^{12}$ and $P^{13}$ represent protecting groups; and

C1) reacting compound 7 obtained at step A with compound 10 obtained at step B1 to provide compound 15 of formula:

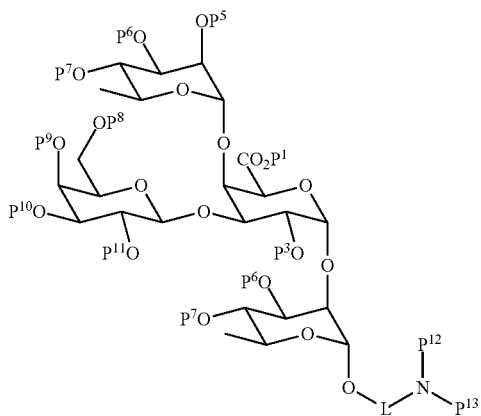

wherein $P^1$, $P^3$, $P^5$-$P^{13}$ represent protecting groups;
or

C2) reacting compound 7 obtained at step A with compound 12 obtained at step B2 to provide compound 16 of formula:

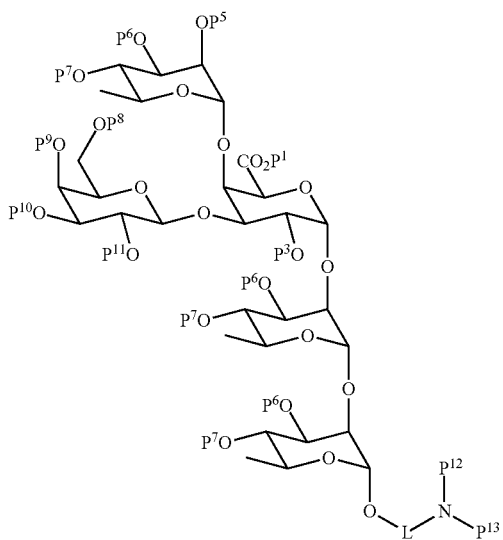

wherein $P^1$, $P^3$, $P^5$-$P^{13}$ represent protecting groups;

or

C3) reacting compound 7 obtained at step A with compound 14 obtained at step B3 to provide compound 17 of formula:

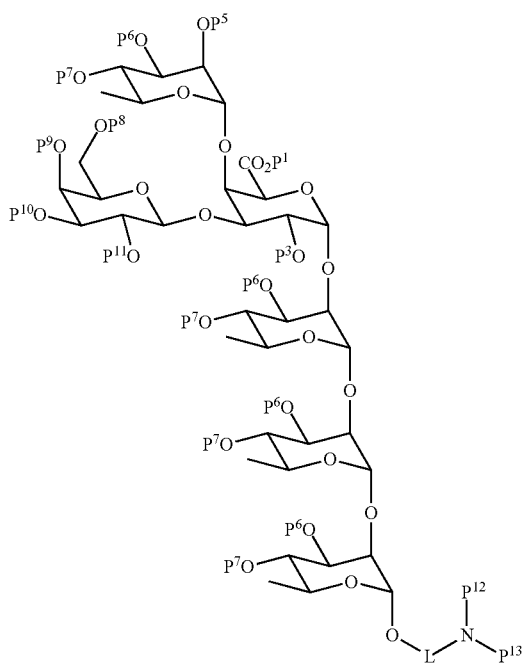

wherein $P^1$, $P^3$, $P^5$-$P^{13}$ represent protecting groups;

and

D) performing removal of protecting groups $P^1$, $P^3$, $P^5$-$P^{13}$ on compounds 15, 16 and 17 to provide the saccharides of general formula (II).

* * * * *